US007790169B2

(12) United States Patent
Lowery et al.

(10) Patent No.: US 7,790,169 B2
(45) Date of Patent: Sep. 7, 2010

(54) METHODS OF VACCINE ADMINISTRATION, NEW FELINE CALICIVIRUSES, AND TREATMENTS FOR IMMUNIZING ANIMALS AGAINST FELINE PARAOVIRUS AND FELINE HERPES VIRUS

(75) Inventors: David E. Lowery, Kalamazoo, MI (US); Sing Rong, Kalamazoo, MI (US); Paul M. Guimond, Kalamazoo, MI (US); Paula M. Clare, Kalamazoo, MI (US); Cassius M. Tucker, Kalamazoo, MI (US); Thomas Jack Newby, Bennet, NE (US)

(73) Assignee: Pfizer Inc., New York, NY (US)

( * ) Notice: Subject to any disclaimer, the term of this patent is extended or adjusted under 35 U.S.C. 154(b) by 619 days.

(21) Appl. No.: 11/494,825

(22) Filed: Jul. 28, 2006

(65) Prior Publication Data

US 2007/0031454 A1 Feb. 8, 2007

Related U.S. Application Data

(60) Provisional application No. 60/703,109, filed on Jul. 28, 2005.

(51) Int. Cl.
*A61A 35/00* (2006.01)
*C12N 7/00* (2006.01)

(52) U.S. Cl. .............. 424/185.1; 424/202.1; 424/216.1; 435/325.1

(58) Field of Classification Search .................. None
See application file for complete search history.

(56) References Cited

U.S. PATENT DOCUMENTS

| | | | |
|---|---|---|---|
| 3,937,817 A | 2/1976 | Frommer et al. |
| 3,944,469 A | 3/1976 | Bittle |
| 4,486,530 A | 12/1984 | David |
| 4,786,589 A | 11/1988 | Rounds |
| 5,169,789 A | 12/1992 | Bernstein |
| 5,229,293 A | 7/1993 | Matsuura |
| 5,266,313 A | 11/1993 | Esposito |
| 5,338,683 A | 8/1994 | Paoletti |
| 5,494,807 A | 2/1996 | Paoletti |
| 5,559,041 A | 9/1996 | Kang |
| 5,561,064 A | 10/1996 | Marquet |
| 5,580,859 A | 12/1996 | Felgner |
| 5,585,100 A | 12/1996 | Mond |
| 5,589,384 A | 12/1996 | Lipscombe |
| 5,589,466 A | 12/1996 | Felgner |
| 5,620,845 A | 4/1997 | Gould |
| 5,656,448 A | 8/1997 | Kang |
| 5,693,761 A | 12/1997 | Queen |
| 5,693,762 A | 12/1997 | Queen |
| 5,695,928 A | 12/1997 | Stewart |
| 5,703,055 A | 12/1997 | Felgner |
| 5,716,784 A | 2/1998 | DiCesare |
| 5,716,822 A | 2/1998 | Wardley |
| 5,718,901 A | 2/1998 | Wardley |
| 5,725,863 A | 3/1998 | Daniels |
| 5,728,587 A | 3/1998 | Kang |
| 5,800,821 A | 9/1998 | Acheson |
| 5,977,322 A | 11/1999 | Marks |
| 6,010,703 A | 1/2000 | Maes |
| 6,241,989 B1 | 6/2001 | Scott et al. |
| 6,355,246 B1 | 3/2002 | Kruger |
| 6,534,066 B1 | 3/2003 | Poulet |

FOREIGN PATENT DOCUMENTS

| | | |
|---|---|---|
| EP | 0484382 | 3/1995 |
| WO | 91/01332 | 2/1991 |
| WO | WO/91/01332 | * 2/1991 |
| WO | 98/56929 | 12/1998 |
| WO | WO2004/083390 | 9/2004 |
| WO | 2005/080416 | 9/2005 |

OTHER PUBLICATIONS

Riffkin et al., Gene 167:279-83.*
Abaza et al., J Prot Chem 11:433-44.*
Bittle, J. L. & Rubic, W. J., "Immunization Against Feline Calicivirus Infection," Am. J. Vet. Res. 37:275-78 (1976).

(Continued)

*Primary Examiner*—Patrick Nolan
*Assistant Examiner*—Bao Qun Li
(74) *Attorney, Agent, or Firm*—Brandon Boss; Michael J. Moran; E. Victor Donahue

(57) ABSTRACT

The present invention relates to a vaccine for immunizing a cat against feline viruses. The present invention also relates to a nucleic acid clone that encodes the capsid protein of the isolated feline calicivirus. The present invention further relates to a live or killed vaccine comprising the isolated feline calicivirus, a subunit vaccine comprising the capsid protein of the isolated feline calicivirus, a nucleic acid vaccine comprising a nucleic acid clone of the isolated feline calicivirus, and a recombinant virus vector vaccine comprising nucleic acid encoding the capsid protein of the isolated feline calicivirus. The present invention also relates to a method for identifying a feline calicivirus useful for producing a vaccine composition and for assays for diagnosing cats infected with feline calicivirus. Also disclosed is a method of immunizing animals, especially cats, against disease, in particular against feline calicivirus (FCV). The method includes administering to a cat therapeutically effective amounts of first and second FCV vaccines. The first vaccine is administered orally or parenterally (e.g., subcutaneously, intramuscularly, and the like). The second vaccine is administered orally or oronasally N days following administration of the first vaccine, wherein N is an integer from 3 to 120, inclusive. A third vaccine administration may also be given. The present invention also describes methods and materials for treating and immunizing animals with vaccine, and in particular cats against both FPV or Feline Parvovirus, which has also been called Panleukopenia or FPL and against another disease, FHV or Feline Herpes Virus, which has also been called Feline Rhinotracheitis Virus.

6 Claims, No Drawings

OTHER PUBLICATIONS

Burroughs, J.N. and Brown, F., J., "Physico-chemical Evidence for the Re-classification of the Caliciviruses," Gen. Virol., 22, pp. 281-285 (1974).

Clarke, I.N., and Lambden, P. R., "The molecular biology of caliciviruses," J. Gen. Virol. 78: 291-301 (1997).

Dawson, S. et al., "Investigation of vaccine reactions and breakdowns after feline calicivirus vaccination," (Abstract), Vet. Rec. 132:346-50 (1993).

Lauritizen, Alice, et al., "Serological analysis of feline calicivirus isolates from the United States and United Kingdom," Vet Microbiology 56: 55-63 (1997).

Oglesby, Alice S., et al., "Biochemical and biophysical properties of vesicular exanthema of swine virus," (Abrtract), Virology 44, pp. 329-341 (1971).

Poulet, H., et al., "Immunisation with a combination of two complementary feline calicivirus strains induces a broad cross-protection against heterologous challenges," Veterinary Microbiology 106: 17-31 (2005).

Poulet, H., et al., "Comparison between acute oral/respiratory and chronic stomatitis/gingivitis isolates of feline calicivirus: pathogenicity, antigenic profile and cross-neutralisation studies," Archives of Viroloav 145: 243-261 (2000).

Soergel, ME., et al., "Biophysical Comparisons of Calicivirus Serotypes Isolated from Pinnipeds," Intervirology, 5, pp. 239-244 (1975).

Yokoyama, N., et al., "Recombinant feline herpesvirus type 1 expressing immunogenic proteins inducible virus neutralizing antibody against feline calicivirus in cats," (Abstract), Vaccine, vol. 14, No. 17/18, pp. 1657-1663 (1996).

PCT International Search Report, PCT/IB2006/002018.

Database EMBL Feline calicivirus: capsid protein, 2003, "Q7TER8" abstract.

Database EMBL Feline calicivirus: Feline calicivirus capsid protein precursor & Orf3 genes, complete cds., 2003, "AY299541" abstract.

Neill et al., "Nucleotide Sequence and Expression of the Capsid Protein Gene of Feline Calicivirus", Journal of Virology, 65(10):5440-5447, 1991.

Database EMBL Feline calicivirus, Feline calicivirus capsid protein gene (put.), complete cds., 1990, "M32819" abstract.

Database EMBL Feline calicivirus, Feline calicivirus CFI/68 RNA helicase/cysteine protease/RNA-dependent RNA polymerase polyprotein precursor and capsid protein precursor, genes, complete cds. and unknown gene, 1994, "U13992" abstract.

Sykes, "Feline Chlamydiosis", Clinical Techniques in Small Animal Practice, 20(2):129-134, 2005.

Schwantes et al., "Application of Chimeric Feline Foamy Virus-Based Retroviral Vectors for the Induction of Antiviral Immunity in Cats", Journal of Virology, 77(14):7830-7842, 2003.

Sommerville et al., "DNA Vaccination against feline calicivirus infection using a plasmid encoding the mature capsid protein", Vaccine, 20(13-14):1787-1796, 2002.

McCabe et al., "Vaccination of cats with an attenuated recombinant myxoma virus expressing feline calicivirus capsid protein", Vaccine, 20(19-20):2454-2462, 2002.

* cited by examiner

METHODS OF VACCINE ADMINISTRATION, NEW FELINE CALICIVIRUSES, AND TREATMENTS FOR IMMUNIZING ANIMALS AGAINST FELINE PARAOVIRUS AND FELINE HERPES VIRUS

CROSS-REFERENCE TO RELATED APPLICATIONS

This application claims the benefit of U.S. Provisional Patent Application 60/703,109 filed on Jul. 28, 2005, which is incorporated herein by reference in its entirety.

FIELD OF INVENTION

The present invention relates to providing new ways to administer various vaccines to various animals. It discloses several isolated feline caliciviruses (FCV). It discloses new methods of presenting FCV vaccines to cats. The present invention also relates to nucleic acid clones that encode feline caliciviruses. It relates to FCV capsid proteins, live or killed vaccines, a subunit vaccine comprising the capsid protein, a nucleic acid vaccine, and a recombinant virus vector vaccine comprising nucleic acids encoding the capsid protein of the isolated feline calicivirus. The present invention also relates to a method for identifying a feline calicivirus useful for producing a vaccine composition and assays for diagnosing cats infected with feline calicivirus. The present invention also provides for new ways to administer new and old FCV vaccines to felines.

BACKGROUND OF THE INVENTION

Caliciviruses are reported to be an important cause of illness in cats. A wide variety of symptoms are observed such as fever, rhinitis, sneezing, mild conjunctivitis, ocular discharge, vesicles in the external nares, oral mucosa or on the tongue, pneumonia, tracheal bronchitis, diarrhea, muscle soreness, stiff gate, and hyperesthesia. Opportunistic bacterial infections often accompany FCV infections, which complicate treatment and recovery. Severe FCV infections may lead to death, especially in juvenile cats. It should be noted that such signs, although reportedly common in natural cases, are not always prominent in experimental infections. It would appear that various field strains of feline calicivirus (FCV) either differ in their disease-causing potential, or that concurrent infection with other agents influences the disease symptoms.

Vaccines against feline calicivirus have been available for more than two decades. Although numerous FCV serotypes exist, certain strains, such as F9, were found to induce antibodies against a broad range of FCV strains. See J. L. Bittle & W. J. Rubic, *Am. J. Vet. Res.* 37:275-78 (1976). As a result, the earliest vaccines against feline calicivirus employed a modified or attenuated version of the FCV-F9 strain. See U.S. Pat. No. 3,937,812 to J. L. Bittle & W. J. Rubic, which is herein incorporated by reference in its entirety.

While the vaccines from FCV-F9 and other commercially available vaccines provide protection from many field isolates, it is not true that these vaccines prevent infection from all strains. Moreover, as FCV continues to evolve, FCV-F9 based vaccine provides protection against fewer and fewer field isolates (Lauritzen et al., 1997, Vet Microbiology, 56:55-63). In addition, veterinary practitioners have expressed concerns over the efficacy of vaccines based on a single serotype. Indeed, field studies suggest that vaccines derived from the FCV-F9 strain provide insufficient immunity against many strains of feline calicivirus. See, e.g., N. C. Pederson et al., *Feline Pract.* 13(1):26-35 (1983); S. Dawson et al., *Vet. Rec.* 132:346-50 (1993). Practitioners have also raised concerns about the administration of a modified live virus that may, in some circumstances, cause disease in otherwise healthy animals. Researchers have reported that inadvertent oral dosing of a subcutaneously-administered FCV vaccine resulted in acute disease. See R. C. Povey, *Feline Pract.* 7(5):12-16 (1977). There is, therefore, continued interest in developing a vaccine, which by itself or in combination with other vaccines, would provide the desired protection upon vaccination of a cat. We describe several isolates here which have been isolated from cats and provide a means of providing broad protection in immunized cats.

INFORMATION DISCLOSURE

U.S. Patent Documents

U.S. Pat. No. 3,937,812 February/1976 Bittle et al., U.S. Pat. No. 3,944,469 March/1976 Bittle et al.
U.S. Pat. No. 4,486,530 December/1984 David et al., U.S. Pat. No. 4,786,589 November/1988 Rounds et al.,
U.S. Pat. No. 5,169,789 December/1992 Bernstein et al., U.S. Pat. No. 5,229,293 July/1993 Matsuura et al.
U.S. Pat. No. 5,266,313 November/1993 Esposito et al., U.S. Pat. No. 5,338,683 August/1994 Paoletti et al.
U.S. Pat. No. 5,494,807 February/1996 Paoletti et al., U.S. Pat. No. 5,559,041 September/1996 Kang et al.
U.S. Pat. No. 5,561,064 October/1996 Marquet et al., U.S. Pat. No. 5,580,859 December/1996 Felgner
U.S. Pat. No. 5,585,100 December/1996 Mond et al., U.S. Pat. No. 5,589,384 December/1996 Liscombe
U.S. Pat. No. 5,589,466 December/1996 Felgner, U.S. Pat. No. 5,620,845 April/1997 Gould et al.
U.S. Pat. No. 5,656,448 August/1997 Kang et al., U.S. Pat. No. 5,693,761 December/1997 Queen et al.
U.S. Pat. No. 5,693,762 December/1997 Queen et al., U.S. Pat. No. 5,695,928 December/1997 Stewart et al.
U.S. Pat. No. 5,703,055 December/1997 Felgner, U.S. Pat. No. 5,716,784 February/1998 DiCesare
U.S. Pat. No. 5,716,822 February/1998 Wardley, U.S. Pat. No. 5,718,901 February/1998 Wardley
U.S. Pat. No. 5,725,863 March/1998 Daniels et al., U.S. Pat. No. 5,728,587 March/1998 Kang et al.
U.S. Pat. No. 5,800,821 September/1998 Acheson et al., U.S. Pat. No. 5,977,322 November/1999 Marks et al.
U.S. Pat. No. 6,010,703 January/2000 Maes et al., U.S. Pat. No. 6,355,246 March/2002 Kruger et al.
U.S. Pat. No. 6,534,066 B1 March/2003 Poulet et al.

Foreign Patent Documents

0484382 March/1995 EP, WO2004/083390

Other Publications

Burroughs, J. N and Brown, F., J. Gen. Virol., 22, pp. 281-285 (1974).
Clarke and Lambden in J. Gen. Virol. 78: 291-301 (1997).
Griest, N. R., 1979, Diagnostic methods in clinical virology (3rd ed.), pp. 84-85, Blackwell
J. L. Bittle & W. J. Rubic, *Am. J. Vet. Res.* 37:275-78 (1976).
Lauritzen et al., Vet Microbiology 56: 55-63 (1997).
Maky, Brian W. J. and Kangro, Hillar O. 1996, Virology methods manual, pp. 35-37, Academic Press, New York.
Motin et al., Infect. Immun. 64: 4313-4318 (1996).

N. C. Pederson et al., Feline Pract. 13(1):26-35 (1983).
Oglesby, A. S., et al., Virology 44, pp. 329-341 (1971).
Poulet et al., Veterinary Microbiology 106: 17-31 (2005).
Poulet et al., Archives of Virology 145: 243-261 (2000).
R. C. Povey, Feline Pract. 7(5):12-16 (1977).
S. Dawson et al., Vet. Rec. 132:346-50 (1993).
Scientific Publishers, Oxford, UK.
Soergel, M. E., et al., Intervirology, 5, pp 239-244 (1975).
Yokoyama, N., et al., Vaccine, vol. 14, No. 17/18, pp. 1657-1663 (1996).

SUMMARY OF THE INVENTION

The present invention provides new strains of and relates to several isolated feline caliciviruses (FCV). It also discloses new methods of presenting vaccines to animals and particularly, FCV vaccines to cats. The present invention also relates to nucleic acid clones that encode feline caliciviruses. It relates to FCV capsid proteins, live or killed vaccines, a subunit vaccine comprising the capsid protein, a nucleic acid vaccine, and a recombinant virus vector vaccine comprising nucleic acids encoding the capsid protein of the isolated feline calicivirus. The present invention also relates to a method for identifying a feline calicivirus useful for producing a vaccine composition and assays for diagnosing cats infected with feline calicivirus. The present invention also provides for new ways to administer new and old FCV vaccines to felines. Also described herein are methods and materials for treating and immunizing animals with vaccine, and in particular cats, against both FPV or Feline Parvovirus, which has also been called Panleukopenia or FPL and against another disease, FHV or Feline Herpes Virus, which has also been called Feline Rhinotracheitis Virus. Described below are novel combinations of vaccines, that when presented to a feline in the manner described allow for effective oral/oral and subq/oral deliveries of both FPV and or FHV vaccines.

In particular the present invention discloses the following vaccines for immunizing cats against feline calicivirus. A FCV-21 capsid protein or an isolated FCV-21 capsid protein, (SEQ ID 13) and sequences having at least about 91.2%, 95% and 99% identity. A DNA vaccine comprising nucleic acid sequences that code for a FCV-21 capsid protein or an isolated FCV-21 capsid protein wherein said DNA comprises a sequence (SEQ. ID 12) and sequences having at least about 78.7%, and 79.2% sequence identity and allowing for conservative substitutions.

A vaccine comprising a FCV-49 capsid protein or an isolated FCV-49 capsid protein wherein said capsid protein comprises a protein sequence from strain FCV-49 (SEQ ID 15) and sequences having at least about 92.7%, 95% and 99% identity; wherein said capsid protein is provided in an effective amount. A DNA vaccine comprising nucleic acid sequences that code for a FCV-49 capsid protein or an isolated FCV-49 capsid protein wherein said DNA comprises a sequence (SEQ. ID 14) and sequences having at least about 78.9%, i.e. 79.4% (78.9+0.5) sequence identity and allowing for conservative substitutions.

A vaccine comprising a FCV-26391-4 capsid protein, or an isolated FCV-26391-4 capsid protein, wherein said capsid protein comprises protein sequences from strain FCV-26391-4. A vaccine comprising an FCV-26391-4 capsid protein wherein said capsid protein comprises protein sequence (SEQ ID 17) and sequences having at least about 91.8%, 95% and 99% identity. A DNA vaccine comprising nucleic acid sequences that code for a FCV-26391-4 capsid protein or an isolated FCV-26391-4 capsid protein wherein said DNA comprises a sequence (SEQ. ID 16) and sequences having at least about 78.4%, i.e. 78.9% (78.4+0.5) sequence identity.

A vaccine where the polynucleotide is selected from the group consisting essentially of SEQ ID NOS. 12, 14, 16. The vaccines may be either alone or in any combination of the following: where it contains an adjuvant, wherein the FCV component is live, wherein the FCV component is attenuated, wherein the FCV component is inactivated, which may include at least one other feline calicivirus strain selected from the group consisting of FCV-F9, FCV-LLK, FCV-M8, FCV-255, and FCV-2280.

A vaccine to immunize cats against feline calicivirus which comprises a nucleotide sequence of a FCV capsid protein selected from the group consisting of a polypeptide having 93% or greater identity with SEQ ID NO. 13, 15, or 17, wherein the FCV isolate is not strain 213-95, and wherein the nucleic acid sequence is operably linked to a heterologous promoter sequence, in an effective amount to produce an immune response, and a pharmaceutically acceptable carrier. A vaccine to immunize cats against feline calicivirus which comprises a nucleotide sequence of a FCV capsid protein selected from the group selected from the group consisting essentially of SEQ ID NOS. 12, 14 and 16. A vaccine wherein the nucleotide sequence is in any of the following: a plasmid, a recombinant virus vector, or any other nucleotide vector.

A vaccine wherein the recombinant virus vector is selected from the group consisting of feline herpesvirus, raccoon poxvirus, canary poxvirus, adenovirus, Semliki Forest virus, Sindbis virus, and vaccinia virus.

There are also descriptions of an immunogenic compositions comprising a veterinarily acceptable vehicle of excipient and an isolated strain of FCV that binds to a monoclonal antibody selected from the monoclonal antibodies described herein as 23, 26, 41, 44 and 56. In some versions of the invention the immunogenic composition comprising a veterinarily acceptable vehicle of excipient and an isolated strain of FCV selectively binds to a monoclonal antibody selected from the monoclonal antibodies described herein as 23, 26, 41, 44 and 56. These immunogenic compositions include compositions where the FCV strain is inactivated, where said FCV strain is a vaccine, and where the composition comprises an adjuvant.

The vaccines described here may include include at least one other feline pathogen, selected from the group consisting of feline herpesvirus, feline leukemia virus, feline immunodeficiency virus, *Chlamydia pssittaci*, and feline parvovirus, rabies virus and *Bordetella bronchiseptica*. The vaccine may also additionally comprises or be administered with an adjuvant.

DETAILED DESCRIPTION OF THE INVENTION

The present invention provides a vaccination regimen that significantly reduces mortality associated with feline calicivirus (FCV) and enhances the safety profile of FCV vaccines. Furthermore, the claimed vaccination regimen induces a broader serum cross neutralization profile than existing FCV-F9 vaccine protocols, which should provide better immunity across different strains of the feline calicivirus.

One aspect of the present invention provides a method of immunizing animals with vaccines, in particular, a cat against feline calicivirus. Two other feline diseases, FPV and FHV also have novel treatments described herein. The method comprises administering to the cat therapeutically effective amounts of a first vaccine, a second vaccine, and, optionally a third vaccine administration may also be given either within 120 days as above, or more often, after about a year as an annual booster. The first vaccine is administered parenterally (e.g., subcutaneously, intramuscularly, etc.). The second vaccine is administered orally or oronasally about N days following administration of the first vaccine, and the third vaccine is administered parenterally, orally, or oronasally about M days following administration of either the first or the second vaccines. Here, N and M are independently integers from 3 to 120, inclusive. Also preferred is where N is about 3 weeks and about 2-4 weeks. In addition we present one aspect of the invention where certain identified vaccines may be administered as two oral doses, with no need for a first parenteral administration. Annual boosters are also advised.

| BRIEF DESCRIPTION OF THE SEQUENCE LISTING |
|---|
| SEQ ID NO. 1: |
| Oligonucleotide primer, DEL-653 |
| SEQ ID NO. 2: |
| Oligonucleotide primer, DEL-651 |
| SEQ ID NO. 3: |
| Oligonucleotide primer, FCV-SR N2 |
| SEQ ID NO. 4: |
| Oligonucleotide primer, FCV-SR N3 |
| SEQ ID NO. 5: |
| Oligonucleotide primer, FCV-SR N4 |
| SEQ ID NO. 6: |
| Oligonucleotide primer, FCV-SR N5 |
| SEQ ID NO. 7: |
| Oligonucleotide primer, FCV-SR N6 |
| SEQ ID NO. 8: |
| Oligonucleotide primer, FCV-SR N9 |
| SEQ ID NO. 9: |
| Oligonucleotide primer, primer 2 |
| SEQ ID NO. 10: |
| Oligonucleotide primer, FCV-SR C4 |
| SEQ ID NO. 11: |
| Oligonucleotide primer, FCV-SR C8 |
| SEQ ID NO. 12: |
| DNA sequence of FCV-21 capsid gene |
| SEQ ID NO. 13: |
| Encoded amino acid sequence of FCV-21 capsid gene |
| SEQ ID NO. 14: |
| DNA sequence of FCV-49 capsid gene |
| SEQ ID NO. 15: |
| Encoded amino acid sequence of FCV-49 capsid gene |
| SEQ ID NO. 16: |
| DNA sequence of FCV-26391-4 capsid gene |
| SEQ ID NO. 17: |
| Encoded amino acid sequence of FCV-26391-4 capsid gene |

DEFINITIONS AND ABBREVIATIONS

"About," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17-25 days, and about 2-4 weeks is 10-40 days.

"Active immunity" includes both humoral immunity and/or cell-mediated immunity against feline viruses induced by vaccinating a cat with the vaccine of the present invention.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. An antibody that is "specific" for a given antigen indicates that the variable regions of the antibody recognize and bind a specific antigen exclusively—e.g., the antibody is able to distinguish a particular capsid protein from other known proteins by virtue of measurable differences in binding affinity, despite the existence of localized sequence identity, homology, or similarity between capsid proteins and other polypeptides. Specific antibodies may also interact with other proteins (for example, *Staphylococcus aureus* protein A or other antibodies in ELISA techniques) through interactions with sequences outside the variable region of the antibodies, and, in particular, in the constant regions of the molecule. Screening assays to determine binding specificity of an antibody are well known. For a comprehensive discussion of such assays, see Harlow et al. (ed.), *Antibodies: A Laboratory Manual* Chapter 6 (1988). Antibodies may also recognize and bind fragments of FCV capsid proteins, provided that the antibodies are specific for FCV capsid proteins. Antibodies can be produced using methods known in the art.

"Antigen" or "immunogen" refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to subunit antigens—antigens separate and discrete from a whole organism with which the antigen is associated in nature—as well as killed, attenuated or inactivated bacteria, viruses, fungi, parasites or other microbes. The term antigen also refers to antibodies, such as anti-idiotype antibodies or fragments thereof, and to synthetic peptide mimotopes that can mimic an antigen or antigenic determinant (epitope). The term antigen also refers to an oligonucleotide or polynucleotide that expresses an antigen or antigenic determinant in vivo, such as in DNA immunization applications.

"Excipient" refers to any component of a vaccine that is not an antigen.

FELOCELL 3 is FELOCELL 4 without *Chlamydia psittaci*

FELOCELL 4 contains modified-live feline rhiotracheitis virus [FHV], calicivirus [FCV-F9], panleukopenia virus [FPV] and *Chlamydia psittaci* [FCp]. FELOCELL 4A contains modified-live feline rhiotracheitis virus [FHV], calicivirus [FCV-21], panleukopenia virus [FPV] and *Chlamydia psittaci* [FCp]. FELOCELL 4 A is FELOCELL 4 without FCV-F9, but with FCV-21. FELOCELL 3 A is FELOCELL 3 without FCV-F9, but with FCV-21. Felocell® 4, Felocell 4, or FELOCELL 4 or these words followed by the number "3" or "4" are vaccines where any variation of the name Felocell is registered and owned by Pfizer.

"First vaccine," "second vaccine," "third vaccine," and the like, refer to separately administrable vaccines, which may be the same or different, and which in general may be administered in any order. Thus, a third vaccine may be administered to a subject before or after a second vaccine.

"Identity" with respect to percent amino acid sequence "identity" with respect to polypeptides is defined herein as the percentage of amino acid residues in the candidate sequence that are identical with the residues in the target sequences after aligning both sequences and introducing gaps, if necessary, to achieve the maximum percent sequence identity. Percent sequence identity is determined by conventional methods. Briefly, two amino acid sequences are aligned to optimize the alignment scores using the ClustalW algorithm (Thompson et al.; Nuc. Ac. Res. 22:4673-4680; 1994) and PAM250 weight matrix (Dayhoff et al., "Atlas of Protein Sequence and Structure." National Biomedical Research Foundation. Washington, D.C. 5:345-358 (1978) and default parameters as provided by the program MegAlign (DNASTAR, Inc.; Madison, Wis.). The PAM250 weight matrix table is presented as TABLE 1-1 (amino acids are indicated by the standard one-letter codes).

"Intranasal" administration refers to the introduction of a substance, such as a vaccine, into a subject's body through or by way of the nose and involves transport of the substance primarily through the nasal mucosa.

"Isolated," when used to describe any particularly defined substance, such as a polynucleotide or a polypeptide, refers to the substance that is separate from the original cellular environment in which the substance such as a polypeptide or nucleic acid is normally found. As used herein therefore, by way of example only, a recombinant cell line constructed with a polynucleotide of the invention makes use of the "isolated" nucleic acid. Alternatively the FCV capsid protein or a specific immunogenic fragment may be used is or as a vaccine thus it would be considered to be isolated because it had been identified, separated and to some extent purified as compared to how it may exist in nature. If the capsid protein or a specific immunogenic fragment thereof is produced in a recombinant bacterium or eukaryote expression vector that produces the antigen it is considered to exist as an isolated protein or nucleic acid. Example, a recombinant cell line constructed with a polynucleotide makes use of an "isolated" nucleic acid.

TABLE 1-1

|   | C | S | T | P | A | G | N | D | E | Q | H | R | K | M | I | L | V | F | Y | W |
|---|---|---|---|---|---|---|---|---|---|---|---|---|---|---|---|---|---|---|---|---|
| C | 12 | | | | | | | | | | | | | | | | | | | |
| S | 0 | 2 | | | | | | | | | | | | | | | | | | |
| T | -2 | 1 | 3 | | | | | | | | | | | | | | | | | |
| P | -3 | 1 | 0 | 6 | | | | | | | | | | | | | | | | |
| A | -2 | 1 | 1 | 1 | 2 | | | | | | | | | | | | | | | |
| G | -3 | 1 | 0 | -1 | 1 | 5 | | | | | | | | | | | | | | |
| N | -4 | 1 | 0 | -1 | 0 | 0 | 2 | | | | | | | | | | | | | |
| D | -5 | 0 | 0 | -1 | 0 | 1 | 2 | 4 | | | | | | | | | | | | |
| E | -5 | 0 | 0 | -1 | 0 | 0 | 1 | 3 | 4 | | | | | | | | | | | |
| Q | -5 | -1 | -1 | 0 | 0 | -1 | 1 | 2 | 2 | 4 | | | | | | | | | | |
| H | -3 | -1 | -1 | 0 | -1 | -2 | 2 | 1 | 1 | 3 | 6 | | | | | | | | | |
| R | -4 | 0 | -1 | 0 | -2 | -3 | 0 | -1 | -1 | 1 | 2 | 6 | | | | | | | | |
| K | -5 | 0 | 0 | -1 | -1 | -2 | 1 | 0 | 0 | 1 | 0 | 3 | 5 | | | | | | | |
| M | -5 | -2 | -1 | -2 | -1 | -3 | -2 | -3 | -2 | -1 | -2 | 0 | 0 | 6 | | | | | | |
| I | -2 | -1 | 0 | -2 | -1 | -3 | -2 | -2 | -2 | -2 | -2 | -2 | -2 | 2 | 5 | | | | | |
| L | -6 | -3 | -2 | -3 | -2 | -4 | -3 | -4 | -3 | -2 | -2 | -3 | -3 | 4 | 2 | 6 | | | | |
| V | -2 | -1 | 0 | -1 | 0 | -1 | -2 | -2 | -2 | -2 | -2 | -2 | -2 | 2 | 4 | 2 | 4 | | | |
| F | -4 | -3 | -3 | -5 | -4 | -5 | -4 | -6 | -5 | -5 | -2 | -4 | -5 | 0 | 1 | 2 | -1 | 9 | | |
| Y | 0 | -3 | -3 | -5 | -3 | -5 | -2 | -4 | -4 | -4 | 0 | -4 | -4 | -2 | -1 | -1 | -2 | 7 | 10 | |
| W | -8 | -2 | -5 | -6 | -6 | -7 | -4 | -7 | -7 | -5 | -3 | 2 | -3 | -4 | -5 | -2 | -6 | 0 | 0 | 17 |

The percent identity is then calculated as: Total number of identical matches ___ x 100 [length of the longer sequence + number of gaps introduced into the longer sequence in order to align the two sequences]

"Immune response" in a subject refers to the development of a humoral immune response, a cellular immune response, or a humoral and a cellular immune response to an antigen. A "humoral immune response" refers to one that is mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

"Immunologically protective amount" or "effective amount to produce an immune response" of an antigen is an amount effective to induce an immunogenic response in the recipient that is adequate to prevent or ameliorate signs or symptoms of disease, including adverse health effects or complications thereof, caused by infection with the disease agent and in particular with feline calicivirus. Either humoral immunity or cell-mediated immunity or both may be induced. The immunogenic response of an animal to a vaccine composition may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number and overall physical condition and overall health and performance of the subject. The immune response may comprise, without limitation, induction of cellular and/or humoral immunity. The amount of a vaccine that is therapeutically effective may vary depending on the particular virus used, or the condition of the cat, and can be determined by a veterinary physician.

"Monoclonal antibody" refers to antibodies produced by a single line of hybridoma cells, all directed towards one epitope on a particular antigen. The antigen used to make the monoclonal antibody can be provided as an isolated protein of the pathogen or the whole pathogen. A hybridoma is a clonal cell line that consists of hybrid cells formed by the fusion of a myeloma cell and a specific antibody-producing cell. In general, monoclonal antibodies are of mouse origin; however, monoclonal antibody also refers to a clonal population of an antibody made against a particular epitope of an antigen produced by phage display technology or method that is equivalent to phage display or hybrid cells of non-mouse origin.

"N days," "N" interval or period of time or "M-days" following an event refers, respectively, to any time on the N th or M th day after the event. For example, vaccinating a subject with a second vaccine 3 days following administration of a first vaccine means that the second vaccine is administered at any time on the 3rd day after the first vaccine. This description is often applied to the interval between a first and second vaccination. Typically the preferred N interval is about 3 weeks, or 17-25 days, but also common is from about 2-4 weeks or 10-40 days, and the inventions here are effective with "N" period of time of between 3 and 120 days.

"Oral" or "peroral" administration refers to the introduction of a substance, such as a vaccine, into a subject's body through or by way of the mouth and involves swallowing or transport through the oral mucosa (e.g., sublingual or buccal absorption) or both.

"Oronasal" administration refers to the introduction of a substance, such as a vaccine, into a subject's body through or by way of the nose and the mouth, as would occur, for example, by placing one or more droplets in the nose. Oronasal administration involves transport processes associated with oral and intranasal administration.

"Parenteral administration" refers to the introduction of a substance, such as a vaccine, into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration. For the purposes of this disclosure, parenteral administration excludes administration routes that primarily involve transport of the substance through mucosal tissue in the mouth, nose, trachea, and lungs.

"Passive immunity" refers to the protection against feline calicivirus provided to a cat as a result of vaccinating the cat with a vaccine comprising antibodies against the FCV strain or an immunogenic component or fragment of a component thereof.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"Polyclonal antibody" refers to a mixed population of antibodies made against a particular pathogen or antigen. In general, the population contains a variety of antibody groups, each group directed towards a particular epitope of the pathogen or antigen. To make polyclonal antibodies, the whole pathogen or an isolated antigen is introduced by inoculation or infection into a host that induces the host to make antibodies against the pathogen or antigen.

"Respiratory" administration refers to the introduction of a substance, such as a vaccine, into a subject's body through or by way of inhalation of a nebulized (atomized) substance. In respiratory administration, the primary transport mechanism involves absorption of the atomized substance through the mucosa in the trachea, bronchi, and lungs and is therefore different than intranasal or peroral administration.

"Single administrative dosage" means administered at or about the same day, that is all components administered within about 1 day. The components may or may not be in a single container.

"Specific for," when used to describe antibodies of the invention, indicates that the variable regions of the antibodies of the invention recognize and bind a specific virus strain exclusively (i.e., are able to distinguish a particular FCV capsid protein from other known proteins by virtue of measurable differences in binding affinity, despite the existence of localized sequence identity, homology, or similarity between FCV capsid proteins and such polypeptides). It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), *Antibodies: A Laboratory Manual*; Cold Spring Harbor Laboratory; Cold Spring Harbor, N.Y. (1988), Chapter 6. Antibodies that recognize and bind fragments of the FCV capsid proteins of the invention are also contemplated, provided that the antibodies are specific for FCV capsid proteins. Antibodies of the invention can be produced using any method well known and routinely practiced in the art.

"Specific immunogenic fragment" is meant a portion of a sequence that is recognizable by an antibody that is specific for the sequence, as defined in detail below.

"Subject" refers to any animal having an immune system, which includes mammals such as cats.

"Subunit vaccine" refers to a type of vaccine that includes one or more antigens, but not all antigens, which are derived from or homologous to, antigens from a pathogen of interest, such as a virus, bacterium, parasite or fungus. Such a composition is substantially free of intact pathogen cells or pathogenic particles, or the lysate of such cells or particles. Thus, a subunit vaccine can be prepared from at least partially purified, or substantially purified, immunogenic polypeptides from the pathogen or its analogs. Methods of obtaining an antigen or antigens in the subunit vaccine include standard purification techniques, recombinant production, or chemical synthesis.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, *Virology Methods Manual* 25-46 (1996).

"Therapeutically effective amount," in the context of this disclosure, refers to an amount of an antigen or vaccine that would induce an immune response in a subject (e.g., cat) receiving the antigen or vaccine which is adequate to prevent or ameliorate signs or symptoms of disease, including adverse health effects or complications thereof, caused by infection with a pathogen, such as a virus (e.g., FCV), bacterium, parasite or fungus. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number and overall physical condition and overall health and performance of the subject. The amount of a vaccine that is therapeutically effective may vary depending on the particular virus used, or the condition of the subject, and can be determined by a physician.

"Treating" refers to reversing, alleviating, inhibiting the progress of, or preventing a disorder, condition or disease to which such term applies, or to preventing one or more symptoms of such disorder, condition or disease.

"Treatment" refers to the act of "treating" as defined immediately above.

"Vaccine" refers to a composition that includes an antigen and encompasses so-called "subunit vaccines" as defined below. Administration of the vaccine to a subject results in an immune response. The vaccine may be introduced directly into the subject by any known route of administration, including parenterally, perorally, and the like.

Part 1

Vaccines, Virus Strains, Capsid Proteins, and Antibodies of the Invention

The present invention provides vaccines that are based upon live or killed FCV strains selected from the group consisting of FCV-21, FCV-49 and FCV26391-4. The invention additionally provides nucleic acid vaccines encoding an FCV capsid protein from the FCV strains of the invention or specific immunogenic fragments thereof. The invention additionally provides isolated capsid protein derived from the FCV strains of the invention or specific immunogenic fragments thereof.

For FCV strains, a good immune response is induced by antigenic determinant arising from the capsid protein. Here we describe and claim several strains of FCV including closely related capsid proteins and variants thereof. Specifically, we describe strain FCV-21 and protein sequence (SEQ ID 13) and sequences having 91.2%, 95% and 99% or more identity; strain FCV-49 and protein sequence (SEQ ID 15) and sequences having 92.7%, 95% and 99% or more identity; strain FCV-26391-4 and protein sequence (SEQ ID 17) and sequences having 91.8%, 95% and 99% or more identity.

The vaccine of the present invention is generally intended to be a prophylactic treatment which immunizes cats against disease caused by virulent strains of feline calicivirus. However, the vaccine is also intended for the therapeutic treatment of cats already infected with a virulent strain of feline calicivirus. For example, a vaccine comprising antibodies produced by immunizing a heterologous host with FCV capsid or immunogenic component thereof, is used for the therapeutic treatment of a feline calicivirus-infected cat.

However, even vaccines that provide active immunity, i.e., vaccines comprising FCV strains selected from the group consisting of FCV-21, FCV-49 and FCV 26391-4, or mutants thereof, or capsid proteins derived from the FCV strains of the invention, or a specific immunogenic fragments of their capsid proteins, would be expected to be effective when given as a therapeutic treatment against various diseases. Thus, the immunity that is provided by the present invention can be either active immunity or passive immunity, and the intended use of the vaccine can be either prophylactic or therapeutic.

The route of administration for any one of the embodiments of the vaccine of the present invention includes, but is not limited to, oronasal, intramuscular, intraperitoneal, intradermal, subcutaneous, intravenous, intraarterial, intraocular, and oral as well as transdermal or by inhalation or suppository. The preferred routes of administration include oronasal, intramuscular, intraperitoneal, intradermal, and subcutaneous injection. The vaccine can be administered by any means that includes, but is not limited to, syringes, nebulizers, misters, needleless injection devices, or microprojectile bombardment gene guns (Biolistic bombardment).

The vaccine for any one of the embodiments of the present invention is formulated in a pharmaceutically accepted carrier according to the mode of administration to be used. One skilled in the art can readily formulate a vaccine that comprises a live or killed FCV-21, FCV-49 or FCV 26391-4, a capsid protein derived from any of the FCV strains of the invention, or an immunogenic fragment thereof, a recombinant virus vector encoding the FCV-21, FCV-49 or FCV 26391-4 capsid protein or a specific immunogenic fragment thereof, or a DNA molecule encoding the FCV-21, FCV-49 or FCV 26391-4 derived capsid protein or a specific immunogenic fragment thereof. In cases where intramuscular injection is preferred, an isotonic formulation is preferred. Generally, additives for isotonicity can include sodium chloride, dextrose, mannitol, sorbitol, and lactose. In particular cases, isotonic solutions such as phosphate buffered saline are preferred. The formulations can further provide stabilizers such as gelatin and albumin. In some embodiments, a vaso-constrictive agent is added to the formulation. The pharmaceutical preparations according to the present invention are provided sterile and pyrogen-free. However, it is well known by those skilled in the art that the preferred formulations for the pharmaceutically accepted carrier which comprise the vaccines of the present invention are those pharmaceutical carriers approved in the regulations promulgated by the United States Department of Agriculture, or equivalent government agency in a foreign country such as Canada or Mexico or any one of the European nations, for live feline calicivirus vaccines, killed feline calicivirus vaccines, polypeptide (antigen) subunit vaccines, recombinant virus vector vaccines, antibody vaccines, and DNA vaccines. Therefore, the pharmaceutically accepted carrier for commercial production of the vaccine of the present invention is a carrier that is already approved or will be approved by the appropriate government agency in the United States of America or foreign country. The vaccine can further be mixed with an adjuvant that is pharmaceutically acceptable. In certain formulations of the vaccine of the present invention, the vaccine is combined with other feline vaccines to produce a polyvalent vaccine product that can protect cats against a wide variety of diseases caused by other feline pathogens. Currently, commercial manufacturers of feline vaccines, as well as end users prefer polyvalent vaccine products. Therefore, in a preferred embodiment, the present invention provides a polyvalent vaccine which immunizes cats against feline calicivirus and at least one other feline pathogen, preferably selected from the group consisting of feline herpesvirus, feline leukemia virus, feline immunodeficiency virus, feline *Chlamydia*, and feline panleukopenia virus.

Inoculation of a cat is preferably by a single vaccination that produces a full, broad immunogenic response. In another embodiment of the present invention, the cat is subjected to a series of vaccinations to produce a full, broad immune response. When the vaccinations are provided in a series, the vaccinations can be provided between about one day to four weeks or longer apart. In particular embodiments, the cat is vaccinated at different sites simultaneously. Additional details about the route and administration are found below in the section titled "Methods of Immunizing Cats against Calicivirus."

The vaccine compositions optionally may include vaccine-compatible pharmaceutically acceptable (i.e., sterile and non-toxic) liquid, semisolid, or solid diluents that serve as pharmaceutical vehicles, excipients, or media. Diluents can include water, saline, dextrose, ethanol, glycerol, and the like. Isotonic agents can include sodium chloride, dextrose, mannitol, sorbitol, and lactose, among others. Stabilizers include albumin, among others. Any adjuvant known in the art may be used in the vaccine composition, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, Pluronic® polyols. Adjuvants include, but are not limited to, the RIBI adjuvant system (Ribi Inc.), alum, aluminum hydroxide gel, cholesterol, oil-in water emulsions, water-in-oil emulsions such as, e.g., Freund's complete and incomplete adjuvants, Block co-polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from E. coli (recombinant or otherwise), cholera toxin, or muramyl dipeptide, among many others. The immunogenic compositions can further include one or more other immunomodulatory agents such as, e.g., interleukins, interferons, or other cytokines. The immunogenic compositions can also include gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 500 µg/2 ml dose of the vaccine composition. In another preferred embodiment, the present invention contemplates vaccine compositions comprising from about 1 µg/ml to about 60 µg/ml of antibiotic, and more preferably less than about 30 µg/ml of antibiotic.

The immunogenic compositions of the present invention can be made in various forms depending upon the route of administration. For example, the immunogenic compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g., saline or/and HEPES, with or without adjuvant.

In addition, the immunogenic and vaccine compositions of the present invention can include one or more pharmaceutically-acceptable carriers. As used herein, "a pharmaceutically-acceptable carrier" includes any and all solvents, dispersion media, coatings, adjuvants, stabilizing agents, diluents, preservatives, antibacterial and antifungal agents, isotonic agents, adsorption delaying agents, and the like. The carrier(s) must be "acceptable" in the sense of being compatible with the components of the invention and not deleterious to the subject to be immunized. Typically, the carriers will be will be sterile and pyrogen-free.

Live Vaccines

In one embodiment of the vaccine of the present invention, the vaccine comprises a live FCV vaccine, wherein the FCV component is selected from the group consisting of FCV-21, FCV-49 and FCV 26391-4. Because these strains were isolated in a non-virulent form they are particularly preferred for the preparation of a live vaccine which stimulates the cat's immune system without causing disease.

Methods for attenuating the viruses further are well known in the art and include such methods as serial passage in cell culture on a suitable cell line, or ultraviolet or chemical mutagenesis.

Inactivated Vaccines

In another embodiment of the present invention, the vaccine comprises an inactivated or killed FCV vaccine comprising an FCV strain selected from the group consisting of FCV-21, FCV-49 and FCV 26391-4. The inactivated vaccine is made by methods well known in the art. For example, once the virus is propagated to high titers, it would be readily apparent by those skilled in the art that the virus antigenic mass could be obtained by methods well known in the art. For example, the virus antigenic mass may be obtained by dilution, concentration, or extraction. All of these methods have been employed to obtain appropriate viral antigenic mass to produce vaccines. The calicivirus is inactivated by treatment with formalin, betapropriolactone (BPL), or with binary ethyleneimine (BEI), or other methods known to those skilled in the art.

Inactivation by formalin is performed by mixing the calicivirus suspension with 37% formaldehyde to a final formaldehyde concentration of 0.05%. The calicivirus-formaldehyde mixture is mixed by constant stirring for approximately 24 hours at room temperature. The inactivated calicivirus mixture is then tested for residual live virus by assaying for growth on a suitable feline cell line such as CRFK cells.

Inactivation by BEI is performed by mixing the calicivirus suspension of the present invention with 0.1 M BEI (2-bromo-ethylamine in 0.175 N NaOH) to a final BEI concentration of 1 mM. The calicivirus-BEI mixture is mixed by constant stirring for approximately 48 hours at room temperature, followed by the addition of 1.0 M sodium thiosulfate to a final concentration of 0.1 mM. Mixing is continued for an additional two hours. The inactivated calicivirus mixture is tested for residual live calicivirus by assaying for growth on a suitable feline cell line such as NLFK cells.

The aforementioned inactivated calicivirus of the present invention is mixed with any one of the pharmaceutically carriers for formulating inactivated virus vaccines to the appropriate dosage level. The inactivated vaccine further can include, in addition to an FCV component selected from the group consisting of FCV-21, FCV-49 and FCV 26391-4 at least one other feline calicivirus strain, preferably selected from the group consisting of FCV-F9, FCV-M8, FCV-255, and FCV-2280. In a preferred embodiment, the vaccine further includes a vaccine for immunizing a cat against one or more other feline pathogens, preferably selected from the group consisting of feline herpesvirus, feline leukemia virus, feline immunodeficiency virus, feline Chlamydia, and feline panleukopenia virus.

Recombinant Vaccines

In a further embodiment of the present invention, the vaccine comprises a recombinant virus vector containing a nucleic acid encoding an FCV capsid protein disclosed herein or a specific immunogenic fragment thereof.

In one particular embodiment, the recombinant virus vector is a feline herpesvirus that immunizes a cat against both feline calicivirus and feline herpesvirus. In another embodiment, the recombinant virus vector comprises one or more antigens preferably selected from the group consisting of feline herpesvirus, feline leukemia virus, feline immunodeficiency virus, feline Chlamydia, and feline panleukopenia virus, rabies virus and Bordetella bronchiseptica.

To make a recombinant virus vector that expresses the an FCV capsid protein or a specific immunogenic fragment thereof, a cDNA encoding the capsid protein or a specific immunogenic fragment thereof is inserted into the genome of a virus vector such as herpesvirus, poxvirus, or adenovirus. U.S. Pat. No. 5,716,822 to Wardley et al. describes a method for inserting DNA encoding the feline calicivirus strain CFI-68 FIV capsid protein into the feline herpesvirus thymidine kinase gene. Other recombinant virus vector vaccines embraced by the present invention, include but are not limited to, adenovirus, adeno-associated virus, parvovirus, and various poxvirus vectors to express the FCV capsid protein or a specific immunogenic fragment thereof. In particular, the present invention includes recombinant poxvirus vector vaccines that express the FCV capsid protein or a specific immunogenic fragment thereof made according to the methods taught in any one of U.S. Pat. Nos. 5,338,683 and 5,494,807 to Paoletti et al., which teach recombinant virus vaccines consisting of either vaccinia virus or canary poxvirus expressing foreign antigens; U.S. Pat. No. 5,266,313 to Esposito et al., which teaches recombinant raccoon poxvirus vectors expressing rabies virus antigens; and U.S. Pat. No. 6,010,703 to Maes et al., which teaches recombinant racoon poxvirus vectors that express the feline herpesvirus gD or gB antigens.

For any of the aforementioned recombinant virus vectors, the cDNA encoding the FCV capsid protein or a specific immunogenic fragment thereof is operably linked to a eukaryote promoter at the 5' end of the cDNA encoding the antigen and a eukaryote termination signal and poly (A) signal at the 3' end of the cDNA encoding the antigen. As used herein, the term "operably linked" means that the polynucleotide of the present invention (as a cDNA molecule) and a polynucleotide (DNA) containing an expression control sequence, e.g., transcription promoter and termination sequences, are situated in a vector or cell such that expression of the antigen encoded by the cDNA is regulated by the expression control sequence. Methods for cloning DNA such as the cDNA encoding the FCV capsid protein or a specific immunogenic fragment thereof and operably linking DNA containing expression control sequences thereto are well known in the art. Examples of promoters suitable for expressing the FCV capsid protein or a specific immunogenic fragment thereof in the recombinant virus vectors are the cytomegalovirus immediate-early (CMV) promoter, the Rous sarcoma virus long terminal repeat (RSV-LTR) promoter, the simian virus 40 (SV40) immediate-early promoter, and inducible promoters such as the metallothionein promoter. An example of a DNA having a termination and poly (A) signal is the SV40 late poly (A) region. Another example of a viral expression system suitable for producing the antigen is the Sindbis Expression system available from Invitrogen. The use of these commercially available expression vectors and systems are well known in the art.

Nucleic Acid or DNA Molecule Vaccine

In an embodiment further still of the present invention, the vaccine is provided as a nucleic acid or DNA molecule vaccine that elicits an active immune response in the cat. The DNA molecule vaccine consists of DNA having a nucleic acid sequence which encodes the capsid protein or a specific immunogenic fragment thereof of a FCV-capsid protein disclosed herein.

In a preferred embodiment, the DNA molecule vaccine comprises the nucleic acid sequence of SEQ ID NOS: 12, 14, or 16, or a fragment thereof encoding SEQ ID NOS: 13, 15 or 17, or a specific immunogenic fragment of SEQ ID NOS: 13, 15 or 17. The nucleic acid encoding the capsid protein or a specific immunogenic fragment thereof is operably linked at or near a transcriptional promoter. This enables transcription of the capsid protein, or a specific immunogenic fragment thereof, from the nucleic acid when the nucleic acid is inoculated into the cells of the cat. Preferably, the DNA molecule is a plasmid. Promoters that are useful for DNA vaccines are well known in the art and include, but are not limited to, the RSV LTR promoter, the CMV immediate early promoter, and the SV40 T antigen promoter. It is further preferred that the nucleic acid be operably linked, at or near the termination codon of the sequence encoding the capsid protein or a specific immunogenic fragment thereof, to a nucleic acid fragment comprising a transcription termination signal and poly (A) recognition signal. The DNA vaccine is provided to the cat in an accepted pharmaceutical carrier or in a lipid or liposome carrier similar to those disclosed in U.S. Pat. No. 5,703,055 to Felgner. The DNA vaccine can be provided to the cat by a variety of methods such as intramuscular injection, intrajet injection, or biolistic bombardment. Making DNA vaccines and methods for their use are provided in U.S. Pat. Nos. 5,589,466 and 5,580,859, both to Felgner. Finally, a method for producing pharmaceutical grade plasmid DNA is taught in U.S. Pat. No. 5,561,064 to Marquet et al.

Therefore, using the abovementioned methods, DNA vaccines that express the FCV capsid protein or a specific immunogenic fragment thereof are used to immunize cats against virulent feline calicivirus. The advantage of the DNA vaccine is that the DNA molecule is conveniently propagated as a plasmid which is a simple and inexpensive means for producing a vaccine, and since the vaccine is not live, many of the regulatory issues associated with live recombinant virus vector vaccines are not an issue with DNA vaccines. One skilled in the art would appreciate that the DNA vaccine of the present invention can comprise synthetically produced nucleic acids that are made by chemical synthesis methods well known in the art.

Isolated and Purified FCV Capsid Protein

In an embodiment further still of the present invention, the vaccine consists of the isolated and purified FCV capsid protein or a specific immunogenic fragment thereof. In particular, a vaccine wherein the FCV capsid protein or a specific immunogenic fragment thereof comprises the amino acid sequence of SEQ ID NO:13, 15, 17. Preferably, the capsid protein or a specific immunogenic fragment thereof is produced in a recombinant bacterium or eukaryote expression vector that produces the antigen that can be isolated and purified to make the vaccine. For example, the FCV capsid protein or a specific immunogenic fragment thereof is produced in a microorganism such as bacteria, yeast, or fungi, in a eukaryote cell such as a mammalian or an insect cell, or via a recombinant virus vector such as adenovirus, poxvirus, herpesvirus, Semliki Forest virus, baculovirus, bacteriophage, Sindbis virus, or Sendai virus. Suitable bacteria for producing the FCV capsid protein or a specific immunogenic fragment thereof include *Escherichia coli, Bacillus subtilis*, or any other bacterium that is capable of expressing heterologous polypeptides. Suitable yeast types for expressing the FCV capsid protein or a specific immunogenic fragment thereof include *Saccharomyces cerevisiae, Schizosaccharomyces pombe, Candida*, or any other yeast capable of expressing heterologous polypeptides. Methods for using the aforementioned bacteria, eukaryotic cells or recombinant virus vectors to produce antigens for vaccines are well known in the art.

To produce the vaccine consisting of the capsid protein or a specific immunogenic fragment thereof, the nucleic acid encoding the FCV capsid protein or a specific immunogenic fragment thereof is cloned into a plasmid, and the nucleic acid is operably linked to a promoter which effects the expression of the capsid protein or a specific immunogenic fragment thereof in a microorganism. Suitable promoters include, but are not limited to, T7 phage promoter, T3 phage promoter, β-galactosidase promoter, and the Sp6 phage promoter. Expression of the FCV capsid protein or a specific immunogenic fragment thereof in a microorganism enables the capsid protein to be produced using fermentation technologies that are used commercially for producing large quantities of recombinant antigenic polypeptides. Methods for isolating and purifying antigens are well known in the art and include methods such as gel filtration, affinity chromatography, ion exchange chromatography, or centrifugation.

To facilitate isolation of the FCV capsid protein or a specific immunogenic fragment thereof, a fusion polypeptide is made wherein the capsid protein or a specific immunogenic fragment thereof is linked to another polypeptide which enables isolation by affinity chromatography. Preferably, a fusion polypeptide is made using one of the expression systems infra. For example, the cDNA nucleic acid sequence encoding the FCV capsid protein or a specific immunogenic fragment thereof is linked at either the 5' end or 3' end to a nucleic acid encoding a polypeptide. The nucleic acids are linked in the proper codon reading frame to enable production of a fusion polypeptide wherein the amino and/or carboxyl terminus of the capsid protein or portion thereof is fused to a polypeptide which allows for the simplified recovery of the antigen as a fusion polypeptide. The fusion polypeptide can also prevent the antigen from being degraded during purification. While a vaccine comprising the fusion polypeptide is efficacious, in some instances it can be desirable to remove the second polypeptide after purification. Therefore, it is also contemplated that the fusion polypeptide contains a cleavage site at the junction between the antigen and the polypeptide. The cleavage site consists of an amino acid sequence that is cleaved with an enzyme specific for the amino acid sequence at the site. Examples of such cleavage sites that are contemplated include the enterokinase cleavage site which is cleaved by enterokinase, the factor Xa cleavage site which is cleaved by factor Xa, and the GENENASE cleavage site which is cleaved by GENENASE (GENENASE is a trademark of New England Biolabs, Beverly, Mass.). The following are methods for producing the capsid protein or a specific immunogenic fragment thereof as a fusion polypeptide or as an isolated antigen free of the polypeptide.

An example of a procaryote expression system for producing the FCV capsid protein or a specific immunogenic fragment thereof as a fusion polypeptide for use in vaccines is the Glutathione S-transferase (GST) Gene Fusion System available from Amersham Pharmacia Biotech, Piscataway, N.J., which uses the pGEX-4T-1 expression vector plasmid. The cDNA encoding the capsid protein or a specific immunogenic fragment thereof is fused in the proper codon reading frame with the DNA encoding GST. The GST part of the fusion polypeptide allows the rapid purification of the fusion polypeptide using glutathione Sepharose 4B affinity chromatography. After purification, the GST portion of the fusion polypeptide can be removed by cleavage with a site-specific protease such as thrombin or factor Xa to produce an antigen free of the GST polypeptide. The capsid protein or a specific immunogenic fragment thereof, free of the GST polypeptide, is produced by a second round of glutathione Sepharose 4B affinity chromatography.

Another method for producing a vaccine comprising the FCV capsid protein or a specific immunogenic fragment thereof is a method which links in-frame the cDNA encoding the antigen and DNA codons that encode polyhistidine. The polyhistidine preferably comprises six histidine residues which allows purification of the fusion polypeptide by metal affinity chromatography, preferably nickel affinity chromatography. To produce the capsid protein or a specific immunogenic fragment thereof free of the polyhistidine, a cleavage site such as an enterokinase cleavage site is fused in the proper reading frame between the codons encoding the polyhistidine and the codons encoding the antigen. The antigen is freed of the polyhistidine by cleavage with enterokinase, followed by a second round of metal affinity chromatography which binds the free polyhistidine. This method was shown to be useful for preparing the LcrV antigen of *Y. pestis*, which was disclosed in Motin et al. (Infect. Immun. 64: 4313-4318 (1996)). The Xpress System, available from Invitrogen, Carlsbad, Calif., is an example of a commercial kit that is available for making and then isolating polyhistidine-polypeptide fusion protein.

A method further still for producing a vaccine comprising the FCV capsid protein or a specific immunogenic fragment thereof uses a method disclosed by Motin et al., Infect. Immun. 64: 3021-3029 (1995). Motin et al. disclosed a DNA encoding a fusion polypeptide consisting of the DNA encoding an antigen linked to DNA encoding a portion of protein A wherein DNA encoding an enterokinase cleavage site is interposed in the proper codon reading frame between the DNA encoding protein A and the antigen. The protein A enables the fusion polypeptide to be isolated by IgG affinity chromatography, and the capsid protein free of the protein A is produced by cleavage with enterokinase. The protein A is then removed by a second round of IgG affinity chromatography.

Another method for producing a vaccine comprising the FCV capsid protein or a specific immunogenic fragment thereof is based on methods disclosed in U.S. Pat. No. 5,725,863 to Daniels et al, which is incorporated herein by reference in its entirety. Daniels et al. method can be used to make the FCV capsid vaccine which consists of enterotoxin molecule wherein each molecule has inserted therein upwards of 100 amino acid residues of the FCV capsid protein. Other methods for making fusion polypeptide vaccines which can be used to make the vaccines of the present invention is disclosed in U.S. Pat. No. 5,585,100 to Mond et al. and U.S. Pat. No. 5,589,384 to Liscombe. Finally, the pMAL Fusion and Purification System available from New England Biolabs is another example of a method for making a fusion polypeptide wherein a maltose binding protein is fused to the capsid protein or a specific immunogenic fragment thereof. The maltose binding protein facilitates isolation of the fusion polypeptide by amylose affinity chromatography. The maltose binding protein can be linked to the antigen by one of the above mentioned cleavage sites which enables the antigen to be made free of the maltose binding protein.

While bacterial methods are used to produce the FCV capsid protein or a specific immunogenic fragment thereof for vaccines, it can be desirable to produce the capsid protein or a specific immunogenic fragment thereof in a eukaryote expression system. A particularly useful system is the baculovirus expression system that is disclosed in U.S. Pat. No. 5,229,293 to Matsuura et al., which is incorporated herein by reference in its entirety. Baculovirus expression vectors suitable to produce the capsid protein or a specific immunogenic fragment thereof are the pPbac and pMbac vectors from Stratagene; and the Bac-N-Blue vector, the pBlueBac4.5 vector, pBlueBacHis2-A,B,C, and the pMelBac available from Invitrogen, Carlsbad, Calif.

Another eukaryote system useful for expressing the FCV capsid protein or a specific immunogenic fragment thereof for vaccines is a yeast expression system such as the ESP Yeast Protein Expression and Purification System available from Stratagene. Another yeast expression system is any one of the Pichia-based expression systems from Invitrogen. Mammalian expression systems are also embraced by the present invention. Examples of mammalian expression systems are the LacSwitch II system, the pBK Phagemid, pXT1 vector system, and the pSG5 vector system from Stratagene; the pTargeT mammalian expression vector system, the pSI mammalian expression vector, pCI mammalian expression vector, and pAdVantage vectors available from Promega Corporation, Madison, Wis.; and the Ecdysone-Inducible Mammalian Expression System, pCDM8, pcDNA1.1, and pcDNA1.1/Amp available from Invitrogen.

The present invention further includes an embodiment consisting of vaccines that comprise the FCV capsid protein or particular epitopes of the capsid protein as components of a heat-stable spore delivery system made according to the method taught in U.S. Pat. No. 5,800,821 to Acheson et al., which is incorporated herein by reference in its entirety. Therefore, the present invention provides a genetically engineered bacterial cell containing a nucleic acid encoding the FCV capsid protein or a specific immunogenic fragment thereof. When the recombinant bacterial spore vaccine is orally administered to the cat, the spores germinate in the gastrointestinal tract of the cat and the bacteria expresses the capsid protein or a specific immunogenic fragment thereof which comes into contact with the cat's immune system and elicits an immune response. The vaccine has the advantage of being heat stable; therefore, it can be stored at room temperature for an indefinite period of time.

Passive Immunity Vaccines

While the above embodiments of the present invention provide active immunity against feline calicivirus, the present invention further comprises vaccines that provide passive immunity to feline calicivirus. A vaccine that elicits passive immunity against feline calicivirus consists of polyclonal antibodies or monoclonal antibodies that are against the FCV capsid protein, a specific immunogenic fragment thereof, or the whole FCV virus.

To make a passive immunity vaccine comprising polyclonal antibodies, the FCV capsid protein thereof, or a specific immunogenic fragment thereof is injected into a suitable host for preparing the antibodies, preferably the host is a horse, swine, rabbit, sheep, or goat. Methods for producing polyclonal antibody vaccines from these hosts are well known in the art. By way of example, the capsid protein or a specific immunogenic fragment thereof or whole calicivirus FCV capsid is mixed with an adjuvant such as Freund's complete or the less toxic TiterMax available from CytRx Corp., Norcross, Ga., which then administered to the host by methods well known in the art. Antibody production is monitored and when sufficient antibody has been produced, the serum is removed from the host and preferably the antibody is recovered from the serum.

The passive immunity vaccine can comprise one or more monoclonal antibodies against one or more epitopes of the FCV capsid protein or whole FCV virus. Methods and hybridomas for producing monoclonal antibodies are well known in the art. While monoclonal antibodies can be made using hybridoma technologies well known in the art, the monoclonal antibodies against the antigen can also be made according to phage display methods such as that disclosed in U.S. Pat. No. 5,977,322 to Marks et al., which is incorporated herein by reference in its entirety. Felinized antibodies against the capsid protein or portion thereof can be made according to methods which have been used for humanizing antibodies such as those disclosed in U.S. Pat. Nos. 5,693,762 and 5,693,761 both to Queen et al., which is incorporated herein by reference in its entirety. A phage display kit that is useful for making monoclonal antibodies is the Recombinant Phage Antibody System available from Amersham Pharmacia Biotech.

Antibodies, Polyclonal and Monoclonal

This invention also comprises, describes and claims several very important monoclonal antibodies. These antibodies have been developed here in order to rapidly identify and in some cases define the viral strains described herein. Particular examples of monoclonal antibodies and their descriptions can be found in the following examples. In particular see EXAMPLE 1-2 and TABLE 1-2, and especially EXAMPLE 1-8, TABLE 1-4.

The following examples are intended to promote but not limit a further understanding of the present invention

PART 1 EXAMPLES

Example 1-1

Isolation and Growth of FCV-21

Feline calicivirus (FCV) strain 21 (FCV-21) was collected in June of 1993 from an Ann Arbor, Mich. cat show. It was diluted in 96 well micro-tubes containing 1% media and 1:10 dilutions were made. 100 ul of the diluted sample was added to 100 ul of CRFK cells in a 96 well plate.

The FCV-21 virus was purified three times by limited dilution in 96 well plates. The viral supernatant from the final purification was removed and used to infect CRFK cells grown to 75% confluence in a T25 flask. When 100% CPE was observed, the suspension was freeze/thawed three times and aliquoted into freezing vials (1 ml/vial). The titer of this viral stock was determined to be $1.5 \times 10^8$ TCID$_{50}$/ml.

FCV-21 was deposited on Feb. 1, 2006 with the American Type Culture Collection (ATCC), 10801 University Blvd., Manassas, Va., 20110, USA, and assigned ATCC accession number PTA-7346.

Example 1-2

Immunofluorescence and ELISA of FCV-21 Using Various Commercial or Pre-Existing Monoclonal Antibodies For the immunofluorescense assay (IFA), a viral stock of FCV-21 was used to infect a 24-well plate seeded with NLFK cells grown to approximately 90% confluency. At approximately 20 hours post infection, the plate was washed twice with 1×PBS, and fixed with 80% acetone. Various monoclonal antibodies were diluted to about 2 ug/ul and added to individual wells of the plate (0.2 ml/well). After a 1 hr incubation at room temperature (RT) with agitation, each well was washed twice with 1×PBS, and secondary antibody (anti-mouse FITC, 10 ug/ml) was added. After covering the plate with aluminum foil and incubating for 30 min at RT with agitation, each well was washed twice with 1×PBS, and air dried. Each well was then observed under a fluorescence microscope for its intensity of staining with FITC.

For the ELISA assay, a 96-well ELISA plate was coated with 200 ul of an anti-FCV rabbit polyclonal antibody (Pfizer #16), diluted 1:1500 in sodium carbonate buffer (1.59 g of $Na_2CO_3$ and 2.93 g of $NaHCO_3$ dissolved into 1 liter of water). The plate was incubated at 4° C. overnight. The plate was washed three times with 1×PBS (pH 7.4) containing 0.05% of Tween-20 (PBST), then blocked with 200 ul of 1% Casein in PBST for 1 hour at 37° C. Various monoclonal antibodies were diluted to about 0.1 ug/ml and added to individual wells (100 ul/well). Each sample was done in triplicate. After incubation at 37° C. for 1 hr, each well was washed 3 times with PBST, and incubated with 100 ul of 1:200 diluted peroxidase-conjugated AffiniPure Goat anti-Mouse IgG (H+L) (Jackson ImmunoResearch, cat. No. 715-035-150) for 1 hour at 37° C. Each well was then washed 3 times with PBST, followed by the addition of 100 ul of ABTS peroxidase substrate (KPL, Gaithersburg, Md., cat. No. 50-66-18) to each well. After approximately 10 min at RT, the plate was read at 405-490 nm (dual wavelength) with a ELISA reader. Specific activity was calculated based on the signal/noise ratio.

The data sets from the IFA and ELISA assays correlated well with each other (TABLE 1-2), and indicated that FCV-21 is immunologically distinct from F9, a commonly used FCV vaccine strain. Two monoclonal antibodies (FCV 1-43 and MAB791P) reacted with F9, but not with FCV-21 (TABLE 1-2).

TABLE 1-2

SUMMARY OF AFFINITIES OF VARIOUS MONOCLONAL ANTIBODIES FOR FCV STRAINS F9 AND FCV-21

| | | Catalogue/ID | IFA | | ELISA | |
|---|---|---|---|---|---|---|
| | Source | No. | F9 | FCV-21 | F9 | FCV-21 |
| 1 | Accurate Chemical | YVS7401 | +++ | ++ | 17 | 16 |
| 2 | Accurate Chemical | YVS7402 | − | − | 1 | 1 |
| 3 | Accurate Chemical | MEDCLA309 | ++++ | ++++ | 8 | 3 |
| 4 | Chemicon | MAB8962 | ++ | ++ | 23 | 24 |
| 5 | Cortex Biochem | CR1260M | + | + | 11 | 12 |
| 6 | Custom Monoclonals, Int. | S1-9 | +++ | +++ | 27 | 24 |
| 7 | Custom Monoclonals, Int. | FCV 1-43 | +++ | − | 5 | 1 |
| 8 | Custom Monoclonals, Int. | FCV8-1A | +++ | +++ | 5 | 13 |
| 9 | Maine Biotech | MAB790P | ++++ | ++++ | 26 | 26 |
| 10 | Maine Biotech | MAB791P | +++ | − | 4 | 1 |
| 11 | Novocastra Lab | NCL-1G9 | +++ | +++ | 17 | 5 |
| 12 | In-house (Pfizer) | 1-4 mAb | − | − | 1 | 1 |
| 13 | In-house (Pfizer) | 1-12 mAb | ++++ | +++ | 12 | 1 |
| 14 | In-house (Pfizer) | 3-3 mAb | ++++ | ++++ | 22 | 25 |
| 15 | In-house (Pfizer) | 3-5 mAb | ++++ | ++++ | 21 | 22 |
| 16 | In-house (Pfizer) | rabbit serum | ++++ | ++++ | | |
| 17 | Biocor/Pfizer | S1.9A1A | ++++ | ++++ | 29 | 33 |

Example 1-3

Capsid Sequence Analysis of FCV-21

Total RNA was isolated from the supernatant of a FCV-21-infected cell culture using TRIzol reagent (Invitrogen; Carlsbad, Calif.). A "first strand" cDNA preparation was synthesized using random primers and Superscript II reverse transcriptase (Invitrogen). The PCR reaction was performed using the XL rTth polymerase (Applied Biosystems; Foster City, Calif.) and oligonucleotide primers DEL-653 (SEQ ID NO. 1) and DEL-651 (SEQ ID NO. 2). The resulting PCR product was sequenced using BigDye chemistry and an ABI377 Genetic Analyzer. The complete capsid sequence is listed as SEQ ID NO. 12 for nucleotide sequence and SEQ ID NO. 13 for encoded amino acid sequence.

Example 1-4

Isolation and Growth of FCV-49

Feline calicivirus (FCV) strain 49 (FCV-49, also called PHA-49) was collected in 1993 from a Philadelphia, Pa. cat show. The specimen was diluted in 96 well micro-tubes containing 1% media, and 1:10 dilutions were made. 100 ul of the diluted sample was added to 100 ul of CRFK cells in a 96 well plate. The FCV-49 virus was purified three times by limited dilution in 96 well plates. The viral supernatant from the final purification was removed and used to infect CRFK cells grown to 75% confluence in a T25 flask. When 100% CPE was observed, the suspension was freeze/thawed three times and aliquoted into freezing vials (1 ml/vial). The titer of this viral stock was determined to be 6.8×10⁷ TCID50/ml.

FCV-49 was deposited on Feb. 1, 2006 with the American Type Culture Collection (ATCC), 10801 University Blvd., Manassas, Va., 20110, USA, and assigned ATCC accession number PTA-7347.

Example 1-5

Capsid Sequence Analysis of FCV-49

Total RNA was isolated from the supernatant of a FCV-49-infected cell culture using TRIzol reagent (Invitrogen; Carlsbad, Calif.). A "first strand" cDNA preparation was synthesized using random primers and Superscript II reverse transcriptase (Invitrogen). The PCR reaction was performed using the XL rTth polymerase (Applied Biosystems; Foster City, Calif.) and oligonucleotide primers DEL-653 (SEQ ID NO:1) and DEL-651 (SEQ ID NO:2). The resulting PCR product was sequenced using BigDye chemistry and an ABI377 Genetic Analyzer. The complete capsid sequence is shown as SEQ ID NO. 14 for nucleotide sequence and SEQ ID NO. 15 for encoded amino acid sequence.

Example 1-6

Isolation and Growth of FCV-26391-4

Feline calicivirus (FCV) strain 26391-4 (FCV-26391-4) was collected in 2003 from the Humane Society of Bay County (Panama City, Fla.). It was purified once by limited dilution in a 96 well plate containing DMEM medium (Invitrogen) with 2% fetal bovine serum. The purified virus was then used to infect a T150 flask containing NLFK (Norden Lab Feline Kidney) cells. Once 100% CPE was reached, the suspension was freeze/thawed once and aliquoted into freezing vials (0.85 ml/vial). The viral titer of this stock was determined to be $5.6 \times 10^7$ TCID$_{50}$/ml.

FCV-26391-4 was deposited on Feb. 1, 2006 with the American Type Culture Collection (ATCC), 10801 University Blvd., Manassas, Va., 20110, USA, and assigned ATCC accession number PTA-7348.

Example 1-7

Capsid Sequence Analysis of FCV 26391-4

Total RNA was isolated from the supernatant of a FCV 26391-4 infected cell culture using a QIAamp Viral RNA Isolation Kit (Qiagen; Valencia, Calif.). Approximately 1 ug of viral RNA was used in RT-PCR (SuperScript One-Step RT-PCR with Platinum Taq; from Invitrogen). The reaction conditions were: 30 min at 50° C.; 2 min at 94° C.; followed by 40 cycles of 15 sec at 94° C., 30 sec at 55° C., and 2 min at 70° C.; followed by a final incubation at 72° C. for 10 min, and storage at 4° C. The primers used were FCV-N2 (SEQ ID NO. 3) and FCV-primer 2 (SEQ ID NO. 9). The PCR product was then sequenced using various oligonucleotide primers (SEQ ID NO. 3, 4, 5, 6, 7, 8, 9, 10, and 11). The sequence of the whole capsid for FCV 26391-4 is shown as SEQ ID NO. 16 for nucleotide sequence and SEQ ID NO. 17 for encoded amino acid sequence.

The amino acid sequences of the capsid genes from FCV-21, FCV-49 and FCV-26391-4 were aligned with all full-length FCV capsid sequences available in GenBank. The alignment was created using the ClustalW algorithm (Thompson et al 1994), the PAM250 weight matrix (Dayhoff et al., 1978), and default program parameters (MegAlign; DNASTAR, Inc; Madison, Wis.). The identity between the capsid protein sequences of FCV-21 and FCV 213-95, the highest among all entries in GenBank, is 90.7%. The FCV-49 and FCV 213-95 capsid sequences are 92.2% identical. The FCV 26391-4 and FCV CFI-68 capsid sequences are 91.3% identical to each other.

A single capsid sequence is presented for FCV-21, FCV-49, and FCV 26391-4, and is based upon direct sequencing of the PCR products obtained. However, each of these sequences represents the average, or consensus, sequence amongst a population of viral quasispecies, which are known to exist within RNA viral populations (for a review, see Domingo et al., Virus Res. 82:39-44; 2002). Quasispecies are a direct result of errors that occur during RNA genome replication, generating progeny which have mutations within their genome. Therefore, it is expected that minor variants of the capsid sequences for these and other FCV capsid gene sequences naturally exist. However, the distribution of mutations within each is such that they have little/no effect on the overall identity between strains, including FCV-21, FCV-49, and FCV 26391-4.

Examples 1-8

Generation of Monoclonal Antibodies Specific for FCV-21

A. Purification of FCV-21. About 200 ml of cell culture supernatant from NLFK cells infected with FCV-21, was centrifuged at 3,000 rpm for 30 minutes at 10° C. 25 ml of the supernatant was transferred into Beckman Ultraclear centrifuge tubes, and 10 ml of a 10% sucrose solution was underlayed into the bottom of the tube. The tubes were then centrifuged at 27,000 rpm for 2 hours at 15° C. Following centrifugation, supernatants were removed and discarded, and the pellets were resuspended in 250 ul of sterile water. The protein concentration was determined to be 7 mg/ml using the Micro BCA Protein Assay Kit (Pierce Chemical Co., Rockford, Ill.).

Immunization of Mice and Generation of Hybridoma Cell Clones

About 100 ug of purified FCV-21 virus protein was injected into each mouse together with Freund's adjuvant. Eight mice were vaccinated. Two boost immunizations were carried out with 100 ug purified FCV-21 with RIBI adjuvant at 4-week interval. Immune responses for those eight mice were determined to have titer of 31250 or above in ELISA using purified FCV-21. Cell fusion was carried out to create hybridoma clones. Sixty-eight of such cell clones were grown up and supernatant tested for its reactivity with FCV-21.

For this ELISA, a 96-well ELISA plate was coated with 100 ul of purified FCV at a concentration of 5 ug/ml, diluted in 1×PBS. The plate was dried at 37° C. overnight uncovered in a non-humidified incubator. The virus on plate was fixed by applying 0.1 ml of methanol and incubating at room temperature for 5 minutes. The plate was then washed 8 times with distilled water, then blocked with 200 ul of 10% house serum in 1×PBS for at 4° C. overnight. The plate was washed again for 8 times with distilled water. Various dilutions of mouse serum samples added to individual wells (100 ul/well). Each sample was done in triplicate. After incubation at 37° C. for 1 hr, each well was washed 3 times with PBST, and incubated with 100 ul of 1:200 diluted peroxidase-conjugated AffiniPure Goat anti-Mouse IgG (H+L) (Jackson ImmunoResearch, cat. No. 715-035-150) for 1 hour at 37° C. Each well was then washed 3 times with PBST, followed by the addition of 100 ul of ABTS peroxidase substrate (KPL, Gaithersburg, Md., cat. No. 50-66-18) to each well. After approximately 10 min at RT, the plate was read at 405-490 nm (dual wavelength) with a ELISA reader. Specific activity was calculated based on the signal/noise ratio.

Reactivity of FCV-21 Specific Monoclonal Antibodies

The supernatants of above hybridoma cell clones were used to test for its reactivity for FCV-21 as well as F9 in sandwich ELISA assay. Briefly, a 96-well ELISA plate was coated with 200 ul of an anti-FCV rabbit polyclonal antibody (Pfizer #16), diluted 1:1500 in sodium carbonate buffer (1.59 g of $Na_2CO_3$ and 2.93 g of $NaHCO_3$ dissolved into 1 liter of water). The plate was incubated at 4° C. overnight. The plate was washed three times with 1×PBS (pH 7.4) containing 0.05% of Tween-20 (PBST), then blocked with 200 ul of 1% Casein in PBST for 1 hour at 37° C. The FCV-21 and F-9 supernatants were added to each well at dilution of 1:10. After incubation at 37° C. for 1 hour, the plates were washed and various hybridoma supernatants and their various dilutions were added to individual wells (100 ul/well) in triplicate. The plates were then incubated at 37° C. for 1 hr, washed 3 times with PBST, and incubated with 100 ul of 1:200 diluted peroxidase-conjugated AffiniPure Goat anti-Mouse IgG (H+L) (Jackson ImmunoResearch, cat. No. 715-035-150) for 1 hour at 37° C. After washing, 100 ul of ABTS peroxidase substrate (KPL, Gaithersburg, Md., cat. No. 50-66-18) was added to each well. After approximately 10 min at RT, the plate was read at 405-490 nm (dual wavelength) with a ELISA reader. Specific activity was calculated based on the signal/noise ratio.

TABLE 1-3

ELISA SCREENING OF VARIOUS SUPERNATANTS OF HYBRIDOMA CELLS FOR THEIR SPECIFIC REACTIVITY FOR FCV-21 VS. F9.

| mAb\ | mAb undiluted | | 1:10 dilution of mAb | | 1:50 dilution of mAb | |
|---|---|---|---|---|---|---|
| Virus | PHA-21 | F9 | PHA-21 | F9 | PHA-21 | F9 |
| 1 sup | 30 | 1 | 3 | 1 | 2 | 1 |
| 2A sup | 2 | 1 | | | | |
| 2B sup | 3 | 1 | | | | |
| 3 sup | 29 | 3 | 21 | 1 | 16 | 1 |
| 4 sup | 1 | 1 | | | | |
| 5 sup | 1 | 1 | | | | |
| 6 sup | 1 | 1 | | | | |
| 7 sup | 26 | 3 | 22 | 1 | 17 | 1 |
| 8 sup | 9 | 8 | 3 | 1 | | |
| 9A sup | 1 | 1 | | | | |
| 9B sup | 1 | 1 | | | | |
| 10 sup | 15 | 13 | 10 | 6 | | |
| 11 sup | 1 | 1 | | | | |
| 13 sup | 27 | 22 | 19 | 14 | | |
| 14A sup | 2 | 2 | | | | |
| 14B sup | 5 | 3 | | | | |
| 15 sup | 1 | 1 | | | | |
| 16 sup | 21 | 2 | 5 | 1 | 2 | 1 |
| 17 sup | 20 | 1 | 14 | 1 | 12 | 1 |
| 18 sup | 27 | 22 | 25 | 11 | | |
| 20 sup | 1 | 1 | | | | |
| 21 sup | 17 | 9 | 7 | 2 | 2 | 1 |
| 22 sup | 2 | 1 | | | | |
| 23 sup | 12 | 1 | 10 | 1 | 10 | 1 |
| 24 sup | 14 | 14 | 1 | 1 | | |
| 26 sup | 1 | 1 | | | | |
| 27 sup | 15 | 7 | 8 | 3 | | |
| 28 sup | 1 | 2 | | | | |
| 29 sup | 24 | 8 | 23 | 1 | 29 | 1 |
| 30 sup | 17 | 7 | 13 | 1 | 18 | 1 |
| 31 sup | 19 | 19 | 16 | 11 | | |
| 32 sup | 28 | 16 | 21 | 12 | 18 | 10 |
| 33 sup | 20 | 17 | 15 | 13 | | |
| 34 sup | 20 | 18 | 15 | 13 | | |
| 35 sup | 14 | 12 | 9 | 6 | | |
| 36 sup | 17 | 5 | 15 | 1 | 21 | 1 |
| 37 sup | 12 | 4 | 3 | 1 | 1 | 1 |
| 38 sup | 6 | 5 | | | | |
| 39 sup | 23 | 15 | 17 | 6 | | |
| 40 sup | 16 | 3 | 10 | 1 | 13 | 1 |
| 41 sup | 19 | 7 | 14 | 1 | | |
| 42 sup | 13 | 1 | 15 | 1 | 17 | 1 |
| 43 sup | 1 | 1 | | | | |
| 44 sup | 9 | 4 | 4 | 1 | | |
| 45 sup | 1 | 1 | | | | |
| 46 sup | 8 | 4 | 3 | 2 | | |
| 47 sup | 4 | 3 | | | | |
| 48 sup | 11 | 11 | 5 | 4 | | |
| 49 sup | 12 | 13 | 8 | 7 | | |
| 50 sup | 1 | 1 | | | | |
| 51 sup | 2 | 2 | | | | |
| 52 sup | 4 | 10 | | | | |
| 53 sup | 12 | 2 | 10 | 1 | 3 | 1 |
| 54 sup | 1 | 1 | | | | |
| 55 sup | 19 | 18 | 25 | 15 | | |
| 56 sup | 8 | 4 | 6 | 1 | | |
| 57 sup | 1 | 1 | | | | |
| 58 sup | 2 | 8 | | | | |
| 59 sup | 18 | 1 | 20 | 1 | 16 | 1 |
| 60 sup | 31 | 1 | 35 | 1 | 21 | 1 |
| 61 sup | 18 | 4 | 33 | 1 | 29 | 1 |
| 62 sup | 1 | 1 | | | | |
| 63 sup | 1 | 1 | | | | |
| 64 sup | 1 | 1 | | | | |
| 65 sup | 3 | 5 | | | | |
| 66 sup | 4 | 5 | | | | |
| 67 sup | 21 | 12 | 22 | 3 | | |
| 69 sup | 1 | 1 | | | | |

B. Monoclonal antibodies specific for FCV-21 and not other FCV strains. Eighteen hybridoma cell clones (3, 7, 17, 23, 27, 29, 30, 36, 37, 40, 41, 42, 44, 53, 56, 59, 60 and 61) were chosen to be further tested for their specificity for FCV-21. Eleven FCV viruses were used in the assay (FCV-21, 49, 26391-4, F9, CFI-68, 33585, 89391, 255, J-1, 2280 and H). Again, sandwich ELISA was used, as described above. The results are summarized in TABLE 1-4.

TABLE 1-4

REACTIVITY OF MONOCLONAL SUPERNATANTS AGAINST VARIOUS FCV STRAINS

Yr of Isolation

| mAb\Virus | 1993 21 | 1993 49 | 2003 26391-4 | 1960 F9 | not known CFI-68 | 2000 33585 | 2000 89391 | 1970 255 | 1984 J-1 | 1983 2280 | 1990 H |
|---|---|---|---|---|---|---|---|---|---|---|---|
| 3 sup | 21 | 18 | 1 | 1 | 2 | 1 | .1 | 1 | 1 | 1 | 25 |
| 7 sup | 22 | 21 | 1 | 1 | 5 | 1 | 1 | 1 | 2 | 1 | 24 |
| 17 sup | 14 | 12 | 1 | 1 | 8 | 1 | 1 | 1 | 1 | 1 | 8 |
| 23 sup | 10 | 1 | 1 | 1 | 1 | 1 | 1 | 1 | 1 | 1 | 1 |
| 27 sup | 8 | 9 | 3 | 3 | 10 | 4 | 4 | 23 | 4 | 2 | 2 |
| 29 sup | 23 | 18 | 9 | 1 | 13 | 1 | 1 | 1 | 2 | 1 | 8 |
| 30 sup | 13 | 13 | 7 | 1 | 5 | 1 | 1 | 1 | 3 | 2 | 6 |
| 36 sup | 15 | 8 | 7 | 1 | 1 | 1 | 1 | 1 | 1 | 1 | 1 |
| 37 sup | 3 | 3 | 2 | 1 | 2 | 1 | 1 | 1 | 1 | 1 | 1 |
| 40 sup | 10 | 10 | 2 | 1 | 2 | 1 | 1 | 2 | 2 | 1 | 1 |
| 41 sup | 14 | 1 | 1 | 1 | 1 | 1 | 1 | 1 | 1 | 1 | 1 |
| 42 sup | 15 | 21 | 1 | 1 | 1 | 1 | 1 | 1 | 1 | 1 | 2 |
| 44 sup | 4 | 1 | 1 | 1 | 1 | 1 | 1 | 1 | 1 | 1 | 1 |
| 53 sup | 10 | 20 | 2 | 1 | 21 | 1 | 1 | 1 | 17 | 1 | 14 |
| 56 sup | 6 | 1 | 1 | 1 | 1 | 1 | 1 | 1 | 1 | 1 | 1 |
| 59 sup | 20 | 4 | 1 | 1 | 1 | 1 | 1 | 1 | 1 | 1 | 2 |
| 60 sup | 35 | 7 | 1 | 1 | 1 | 1 | 1 | 1 | 1 | 1 | 2 |
| 61 sup | 33 | 21 | 12 | 1 | 25 | 1 | 1 | 1 | 3 | 1 | 8 |

As demonstrated above, hybridoma cell lines 23, 41, 44 and 56 are specific for FCV-21, and not any other FCV tested. Therefore, those monoclonal antibodies can be used as a diagnostic tool for FCV-21. Moreover, hybridoma 36 seems to react with vaccine FCV strains only (FCV-21, 49, 26391-4) and not any other FCV strains.

Hybridoma cell lines 23, 36, 41, 44 and 56 were all deposited with the American Type Culture Collection (ATCC), 10801 University Blvd., Manassas, Va., 20110, USA, and assigned ATCC accession numbers:

PTA-7349 (Hybridoma 23)
PTA-7350 (Hybridoma 36)
PTA-7353 (Hybridoma 41)
PTA-7351 (Hybridoma 44)
PTA-7352 (Hybridoma 56)

Example 1-9

Serum Cross Neutralization Analysis of Sera of FCV-21 and FCV-49 Against FCV Viruses Isolated in 1993

A. Titration of homologous antiserum. Convalescent antiserum against twelve FCV isolates was raised in specific pathogen-free (SPF) cats, and collected after a primary and secondary inoculation. The virus inoculum varied according to stock titers, ranging from $10^4$ to $10^8$ $TCID_{50}$/cat. The cats were initially inoculated, boosted 3 weeks later, and then bled for serum 2 weeks post-boost. The twelve isolates included F9, CFI-68, LSO12, JOK63, JOK92, and field isolates 18, 21, 49, 50, 54, 27, and 11. The field isolates were selected based on a phylogenetic analysis of the sequences of the hypervariable region of each strain's capsid protein sequence. The most divergent isolates were chosen for the study.

Sera were heat inactivated at 56° C. for 30 minutes, and titered against their homologous virus using a standard constant virus—varying serum technique (Griest 1979, Mahy 1996). Briefly, media (100-150 µl) was added to each well of a 96 well tissue culture plate. Serum (100-150 µl) was added to each well of the top row (1:2 or 1:4 initial serum dilution; F9 and LSO12 at 1:4), and 100 µl were transferred down the plate after mixing (1:2 dilutions) with a multi-channel pipettor. The last 100 µl was discarded. 50 µl of titered homologous virus (diluted to 200 $TCID_{50}$/50 µl) was added to each well, and plates were incubated for 2 hrs at 37° C. in a $CO_2$ incubator. After incubation, 50 µl of a 1:10 dilution of CRFK cells in suspension was added to each well. A virus titer plate was set up using the diluted virus to ensure that an appropriate inoculum was added to each well. 50 µl of virus was used in the top row containing 150 µl of media; the rest of the plate contained 180 µl/well, and 10-fold dilutions were carried out down the plate with 20 µl. Plates were incubated for 4 days, and the Kärber formula was used to calculate both the serum and viral titers (in the case of serum titers, the proportion of protected wells to unprotected was used in the equation).

When titering the sera, the $TCID_{50}$ was defined as the 50% neutralizing endpoint dilution (Griest 1979). One antibody unit (AU) was defined as the highest dilution of that antiserum capable of neutralizing 32-320 $TCID_{50}$ of the homologous virus in 50% of the test cultures. Therefore, the $TCID_{50}$ obtained is equal to 1 AU. Virus cross-neutralizations were carried out against serum concentrations of 2.5, 5, 10 and 20 AU.

B. Virus cross-neutralization assay. Each viral field isolate, as well as strains F9, LSO12, JOK63, JOK92, SA113 and CFI-68, was tested against each of the twelve FCV antisera in a cross-neutralization assay. Each virus required five 96 well plates. Each serum was diluted to 2.5, 5, 10 and 20 AU and plated in replicates of eight down the plate (three sera/plate for a total of four plates), and a virus titer plate (set up in the same way as for serum titrations). Antisera dilutions were prepared in DMEM by first diluting the serum to 20 AU, and then carrying out 2-fold dilutions down to 2.5 AU. An aliquot of each dilution (100 µl) was then added to each column of wells on the plate. Viruses were quickly thawed at 37° C., placed on ice, and then diluted to 200 $TCID_{50}$/well (kept on ice). In order to maintain consistency, a three-step dilution process was used for most viral stocks, never going higher than a 1:100 in any step. Diluted virus stock (50 µl) was added to all wells of the serum plates and titered as previously described. Plates were incubated at 37° C. in a $CO_2$ incubator for 2 hr, after which 50 µl of 1:10 dilution of a CRFK cell suspension previously grown to confluency was added to each well. Pipette tips and reservoir troughs were changed after each set of five plates. Plates were scored after 4 days. In some cases, pre-titered, pre-diluted virus was used.

TABLE 1-5

SERUM CROSS-NEUTRALIZATION RESULTS

| serum virus | JOK63 2.5/5/10/20* | JOK92 2.5/5/10/20 | CFI68 2.5/5/10/20 | LSO12 2.5/5/10/20 | F9 2.5/5/10/20 | 11 2.5/5/10/20 |
|---|---|---|---|---|---|---|
| LSO12 | — — n n | — — — — | n N N N | n N N N | — N N N | — — — — |
| F9 | — — — — | — — — — | — — — n | — — — — | n N N | — — — — |
| JOK92 | — — — — | n N N | — — — — | — — — n | N N N | — — — — |
| CFI68 | — — — — | — — — — | N N N N | n N N N | N N N | — — — — |
| JOK63 | n n n N | — — — — | — — — — | — — — — | — n N n | — — — — |
| SA113 | — — — — | — — — — | — — n N | — — — — | N N N | — — — — |
| 3 | — — — — | — — — — | — — — — | — — — — | — | — — — — |
| 4 | — — — — | — — — — | — — — — | — — — — | — n N | — — — — |
| 6 | — — — — | — — — — | — — — — | — — — — | — | — — — — |
| 7 | — — — n | — — — — | — — — — | — — — n | N | — — — — |
| 8 | — — — — | — — — — | — — — — | — — — n | — | — — — — |
| 9 | — — — — | — — — — | — — — n | — — n — | N | — — — — |
| 10 | — — — — | — — — — | — — — — | — — — — | — — N | — — — — |
| 11 | — — — — | — — — — | — — — — | — — — — | — — — | n n n |
| 12 | — — — — | — — — — | — — — — | — — — n | — — n | — — — — |
| 13 | — — — — | — — — — | — — n n | — — — — | n N N | — — — — |
| 14 | — — — — | — — — — | — — — — | — — — — | — | — — — — |
| 15 | — — — — | — — — — | — — — — | — — — — | — — N | — — — — |
| 16 | — — — — | — — — — | — — — — | — — — — | — | — — — — |
| 17 | — — n n | — — — — | n n n N | — — n n | n | — — — — |
| 18 | — — — — | — — — — | — — — — | — — — — | — | — — — — |
| 19 | — — — — | — — — — | — — — — | — — — — | — N n | — — — — |
| 20 | — — — — | — — — — | — — — — | — — — — | — — n | — — — — |
| 21 | — — — — | — — — — | — — — — | — — — — | — n n | — — — — |
| 22 | — — — — | — — — — | — — — — | — — — — | — n n | — — — — |
| 23 | — — n N | — — — — | — — — n | — — — — | N N N | — — — — |
| 24 | — — — — | — — — — | — — — — | — — — — | n n N | — — — — |
| 25 | — — — — | — — — — | — — — — | — — — — | — | — — — — |
| 27 | — — — — | — — — — | — — — — | — — — — | — — — | — — — n |
| 28 | — — — — | — — — — | — — — — | — — — — | N N N | — — — — |
| 29 | — — — — | — — — — | — — — — | — — — — | n n N | — — — — |
| 30 | — — — — | — — — — | — — — — | — — n N | N | — — — — |
| 34 | — — — — | — — — — | — — — — | — — — — | — — n | — — — — |
| 36 | — — — — | — — — — | — — — — | — — — — | — n n | — — — — |
| 38 | — — — — | — — — — | — — — — | — — — — | — | — — — — |
| 39 | — — — — | — — — — | — — — — | — — — — | — | — — — — |
| 41 | — — — — | — — — — | — — — — | — — — — | — — n | — — — — |
| 42 | — — — — | — — — — | — — — — | — — — — | n n n | — — — — |
| 47 | — — — — | — — — — | — — — — | — — — — | — — N | — — — — |
| 48 | — — — — | — — — — | — — — — | — — — — | N N N | — — — — |
| 49 | — — — — | — — — — | — — — — | — — — — | n N N | — — — — |
| 50 | — — n N | — — — — | — — n N | — — n N | N | — — — — |
| 51 | — — — — | — — — — | — — — — | — — — — | — | — — — — |
| 52 | — — — — | — — — — | — — — — | — — — — | — | — — — — |
| 53 | — — — — | — — — — | — — — — | — — — — | N | — — — — |
| 54 | — — — — | — — — — | — — — — | — — — — | N | — — — — |
| 55 | — — — — | — — — — | — — — — | — — — — | — | — — — — |
| 56 | — — — — | — — — — | n — n n | — — n n | N | — — — — |

TABLE 1-5-continued

SERUM CROSS-NEUTRALIZATION RESULTS

| serum | 18 | | | | 21 | | | | 27 | | | | 49 | | | | 50 | | | | 54 | | | |
|---|---|---|---|---|---|---|---|---|---|---|---|---|---|---|---|---|---|---|---|---|---|---|---|---|
| virus | 2.5 | 5 | 10 | 20* | 2.5 | 5 | 10 | 20 | 2.5 | 5 | 10 | 20 | 2.5 | 5 | 10 | 20 | 2.5 | 5 | 10 | 20 | 2.5 | 5 | 10 | 20 |
| LSO12 | — | — | — | n | — | N | N | N | — | — | — | — | — | N | N | N | — | — | — | — | — | — | n | N |
| F9 | — | — | — | — | — | N | N | N | — | — | — | — | — | n | N | N | — | — | — | n | — | — | — | — |
| JOK92 | — | — | — | — | — | — | — | n | — | — | — | — | — | n | n | N | — | — | — | — | — | — | — | — |
| CFI68 | — | — | — | — | — | N | N | N | — | — | — | — | — | N | N | N | — | — | — | — | — | — | — | — |
| JOK63 | — | — | — | — | — | — | — | — | — | — | — | — | — | N | N | N | — | — | n | n | — | — | — | — |
| SA113 | — | — | — | — | — | — | n | N | — | — | — | — | — | N | N | N | — | — | — | — | — | n | n | n |
| 3 | N | N | N | N | — | — | — | — | — | — | — | — | — | N | N | N | — | — | — | — | — | N | N | N |
| 4 | — | — | — | — | — | — | — | n | — | — | — | — | — | — | N | N | N | N | N | N | — | — | — | n |
| 6 | — | — | — | — | — | — | — | — | — | — | — | — | — | — | n | n | — | — | — | — | — | — | — | — |
| 7 | — | — | — | — | — | — | n | n | — | — | — | — | — | N | N | N | — | — | — | — | — | — | n | N |
| 8 | — | — | — | — | — | — | n | — | — | — | — | — | — | — | — | N | — | — | — | — | — | — | — | — |
| 9 | — | — | — | — | — | — | — | n | — | — | — | — | — | n | N | N | — | — | — | — | — | — | — | — |
| 10 | — | — | — | — | — | — | — | — | — | — | — | — | — | — | — | — | — | — | — | — | — | — | — | — |
| 11 | — | — | — | — | — | — | — | — | — | — | — | N | — | — | — | — | — | — | — | — | — | — | — | — |
| 12 | — | — | — | — | — | — | — | — | — | — | — | — | — | n | N | N | — | — | — | — | — | — | — | — |
| 13 | — | — | — | — | — | — | n | — | — | — | — | — | — | N | N | N | — | — | — | — | n | n | n | n |
| 14 | — | — | — | — | — | — | — | — | — | — | n | n | — | n | N | N | — | — | — | — | — | — | n | N |
| 15 | — | — | — | — | — | N | N | N | — | — | — | — | — | n | N | N | — | — | — | — | — | n | n | n |
| 16 | — | — | — | — | — | — | — | — | — | — | — | — | — | — | — | n | — | — | — | — | — | — | — | — |
| 17 | — | — | n | n | — | n | n | n | — | — | n | n | — | N | N | N | — | — | — | — | — | — | n | N |
| 18 | n | N | N | N | — | — | — | n | — | — | — | — | — | — | N | N | — | — | — | — | — | — | — | — |
| 19 | — | — | — | — | — | n | — | n | — | — | — | — | — | — | n | n | — | — | — | — | — | — | — | — |
| 20 | — | — | — | — | — | — | — | — | — | — | — | — | — | — | — | N | N | N | N | N | — | — | — | — |
| 21 | — | — | — | — | N | N | N | N | — | — | — | — | — | — | n | N | — | — | — | — | — | — | — | — |
| 22 | — | — | — | — | — | — | — | — | — | — | — | — | — | — | n | n | — | — | — | — | — | — | — | — |
| 23 | — | — | — | — | — | N | N | N | — | — | — | n | — | N | N | N | — | — | n | N | — | — | n | n N |
| 24 | — | — | — | — | — | n | n | N | — | — | — | — | — | — | — | — | — | — | — | — | — | — | — | n |
| 25 | — | — | — | — | — | — | — | — | — | — | — | — | — | — | — | n | — | — | — | n | — | — | — | — |
| 27 | — | — | — | — | — | — | — | — | N | N | N | N | — | — | — | n | — | — | — | — | — | — | — | — |
| 28 | — | — | — | — | — | — | n | n | — | — | — | — | — | N | N | N | — | — | — | — | — | — | — | — |
| 29 | — | — | — | — | — | — | — | — | — | — | — | — | — | — | — | — | — | — | — | — | — | — | — | — |
| 30 | — | — | — | — | — | — | n | n N | — | — | — | — | — | N | N | N | — | — | — | — | — | — | — | — |
| 34 | — | — | — | — | — | — | — | — | — | — | — | — | — | — | — | N | — | — | — | — | — | — | — | — |
| 36 | — | — | — | — | — | — | — | — | — | — | — | — | — | — | n | N | — | — | — | — | — | — | — | — |
| 38 | — | — | — | — | — | — | — | — | — | — | — | — | — | — | — | — | — | — | — | — | — | — | — | — |
| 39 | — | — | — | — | — | — | — | — | — | — | — | — | — | — | — | — | — | — | — | — | — | — | — | — |
| 41 | — | — | — | — | — | — | — | — | — | — | — | — | — | — | n | N | — | — | — | — | — | — | — | — |
| 42 | — | — | — | — | — | — | — | — | — | — | — | — | — | n | n | N | — | — | — | — | — | — | — | — |
| 47 | — | — | — | — | — | n | n | n | — | — | — | — | — | — | n | N | — | — | — | — | — | — | — | — |
| 48 | — | — | — | — | — | n | n | N | — | — | — | — | — | N | N | N | — | — | — | n | — | — | — | — |
| 49 | — | — | — | — | — | — | n | n | — | — | — | — | N | N | N | N | — | — | — | n | — | — | — | — |
| 50 | — | — | — | — | — | N | N | N | — | — | — | — | — | N | N | N | N | N | N | N | — | — | n | N |
| 51 | — | — | — | — | — | N | N | N | — | — | — | — | — | — | — | n | — | — | — | — | — | — | — | — |
| 52 | — | — | — | — | — | — | — | — | — | — | — | — | — | N | N | N | — | — | — | — | — | — | — | — |
| 53 | — | — | — | — | — | n | N | N | — | — | — | — | — | n | n | N | — | — | — | — | — | — | — | n |
| 54 | — | — | — | — | — | — | — | n | — | — | — | — | — | — | n | N | — | — | — | — | n | N | N | N |
| 55 | — | — | — | — | — | N | N | N | — | — | — | — | — | — | N | N | — | — | — | — | — | — | — | — |
| 56 | — | — | n | N | — | n | n | N | — | — | — | — | — | N | N | N | — | — | — | — | — | — | — | n |

*2.5, 5, 10, 20 antibody units used in SN
N = 8/8 wells protected
n = 4-7/8 wells protected
— = 0-3/8 wells protected
blank = insufficient serum/not done The cross-neutralization data is summarized in TABLE 1-5. Each data point represents eight replicate wells assayed. "N", "n", or "-" represent the proportion of protected to unprotected wells, which is an indication of the extent of cross-neutralization. The serum neutralization results corresponding to each monospecific serum tested against its homologous virus are highlighted in the TABLE. These sera should neutralize completely; for the most part they do. The few exceptions, most notably JOK63, JOK92 and 11, show complete neutralization at higher AU values, but not at 2.5 AU. This is likely due to dilution errors. The most significant result from this data set is the high degree of cross-neutralization exhibited by sera FCV-21 and FCV-49, particularly the latter. The patterns of cross-neutralization of these sera appear to be similar to that of F9. (It should be noted that the data set for F9, and for FCV-21 and FCV-49 at 20 AU, is incomplete due to insufficient amounts of sera.) Although there are some differences in neutralization patterns between the three sera (FCV-21, FCV-49, and F9), isolates 11, 38 and 39 were consistently not neutralized by any of the three.

Example 1-10

Cross Neutralization Analysis of FCV-21 and FCV-49 Antisera Against FCV Viruses Isolated in 2003

FCV antisera in this study were generated by inoculating $10^5$ to $10^6$ $TCID_{50}$/ml of FCV intranasally into cats (4-5 cats/group). A booster inoculation was carried out 3 weeks later using the same amount of virus. Sera were collected 2 weeks post-boost and heat treated at 56° C. for 30 minutes.

Serum samples from each of the vaccinated cats were used in the serum neutralization assay against each of 26 FCV strains (TABLE 1-6). Serum samples were diluted at 1:8 and followed by 2-fold serial dilutions out to 1:16384 (12 dilutions total) in 600 ul volume. FCV with titer range between 50-500 $TCID_{50}$/ml in 600 ul were mixed with diluted serum samples together and incubated at room temperature for 45 min. Then 200 ul of sample was transferred into each well of 96-well plates seeded with CRFK cells in quadruplicate. The plates were incubated at 37° C., 5% CO2 for 6 days and end point neutralization titer was determined. Both serum neutralization (SN) titer and challenge virus back-titer were calculated by the method of Spearman-Karber (Spearman C, 1908, Brit J Psychol 2:227-242; Karber G, 1931, Arch exp Path Pharmak 162: 480-487).

Serum neutralization data were analyzed with cut-off titers of >23 and >15 and >10. The results are shown in TABLE 1-7. The data suggest that FCV-21, FCV-49 and FCV 26391-4 have broader cross neutralization profiles, and are therefore better vaccine candidates than the current FCV vaccine strain, F9.

TABLE 1-6

26 FCV STRAINS USED IN THE CROSS NEUTRALIZATION STUDIES

| Strain | Year | Location |
|---|---|---|
| 12217-02 | 2002 | NY |
| 19306 | 2003 | FL |
| 26391-4 | 2003 | FL |
| 27086-2 | 2003 | FL |
| 32561-1 | 2003 | IN |
| 32561-14 | 2003 | IN |
| 32561-15 | 2003 | IN |
| 32561-7 | 2003 | IN |
| 36069-2 | 2003 | MT |
| 84883-02 | 2002 | NY |
| F9 | 1960 | Not Known |
| J-1 | 1984 | CT |
| H | 1990 | AZ |
| 2280 | 1983 | Not Known |
| 255NVSL | 1970 | Not Known |
| 94580 | 2000 | NY |
| 100869-1 | 2000 | Ontario |
| 33585 | 2000 | MA |
| 88287 | 2000 | PA |
| 89391 | 2000 | PA |
| 101920-1 | 2002 | NY |
| 17932-17 | 2003 | RI |
| 30101-2 | 2003 | MT |
| 41927-8 | 2003 | CO |
| FCV-21 | 1993 | MI |
| FCV-49 | 1993 | PA |

TABLE 1-7

CROSS-NEUTRALIZATION ANALYSIS OF FCV-21, FCV-49, AND FCV 26391-4 IN COMPARISON WITH F9

| A. | % (SN titer >23) | Candidate over F9 % Increase (IN) |
|---|---|---|
| FCV-21 IN | 43.9 | 68.9 |
| FCV-49 IN | 33.9 | 30.4 |
| FCV 26391-4 IN | 28.9 | 11.2 |
| F9 IN | 26 | |

| B. | % (SN titer >15) | Candidate over F9 % Increase (IN) |
|---|---|---|
| FCV-21 IN | 51.5 | 62.5 |
| FCV-49 IN | 37.7 | 18.9 |
| FCV 26391-4 IN | 39.4 | 24.3 |
| F9 IN | 31.7 | |

| C. | % (SN titer >10) | Candidate over F9 % Increase (IN) |
|---|---|---|
| FCV-21 IN | 74.6 | 36.1 |
| FCV-49 IN | 63.1 | 15.2 |
| FCV 26391-4 IN | 63.5 | 15.9 |
| F9 IN | 54.8 | |

Example 1-11

Mortality and Clinical Scores for Cats Vaccinated with Felocell 4 Components with and without FCV-21

Domestic shorthair cats, about 8 weeks of age, were vaccinated with FELOCELL® 4 components which contain modified-live feline rhinotracheitis virus [FHV], calicivirus [FCV-F9], panleukopenia virus [FP] and *Chlamydia psittaci*, with or without another FCV strain, FCV-21. The vaccination regimens evaluated included: an initial subcutaneous vaccination followed by subcutaneous boosts on days 21 (SQ/SQ); an initial subcutaneous vaccination followed by one oral booster immunizations on day 21 (SQ/Oral); or an initial oral vaccination followed by a second oral vaccination on day 21. Oral vaccination was achieved by administration of the vaccine into the mouth. On day 42, all cats were challenged with approximately 1 mL of virulent systemic FCV-33585 (3 log of $TCID_{50}$/mL). All cats were monitored for clinical signs (temperature, conjunctivitis serous discharge, conjunctivitis mucopurulent discharge, rhinitis serous discharge, rhinitis mucopurulent discharge, sneezing, audible rales, coughing open mouth breathing, anorexia, dehydration, one oral ulcer<4 mm, multiple oral ulcers, oral ulcers>4 mm, salivating, nonbleeding external ulcer, bleeding external ulcers) of disease for 14 days post-challenge. Cats exhibiting severe clinical signs post-challenge that were consistent with calicivirus pathogenesis were euthanized.

As shown in TABLE 1-8, the addition of the new strain FCV-21 significantly increases the efficacy of FELOCELL 4, with or without the presence of FCV-F9. Both SQ/SQ vaccination and SQ/Oral vaccination seem to be efficacious for preventing FCV infection. Moreover, we have demonstrated efficacy against FCV infection even with Oral/Oral vaccination with addition of FCV-21 and absence of F9 in FELOCELL 4 and FELOCELL 3 (FELOCELL 3 is FELOCELL 4 without *Chlamydia psittaci*).

For TABLE 1-9, the vaccination regimens evaluated included an initial subcutaneous vaccination followed by two oral booster immunizations on day 21 and day 42 (SQ/Oral/Oral). We have demonstrated that the addition of FCV-21, with or without FCV-F9 in FELOCELL 4, significantly decreased both mortality and clinical scores.

TABLE 1-8

| Treatment | Vaccination | | | | Challenge | | | | Clinical Score | | |
|---|---|---|---|---|---|---|---|---|---|---|---|
| | # animals | Days | Dose | Route | Days | FCV strain | # animals | Mortality | Median | Minimum | Maximum |
| Neg. control | 10 | 0 | 1 ml | SQ | 42 | 33585 | 9 | 78% | 24 | 2 | 35 |
| | | 21 | 1 ml | SQ | | | | | | | |
| FELOCELL 4 | 10 | 0 | 1 ml | SQ | 42 | 33585 | 9 | 44% | 12 | 3 | 18 |
| | | 21 | 1 ml | SQ | | | | | | | |
| FELOCELL 4A* | 10 | 0 | 1 ml | SQ | 42 | 33585 | 10 | 0% | 2.5 | 0 | 11 |
| | | 21 | 1 ml | SQ | | | | | | | |
| FELOCELL 4 + FCV-21 | 10 | 0 | 1 ml | SQ | 42 | 33585 | 10 | 0% | 1.5 | 0 | 13 |
| | | 21 | 1 ml | SQ | | | | | | | |
| — | — | — | — | — | — | — | — | — | — | — | — |
| FELOCELL 4 | 10 | 0 | 1 ml | SQ | 42 | 33585 | 10 | 10% | 5.5 | 0 | 30 |
| | | 21 | 1 ml | Oral | | | | | | | |
| FELOCELL 4 + FCV-21 | 10 | 0 | 1 ml | SQ | 42 | 33585 | 10 | 0% | 3.5 | 0 | 13 |
| | | 21 | 1 ml | Oral | | | | | | | |
| FELOCELL 4A* | 10 | 0 | 1 ml | SQ | 42 | 33585 | 10 | 10% | 5 | 1 | 22 |
| | | 21 | 1 ml | Oral | | | | | | | |
| FELOCELL 4A* | 10 | 0 | 1 ml | Oral | 42 | 33585 | 10 | 0% | 3 | 0 | 10 |
| | | 21 | 1 ml | Oral | | | | | | | |
| — | — | — | — | — | — | — | — | — | — | — | — |
| FELOCELL 3 + FCV-21 | 10 | 0 | 1 ml | SQ | 42 | 33585 | 10 | 0% | 2 | 0 | 8 |
| | | 21 | 1 ml | SQ | | | | | | | |
| FELOCELL 3 + FCV-21 | 10 | 0 | 1 ml | SQ | 42 | 33585 | 10 | 0% | 4 | 0 | 10 |
| | | 21 | 1 ml | Oral | | | | | | | |
| FELOCELL 3A** | 10 | 0 | 1 ml | Oral | 42 | 33585 | 10 | 0% | 5 | 1 | 18 |
| | | 21 | 1 ml | Oral | | | | | | | |

*FELOCELL 4A: FELOCELL 4 without FCV-F9, but with FCV-21
**FELOCELL 3A: FELOCELL 3 without FCV-F9, but with FCV-21

TABLE 1-9

| Group | Treatment | Vaccination | | | | Challenge | | | | Clinical Score | | |
|---|---|---|---|---|---|---|---|---|---|---|---|---|
| | | # animals | Days | Dose | Route | Days | FCV strain | # animals | Morality | Median | Minimum | Maximum |
| T01 | Neg. control | 10 | 0 | 1 ml | SQ | 63 | 33585 | 10 | 100% | 25 | 21 | 31 |
| | | | 21 | 1 ml | Oral | 63 | | | | | | |
| | | | 42 | 1 ml | Oral | 63 | | | | | | |
| T02 | Felocell 4 + FCV-21 | 10 | 0 | 1 ml | SQ | 63 | 33585 | 10 | 0% | 5.5 | 0 | 17 |
| | | | 21 | 1 ml | Oral | 63 | | | | | | |
| | | | 42 | 1 ml | Oral | 63 | | | | | | |
| T03 | Felocell 4A* + FCV-21 | 10 | 0 | 1 ml | SQ | 63 | 33585 | 9 | 0% | 4 | 0 | 10 |
| | | | 21 | 1 ml | Oral | 63 | | | | | | |
| | | | 42 | 1 ml | Oral | 63 | | | | | | |
| T04 | Felocell 4 | 10 | 0 | 1 ml | SQ | 63 | 33585 | 10 | 30% | 10.5 | 1 | 30 |
| | | | 21 | 1 ml | Oral | 63 | | | | | | |
| | | | 42 | 1 ml | Oral | 63 | | | | | | |

*Felocell 4A: Felocell 4 without FCV-F9
**Felocell 3A: Felocell 3 without FCV-F9

Example 1-12

Cross Neutralization Analysis of Sera from Cats Vaccinated with FELOCELL 4 Components with and without FCV-21

Serum samples from each cat in the study described in EXAMPLE 1-11, were collected following the second vaccination, but before 85 challenge. The samples were heat treated at 56° C. for 30 minutes, and evaluated in the serum neutralization assay against each of 26 FCV strains as previously described in EXAMPLE 1-10 (TABLE 1-6).

Serum neutralization data were analyzed with cut-off titers of >23 and >15, and an average of the two cut-off titers was calculated (Ave). The results are shown in TABLE 1-10. The data indicate that all of the vaccine formulations containing FCV-21 had broader cross neutralization profiles than the vaccines containing the traditional FCV-F9 strain (~60% vs. 40%). This resulted in an approximate 50% increase in the number of the FCV strains neutralized.

TABLE 1-10

| Treatment | Vaccination | | | | Serum Collection | | Cross Neutralization | | |
|---|---|---|---|---|---|---|---|---|---|
| | # animals | Days | Dose | Route | Days | # animals | % (>23) | % (>15) | % (Ave) |
| Neg. control | 10 | 0 | 1 ml | SQ | 42 | 9 | 10.8 | 13.9 | 12.4 |
| | | 21 | 1 ml | SQ | | | | | |
| FELOCELL 4 | 10 | 0 | 1 ml | SQ | 42 | 9 | 38.5 | 42.3 | 40.4 |
| | | 21 | 1 ml | SQ | | | | | |
| FELOCELL 4A* | 10 | 0 | 1 ml | SQ | 42 | 10 | 58.9 | 64.6 | 61.8 |
| | | 21 | 1 ml | SQ | | | | | |
| FELOCELL 4 + FCV-21 | 10 | 0 | 1 ml | SQ | 42 | 10 | 56.5 | 62.3 | 59.4 |
| | | 21 | 1 ml | SQ | | | | | |
| FELOCELL 4 | 10 | 0 | 1 ml | SQ | 42 | 10 | 39.2 | 42.7 | 41.0 |
| | | 21 | 1 ml | Oral | | | | | |
| FELOCELL 4 + FCV-21 | 10 | 0 | 1 ml | SQ | 42 | 10 | 56.2 | 60 | 58.1 |
| | | 21 | 1 ml | Oral | | | | | |
| FELOCELL 4A* | 10 | 0 | 1 ml | SQ | 42 | 10 | 49.6 | 59.2 | 54.4 |
| | | 21 | 1 ml | Oral | | | | | |
| FELOCELL 4A* | 10 | 0 | 1 ml | Oral | 42 | 10 | 51.2 | 54.6 | 52.9 |
| | | 21 | 1 ml | Oral | | | | | |
| FELOCELL 3 + FCV-21 | 10 | 0 | 1 ml | SQ | 42 | 10 | 53.9 | 62.7 | 58.3 |
| | | 21 | 1 ml | SQ | | | | | |
| FELOCELL 3 + FCV-21 | 10 | 0 | 1 ml | SQ | 42 | 10 | 55.8 | 63.9 | 59.9 |
| | | 21 | 1 ml | Oral | | | | | |
| FELOCELL 3A** | 10 | 0 | 1 ml | Oral | 42 | 10 | 60.8 | 68.1 | 64.5 |
| | | 21 | 1 ml | Oral | | | | | |

*FELOCELL 4A: FELOCELL 4 without FCV-F9, but with FCV-21
**FELOCELL 3A: FELOCELL 3 without FCV-F9, but with FCV-21

As also shown in TABLE 1-10, the addition of the new strain FCV-21 significantly increased the cross neutralization profile of FELOCELL 4, with or without the presence of FCV-F9. Broader cross neutralization profiles were observed with both SQ/SQ vaccination and SQ/Oral vaccination. Moreover, we have demonstrated enhanced cross neutralization profiles with Oral/Oral vaccination with the presence of FCV-21, but not F9, in FELOCELL 4 and FELOCELL 3.

In TABLE 1-11, the vaccination regimens evaluated included an initial subcutaneous vaccination followed by two oral booster immunizations on day 21 and day 42 (SQ/Oral/Oral). The results indicate that the addition of FCV-21, with or without FCV-F9 in FELOCELL 4, resulted in significantly broader cross neutralization profiles (approximate 40% increase).

TABLE 1-11

| Treatment | Vaccination | | | | | Serum Collection | | Cross Neutralization | | |
|---|---|---|---|---|---|---|---|---|---|---|
| | # Animals | Days | Date | Dose | Route | Days | # Animals | % (>23) | % (>15) | % (Ave) |
| Neg. control | 10 | 0 | Feb. 15, 2005 | 1 ml | SQ | 63 | 10 | 5.8 | 10.4 | 8.1 |
| | | 21 | Mar. 8, 2005 | 1 ml | Oral | | | | | |
| | | 42 | Mar. 29, 2005 | 1 ml | Oral | | | | | |
| FELOCELL 4 + FCV-21 | 10 | 0 | Feb. 15, 2005 | 1 ml | SQ | 63 | 10 | 72.5 | 77.1 | 74.8 |
| | | 21 | Mar. 8, 2005 | 1 ml | Oral | | | | | |
| | | 42 | Mar. 29, 2005 | 1 ml | Oral | | | | | |
| FELOCELL 4A* | 10 | 0 | Feb. 15, 2005 | 1 ml | SQ | 63 | 9 | 72.5 | 76.7 | 74.6 |
| | | 21 | Mar. 8, 2005 | 1 ml | Oral | | | | | |
| | | 42 | Mar. 29, 2005 | 1 ml | Oral | | | | | |
| FELOCELL 4 | 10 | 0 | Feb. 15, 2005 | 1 ml | SQ | 63 | 10 | 49.6 | 57.9 | 53.8 |
| | | 21 | Mar. 8, 2005 | 1 ml | Oral | | | | | |
| | | 42 | Mar. 29, 2005 | 1 ml | Oral | | | | | |

*FELOCELL 4A: FELOCELL 4 without FCV-F9, but with FCV-21

Numbered description of the invention. Additional description of the inventions and examples. 1. A vaccine for immunizing cats against feline calicivirus comprising a FCV-21 capsid protein or an isolated FCV-21 capsid protein. 2. A vaccine for immunizing cats against feline calicivirus comprising a FCV-21 capsid protein or an isolated FCV-21 capsid protein wherein said capsid protein comprises protein sequence (SEQ ID 13) and sequences having at least about 91.2%, 95% and 99% identity; wherein said capsid protein is provided in an effective amount to produce an immune response, and a pharmaceutically acceptable carrier. 3. A DNA vaccine for immunizing cats against feline calicivirus comprising nucleic acid sequences that code for a FCV-21 capsid protein or an isolated FCV-21 capsid protein wherein said DNA comprises a sequence (SEQ. ID 12) and sequences having at least about 78.7%, and 79.2% sequence identity and allowing for conservative substitutions. 4. A vaccine for immunizing cats against feline calicivirus comprising a FCV-49 capsid protein or an isolated FCV-49 capsid protein wherein said capsid protein comprises a protein sequence from strain FCV-49. 5. A vaccine for immunizing cats against feline calicivirus comprising an FCV-49 capsid protein, or an isolated FCV-49 capsid protein, wherein said capsid protein comprises protein sequence (SEQ ID 15) and sequences having at least about 92.7%, 95% and 99% identity; wherein said capsid protein is provided in an effective amount to produce an immune response, and a pharmaceutically acceptable carrier. 6. A DNA vaccine for immunizing cats against feline calicivirus comprising nucleic acid sequences that code for a FCV-49 capsid protein or an isolated FCV-49 capsid protein wherein said DNA comprises a sequence (SEQ. ID 14) and sequences having at least about 78.9%, i.e. 79.4% (78.9+0.5) sequence identity and allowing for conservative substitutions. 7. A vaccine for immunizing cats against feline calicivirus comprising a FCV-26391-4 capsid protein, or an isolated FCV-26391-4 capsid protein, wherein said capsid protein comprises protein sequences from strain FCV-26391-4. 8. A vaccine for immunizing cats against feline calicivirus comprising an FCV-26391-4 capsid protein wherein said capsid protein comprises protein sequence (SEQ ID 17) and sequences having at least about 91.8%, 95% and 99% identity wherein said capsid protein is provided in an effective amount to produce an immune response, and a pharmaceutically acceptable carrier. 9. A DNA vaccine for immunizing cats against feline calicivirus comprising nucleic acid sequences that code for a FCV-26391-4 capsid protein or an isolated FCV-26391-4 capsid protein wherein said DNA comprises a sequence (SEQ. ID 16) and sequences having at least about 78.4%, i.e. 78.9% (78.4+0.5) sequence identity. 10. The vaccine of any of claims 1-3 wherein the polynucleotide is selected from the group consisting essentially of SEQ ID NOS. 12, 14, 16. 11. The vaccine of any of claim 1-3, further comprising either alone or in any combination the following: where it contains an adjuvant, wherein the FCV component is live, wherein the FCV component is attenuated, wherein the FCV component is inactivated, which may include at least one other feline calicivirus strain selected from the group consisting of FCV-F9, FCV-LLK, FCV-M8, FCV-255, and FCV-2280. 12. The vaccine of claims, 1, 4, and 7, wherein the vaccine includes at least one other feline pathogen, selected from the group consisting of feline herpesvirus, feline leukemia virus, feline immunodeficiency virus, *Chlamydia pssittaci*, and feline parvovirus, rabies virus and *Bordetella bronchiseptica*. 13. A vaccine to immunize cats against feline calicivirus which comprises a nucleotide sequence of a FCV capsid protein selected from the group consisting of a polypeptide having 93% or greater identity with SEQ ID NO.13, 15, or 17, wherein the FCV isolate is not strain 213-95, and wherein the nucleic acid sequence is operably linked to a heterologous promoter sequence, in an effective amount to produce an immune response, and a pharmaceutically acceptable carrier. 14. The vaccine of claim 13 wherein the nucleotide sequence is selected from the group consisting essentially of SEQ ID NOS. 12, 14 and 16. 15. The vaccine of claim 13, wherein the nucleotide sequence is in any of the following: a plasmid, a recombinant virus vector. 16. The vaccine of claim 13, wherein the recombinant virus vector is selected from the group consisting of feline herpesvirus, raccoon poxvirus, canary poxvirus, adenovirus, Semliki Forest virus, Sindbis virus, and vaccinia virus. 17. An immunogenic composition comprising a veterinarily acceptable vehicle of excipient and an isolated strain of FCV that binds to a monoclonal antibody selected from the monoclonal antibodies described herein as 23, 26, 41, 44 and 56. 18. An immunogenic composition comprising a veterinarily acceptable vehicle of excipient and an isolated strain of FCV that selectively binds to a monoclonal antibody selected from the monoclonal antibodies described herein as 23, 26, 41, 44 and 56. 19. The immunogenic compositions of claim 17 and 18 wherein the FCV strain is inactivated, where said FCV strain is a vaccine, and where the composition comprises an adjuvant. 20. A method for immunizing a cat against feline calicivirus comprising: administering to the cat an effective dose of a vaccine of any of claims 1-14, wherein the vaccine additionally comprises an adjuvant.

Part 2

This Section Below Provides Detailed Information About Methods of Immunizing Animals Against Virus and in Particular Cats Against Calicivirus Unless otherwise indicated, the disclosures below use the definitions provided above and below.

Described herein are methods and materials for treating and immunizing animals with vaccine and in particular cats against feline calicivirus (FCV). The method includes administering to the cat therapeutically effective amounts of first and second vaccines that are capable of inducing an immune response, and in particular in the cat against FCV. The first vaccine is typically administered parenterally, but in some situations may be administered orally, while the second vaccine is administered orally or oronasally N days following administration of the first vaccine. These vaccines are typically administered parenterally first because they typically cause oral lesions if initially administered orally. Surprisingly, here we disclose strains FCV-21, FCV-49 and FCV 26391-4 that are so safe and effective they may be administered as a first oral administration followed by a second oral administration. Here, N is an integer from 3 to 120, inclusive, but is typically an integer from 7 to 42, inclusive, or from 14 to 28, inclusive, preferred is about 3 weeks and also about 2-4 weeks. Alternatively, the second vaccine may be administered after the cat has developed an FCV serum neutralization titer of about 1:6, 1:9, 1:12, 1:15, 1:18, or greater.

The method may also include one or more additional parenteral, oral or oronasal administrations of an FCV vaccine M days following administration of the first vaccine or the second vaccine, where M is an integer from 1 to 120, inclusive. Thus, representative vaccination regimens include (1) subcutaneous administration of a first FCV vaccine, followed by oral administration of a second FCV vaccine; (2) successive subcutaneous administrations of first and third FCV vaccines, followed by oral administration of a second FCV vaccine; and (3) subcutaneous administration of a first FCV vaccine, followed by successive oral administrations of second and third FCV vaccines.

As described above, the first vaccine is administered orally or parenterally (e.g., subcutaneously), the second vaccine is administered orally or oronasally, and an optional third vaccine may be administered parenterally, orally or oronasally. Any device may be used to administer the vaccines, including syringes, droppers, needleless injection devices, and the like. For oronasal administration, a syringe fitted with a cannula may be used to place drops of the vaccine in the cat's nose and mouth.

The method may employ any vaccine that is capable of inducing an immune response in the cat against FCV, as long as the first vaccine is adapted to be administered parenterally and the second vaccine is adapted to be administered orally or oronasally. As noted above, the optional third vaccine is adapted to be administered parenterally, perorally, or oronasally. The first, second, and optional third vaccines may be the same or different and each comprises, independently, an antigen or antigens derived from one or more strains of FCV. Useful vaccines thus include live virus vaccines, modified-live virus vaccines, and inactivated virus vaccines. Live and modified-live FCV vaccines contain FCV strains that do not cause disease in cats and have been isolated in non-virulent form or have been attenuated using well-known methods, including serial passage in a suitable cell line or exposure to ultraviolet light or a chemical mutagen. Inactivated or killed FCV vaccines contain FCV strains which have been inactivated by known methods, including treatment with formalin, betapropriolactone, binary ethyleneimine, and the like. Exemplary vaccines include those containing non-virulent strains selected from FCV-F9, FCV-M8, FCV-255, FCV-2280, FCV-21, FCV-49, FCV 26391-4, etc., either alone or in combination.

Other useful vaccines derived from one or more strains of FCV include recombinant vaccines and DNA vaccines (i.e., subunit vaccines). Recombinant vaccines include recombinant virus vectors, each containing a nucleic acid which encodes an antigen derived from a strain of FCV. Such vectors may be prepared by inserting a cDNA that encodes an antigen derived from an FCV strain (e.g., a capsid protein) into the genome of a non-virulent virus, including strains of herpesvirus, poxvirus, adenovirus, and the like. For virus vectors, the cDNA is operably linked to a eukaryote transcription promoter at the 5' end of the antigen encoding sequence and is operably linked to a eukaryote termination signal and poly (A) signal at the 3' end of the antigen encoding sequence, so that the transcription promoter and termination sequences regulate expression of the antigen. Useful transcription promoters include Rous sarcoma virus long terminal repeat promoter (RSV-LTR), Cytomegalovirus (CMV) major immediate-early promoter, simian vacuolating virus 40 (SV40) T antigen promoter, and inducible promoters, such as metallothionein promoter. For a discussion of recombinant FCV vaccines, see U.S. Pat. No. 5,716,822 to Wardley et al., which is herein incorporated by reference in its entirety.

DNA vaccines include DNA molecules (e.g., plasmids) having a nucleic acid sequence that encodes an FCV antigen, such as an FCV capsid protein or a specific immunogenic fragment thereof, which elicits an immune response in the cat against FCV. The nucleic acid coding sequence is operably linked to a transcriptional promoter that enables expression of the DNA when it is inoculated into the cells of the cat. Useful promoters include the RSV-LTR promoter, the CMV major immediate-early promoter, and the SV40 T antigen promoter. Additionally, the nucleic acid may be operably linked, at or near the termination codon of the sequence encoding the FCV antigen, to a nucleic acid fragment comprising a transcription termination signal and poly(A) recognition signal. For a discussion of DNA vaccines, see U.S. Pat. Nos. 5,580,859, 5,589,466, and 5,703,055, to Felgner et al.

Other useful vaccines include those containing one or more subunit antigens, such as an FCV capsid protein or an immunogenic fragment of the capsid protein, which has been isolated and purified. The subunit antigen may be produced in a recombinant expression vector that produces the antigen in vitro using methods described above. The resultant antigen is subsequently isolated and purified. Useful expression vectors include various microorganisms, including bacteria, yeast and fungi, as well as eukaryotes, such as mammalian and insect cells. Other useful expression vectors include viruses, such as adenoviruses, poxviruses, herpesviruses, Semliki Forest viruses, baculoviruses, bacteriophages, Sindbis viruses, Sendai virus, and the like. Expression of the FCV subunit antigen in a microorganism permits production of the antigenic protein using commercial-scale fermentation technologies. Various methods may be used to isolate and purify the antigens, including gel filtration, affinity chromatography, ion exchange chromatography, centrifugation, and the like.

One or more of the vaccines may also contain antigens for immunizing cats against one or more pathogens besides FCV, including feline herpesvirus, feline leukemia virus, feline immunodeficiency virus, feline panleukopenia virus, and feline *Chlamydia*.

Other components of vaccines may include pharmaceutically acceptable excipients, including carriers, solvents, and diluents, isotonic agents, buffering agents, stabilizers, preservatives, immunomodulatory agents (e.g., interleukins, interferons, and other cytokines), vaso-constrictive agents, antibacterial agents, antifungal agents, and the like. Typical carriers, solvents, and diluents include water, saline, dextrose, ethanol, glycerol, and the like. Representative isotonic agents include sodium chloride, dextrose, mannitol, sorbitol, lactose, and the like. Useful stabilizers include gelatin, albumin, and the like.

The vaccines may also include one or more adjuvants which increase the immune response to the antigen. Representative adjuvants include oil-based adjuvants, such as Freund's Complete Adjuvant and Freund's Incomplete Adjuvant, mycolate-based adjuvants (e.g., trehalose dimycolate), bacterial lipopolysaccharides, peptidoglycans (i.e., mureins, mucopeptides, or glycoproteins such as N-Opaca, muramyl dipeptide or analogs thereof), proteoglycans (e.g., extracted from *Klebsiella pneumoniae*), streptococcal preparations (e.g., OK432), BIOSTIM® (e.g., 01K2), Iscoms (e.g., see European Patent Application Nos. EP 109942, EP 180564 and EP 231039), aluminum hydroxide, saponin, diethylaminoethyl-dextran, neutral oils (e.g., miglyol), vegetable oils (e.g., arachis oil), liposomes, PLURONIC® polyols. Other adjuvants include the RIBI adjuvant system, alum, aluminum hydroxide gel, cholesterol, oil-in-water emulsions, water-in-oil emulsions, block co-polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *Escherichia coli* (recombinant or otherwise), cholera toxin, or muramyl dipeptide, among others.

Dose sizes of the FCV vaccines typically range from about 1 mL to about 2 mL, inclusive. Each dose contains a therapeutically effective amount of the FCV antigen or antigens that may vary depending on the age and general condition of the cat, the route of administration, the nature of the FCV antigen, and other factors. For vaccines containing modified live viruses or attenuated viruses, a therapeutically effective dose generally ranges from about $10^6$ TCID$_{50}$ to about $10^8$ TCID$_{50}$, inclusive. For vaccines containing subunit antigens, such as FCV capsid proteins, a therapeutically effective dose generally ranges from about 10 µg to about 100 µg, inclusive. The other components of the vaccines may be adjusted to modify the physical and chemical properties of the vaccines. For example, adjuvants typically comprises from about 25 µg to about 1000 µg, inclusive, of a 1 mL dose. Similarly, antibiotics typically comprise from about 1 µg to about 60 µg, inclusive, of a 1 mL dose.

The FCV vaccines are provided in various forms depending on the route of administration, storage requirements, and the like. For example, the vaccines can be prepared as aqueous solutions or dispersions suitable for use in syringes, droppers, etc. or can be prepared as lyophilized powders, which are reconstituted in saline, HEPES buffer, and the like, prior to use.

PART 2 EXAMPLES AND TABLES

The following examples are intended to be illustrative and non-limiting, and represent a few specific embodiments of the present invention.

Example 2-1

Subcutaneous/Oral Vaccination Regimen with FELOCELL® 4 and FEL-O-VAX®

Domestic shorthair cats, 4-5 months of age, were vaccinated with FELOCELL® 4 (Pfizer Inc.; modified-live feline rhinotracheitis virus [FHV], calicivirus [FCV], panleukopenia virus [FP] and *Chlamydia psittaci*), with FEL-O-VAX® (Fort Dodge; killed FHV, FCV, FP, and *C. psittaci*), or with sterile diluent (control group). The vaccination regimens evaluated included: an initial subcutaneous vaccination followed by subcutaneous boosts on days 21 and 42 (SQ/SQ/SQ); an initial subcutaneous vaccination followed by two oral booster immunizations on days 21 and 42 (SQ/Oral/Oral); or an initial subcutaneous vaccination followed by a second subcutaneous vaccination on day 21, and an oral boost on day 42. All doses were 1 mL. Oral vaccination was achieved by administration of the vaccine into the mouth. On day 99, all cats were challenged with approximately 3.5 mL of virulent systemic FCV-33585 (4.8 log of $TCID_{50}$/mL). The challenge was performed by administering approximately 3 mL of the dose in canned cat food, and 0.05 mL via nasal instillation. All cats were monitored for clinical signs of disease for 14 days post-challenge. Cats exhibiting severe clinical signs post-challenge that were consistent with calicivirus pathogenesis were euthanized.

As shown in TABLE 2-1, the group vaccinated via the SQ/Oral/Oral regimen had a mortality rate of only 10%, while the control group had a mortality rate of 90%. The group vaccinated via the SQ/SQ/SQ regimen had a mortality rate of 50%, while the group vaccinated via the SQ/SQ/Oral regimen had mortality rate of 20%. These results suggest that SQ vaccination followed by an Oral boost significantly enhances the effectiveness of FELOCELL® 4 vaccination against virulent FCV challenge. Not only did mortality rates decrease from 50% (SQ/SQ/SQ) to 10% (SQ/Oral/Oral) or 20% (SQ/SQ/Oral) when oral vaccination was a part of the regimen, but as shown in TABLE 2-2, the severity of clinical signs such as skin lesions (SL), inappetence (IA), depression (DP), oral ulcers (OU), lameness (LN), sneezing (SZ), nasal discharge (ND) and watery eyes (WE), decreased as well.

Table 2-1

Mortality of Cats Challenged with Virulent FCV-33585 Following Vaccination (Example 2-1)

TABLE 2-1

| | | Vaccination | | Challenge | |
|---|---|---|---|---|---|
| Group | Treatment | # Animals | Route | # Animals | Mortality, % |
| T1 | Control | 10 | SQ/SQ/SQ | 10 | 90 |
| T2 | FELOCELL ® 4 | 5 | SQ/SQ/SQ | 4 | 50 |
| T3 | FELOCELL ® 4 | 10 | SQ/SQ/Oral | 10 | 20 |
| T4 | FELOCELL ® 4 | 10 | SQ/Oral/Oral | 10 | 10 |
| T5 | FEL-O-VAX ® | 5 | SQ/SQ/SQ | 5 | 60 |

Table 2-2

Clinical Symptoms (% of Animals) Following Vaccination and Subsequent FCV-33585 Challenge (Example 2-1)

TABLE 2-2

| Group | Route | SL | IA | EP | OU | LN | SZ | ND | WE |
|---|---|---|---|---|---|---|---|---|---|
| T1 | SQ/SQ/SQ | 50 | 100 | 100 | 70 | 100 | 30 | 90 | 70 |
| T2 | SQ/SQ/SQ | 100 | 100 | 100 | 100 | 100 | 25 | 100 | 25 |
| T3 | SQ/SQ/Oral | 70 | 70 | 50 | 60 | 70 | 20 | 30 | 10 |
| T4 | SQ/Oral/Oral | 10 | 40 | 20 | 40 | 50 | 10 | 30 | 0 |
| T5 | SQ/SQ/SQ | 40 | 80 | 60 | 60 | 60 | 40 | 60 | 20 |

Example 2-2

Mean FCV Serum Neutralization Titers Following SQ/Oral Vaccination

Blood samples taken from the cats of EXAMPLE 2-1 were collected on study days 0, 21, 42, 63, 98 and 113, and evaluated in a serum neutralization (SN) assay for their capacity to neutralize FCV. Serum samples were diluted 1:8, followed by 2-fold serial dilutions out to 1:16384 (12 dilutions total) in 600 µL volumes. Feline caliciviruses with a titer of 50-500 $TCID_{50}$/mL in 600 µL were mixed with the diluted serum samples and incubated at room temperature for 45 min. Then 200 µL of each diluted sample was transferred into separate wells of 96-well plates seeded with Crandel Feline Kidney (CrFK) cells in quadruplicate. The plates were incubated at 37° C., under 5% $CO_2$ for 6 days at which time end point neutralization titers were determined. Both the serum neutralization (SN) titer and the challenge virus back-titer were calculated using the method of Spearman-Karber See, C. Spearman, *Brit. J. Psychol.* 2:227-242 (1908) and G. Karber, *Arch. Exp. Path. Pharmak.* 162:480-487 (1931). As shown in TABLE 2-3, FELOCELL® 4 administered via the SQ/Oral/Oral or SQ/SQ/Oral vaccination regimens had significantly higher FCV SN titers. These data correlate with the significant reduction in mortality rates described in EXAMPLE 2-1

Table 2-3

Mean FCV Sn (Serum Neutralization) Titers at Various Study Days (Example 2-2)

TABLE 2-3

| | Vaccination | Mean FCV SN Titers* | | | | | | # Animals |
|---|---|---|---|---|---|---|---|---|
| Group | Route | 0 | 21 | 42 | 63 | 98 | 113 | Day 113 |
| T1 | SQ/SQ/SQ | 3 | 2 | 4 | 3 | 4 | 7340 | 1 |
| T2 | SQ/SQ/SQ | 3 | 18 | 17 | 24 | 29 | 5986 | 2 |
| T3 | SQ/SQ/Oral | 3 | 27 | 36 | 310 | 1032 | 5783 | 8 |

TABLE 2-3-continued

| | Vaccination | Mean FCV SN Titers* | | | | | | # Animals |
|---|---|---|---|---|---|---|---|---|
| Group | Route | 0 | 21 | 42 | 63 | 98 | 113 | Day 113 |
| T4 | SQ/Oral/Oral | 3 | 18 | 431 | 877 | 1980 | 5787 | 9 |
| T5 | SQ/SQ/SQ | 4 | 3 | 6 | 8 | 15 | 3563 | 2 |

*Measured on day 0, day 21, day 42, day 63, day 98, and day 133 post-vaccination.

Example 2-3

Effectiveness of SQ/Oral Administration of FELOCELL® 4 and FEL-O-VAX® Against Feline Panleukopenia Virus Serum samples from the cats of EXAMPLE 2-1 were also assayed for their mean FP titers. As shown in TABLE 2-4, all of the cats were seronegative at the beginning of the study. Subsequently, the mean titers of the control group remained at 1 for the duration of the sampling intervals (days 21 and 42). However, the mean titers of the other four vaccination groups increased significantly.

Table 2-4

Mean Serum Antibody Titers to Feline Panleukopenia Virus (Example 2-3)

TABLE 2-4

| | Vaccination | Mean Serum FP Titer* | | |
|---|---|---|---|---|
| Group | Route | 0 | 21 | 42 |
| T1 | SQ/SQ/SQ | 1 | 1 | 1 |
| T2 | SQ/SQ/SQ | 1 | 5782 | 5782 |
| T3 | SQ/SQ/Oral | 1 | 5595 | 5793 |
| T4 | SQ/Oral/Oral | 1 | 5499 | 5693 |
| T5 | SQ/SQ/SQ | 1 | 2360 | 4887 |

*Measured on day 0, day 21, and day 42 post-vaccination.

Example 2-4

Clinical Symptoms for Cats Vaccinated with FELOCELL® 4 by Various Routes of Administration Oronasal (ON) administration of FELOCELL® 4 was achieved by instillation of drops into the nares of the animal. As indicated in TABLE 2-5, groups of 10 cats (T1, T2, T3), 6-7 months of age, were vaccinated and boosted on day 21 according to the regimens shown in TABLE 2-5: subcutaneous vaccination and boost (SQ/SQ); subcutaneous vaccination and oronasal booster (SQ/ON); or oronasal vaccination and boost (ON/ON). Vaccine was subcutaneously administered on the right side of the neck (1 mL); oronasal administration was by delivery of 0.5 mL of vaccine into each nare. Beginning on day 1, all cats were observed daily for general health conditions.

Table 2-5

Clinical Symptoms for Cats Vaccinated with Felocell ®4 via Different Routes of Administration (Example 2-4)

TABLE 2-5

| | Vaccination | Clinical symptoms, % | | | | | |
|---|---|---|---|---|---|---|---|
| Group | Route | NU | OU | SZ | ND | WE | IA |
| T1 | SQ/SQ | 0 | 0 | 0 | 0 | 0 | 50 |
| T2 | SQ/ON | 0 | 0 | 20 | 0 | 0 | 20 |
| T3 | ON/ON | 10 | 30 | 90 | 50 | 60 | 20 |

As shown in TABLE 2-5, cats receiving both vaccinations oronasally had high levels of clinical symptoms, including nasal ulcers (NU), oral ulcers (OU), persistent sneezing (SZ), nasal discharge (ND), watery eyes (WE) and transient inappetence (IA). Cats vaccinated via the SQ/ON regimen, however, displayed fewer clinical symptoms than ON/ON-vaccinated cats, with no indication of nasal ulcers, oral ulcers, nasal discharge, or watery eyes. Also, subjects in the SQ/ON group exhibited less sneezing than cats in the ON/ON group. The safety profile of the SQ/ON group was similar to that of the SQ/SQ group.

Example 2-5

The Effect of Different Vaccination Routes on Serological Responses to FELOCELL® 4 Antigens Serum samples from cats enrolled in the study described in EXAMPLE 2-4 were assayed for serological reactivity to various viral antigens present in the FELOCELL® 4 vaccine. Mean serum neutralization antibody titers to FCV, FHV and FP were determined for study days 0, 21 and 42. As shown in TABLE 2-6, all three vaccination regimens resulted in a strong immune response to FP. The immune response to FHV was barely detectable due to difficulties with the assay. However, serum neutralization titers against FCV were significantly higher in the ON/ON and SQ/ON groups, as compared to the SQ/SQ group. These results suggest that cats in the ON/ON and SQ/ON groups would be protected against a virulent FCV challenge, but that the SQ/SQ group may not be.

Table 2-6

Serological Responses of Cats Vaccinated with FELOCELL® 4 Via Different Routes (Example 2-5)

TABLE 2-6

| | Vacc'n | FCV Titer* | | | FHV Titer* | | | FP Titer* | | |
|---|---|---|---|---|---|---|---|---|---|---|
| Group | Route | 0 | 21 | 42 | 0 | 21 | 42 | 0 | 21 | 42 |
| T1 | SQ/SQ | 3 | 4 | 7 | 3 | 3 | 3 | 3 | 10884 | 10441 |
| T2 | SQ/ON | 3 | 14 | 151 | 3 | 3 | 5 | 3 | 11113 | 11585 |
| T3 | ON/ON | 3 | 75 | 491 | 3 | 4 | 16 | 3 | 5333 | 10960 |

*Measured on day 0, day 21, and day 42 post-vaccination.

Example 2-6

Serum Neutralization Titers Against FCV-F9
Administered Via a SQ or ON Route

Six cats per group were vaccinated with the FCV-F9 antigen present in the FELOCELL® 4 vaccine, either SQ or ON. Three weeks following the initial vaccination, all cats were boosted with the same antigen via the same route as previously. All doses were 1 mL. Serum samples were collected three weeks after the booster immunization. As shown in TABLE 2-7, serum neutralization titers were determined for these samples against a panel of 26 FCV strains. The FCV strains chosen for the panel were selected based upon genetic diversity (as determined by the sequence of their capsid hyper-variable region), as well as geographic distribution. In addition, the virulence phenotype of each strain was also considered. Serum samples from cats vaccinated ON with F9 neutralized more FCV strains in the 26 member panel, as compared to samples from SQ-vaccinated cats. Using 23 as the cut-off value for neutralization titers, ON vaccination resulted in titers at or above the cut-off for 26% of the panel members, while SQ vaccination resulted in only 16% meeting the criteria. For a titer cut-off of 15, ON vaccination yielded 32% of panel members at or above the cut-off; SQ yielded only 17%.

Table 2-7

Serum Cross-Neutralization Titers for Serum
Generated SQ VS. on FCV-F9 Against 26 FCV Viral
Panel (Example 2-6)

TABLE 2-7

| FCV-F9 | % Pos. (>23*) | % Pos. (>15*) |
|---|---|---|
| SQ Inoculation | 16 | 17 |
| ON Inoculation | 26 | 32 |
| ON over SQ (%) | 163 | 188 |
| SQ over ON (%) | 62 | 53 |

*Neutralization titer ≧23 as cut-off value; or neutralization titer of ≧15 as cut-off value.

Example 2-7

Mortality and Clinical Scores for Cats Vaccinated
with Two Doses of FELOCELL® 4 or
FELOCELL® 3 Components and Modified-Live
FCV-21

Domestic shorthair cats, about 8 weeks of age, were administered vaccines containing modified-live feline rhinotracheitis virus (FHV), panleukopenia virus (FP), *Chlamydia psittaci*, and (1) FCV-F9 (FELOCELL® 4 or FELOCELL® 3), (2) FCV-F9 and FCV-21 (FELOCELL® 4 plus FCV-21, or FELOCELL® 3 plus FCV-21), or (3) FCV-21 (FELOCELL® 4A or FELOCELL® 3A). The vaccination regimens included: an initial subcutaneous vaccination followed by subcutaneous boosts on day 21 (SQ/SQ); an initial subcutaneous vaccination followed by one oral booster immunization on day 21 (SQ/Oral); or an initial oral vaccination followed by a second oral vaccination on day 21 (Oral/Oral). Each cat within the different dosing regimens (groups T1 to T10, 10 cats per group) received 1 mL of vaccine. Oral vaccination was achieved by administration of the vaccine into the mouth. On day 42, all cats were challenged with approximately 1 mL of virulent systemic FCV-33585 (3 log of $TCID_{50}$/mL). For 14 days post-challenge, all of the cats were monitored for clinical signs of disease, including elevated temperature, conjunctivitis serous discharge, conjunctivitis mucopurulent discharge, rhinitis serous discharge, rhinitis mucopurulent discharge, sneezing, audible rales, coughing, open-mouth breathing, anorexia, dehydration, one oral ulcer<4 mm, multiple oral ulcers, oral ulcers>4 mm, salivating, non-bleeding external ulcer, and bleeding external ulcers. Cats exhibiting severe clinical signs post-challenge that were consistent with calicivirus pathogenesis were euthanized.

As shown in TABLE 2-8, when compared to SQ/SQ vaccination, an SQ/Oral vaccination regimen decreased mortality from 44% to 10% and improved the median clinical score from 12 to 5.5 for cats vaccinated with FELOCELL® 4. Furthermore, adding the FCV-21 strain to FELOCELL® 3 and to FELOCELL® 4 resulted in no post-challenge mortality. Replacing the FCV-F9 strain of FELOCELL® 3 and FELOCELL® 4 with FCV-21 strain resulted in efficacy similar to vaccines containing both FCV-F9 and FCV-21, even for an Oral/Oral vaccination regime.

Table 2-8

Mortality of Cats Challenged with Virulent
FCV-33585 Following 2-Dose Vaccination with
Felocell 3 or 4, with or without FCV-F9 and/or
FCV-F21 (Example 2-7)

TABLE 2-8

| | Vaccination | | Challenge | | | | |
|---|---|---|---|---|---|---|---|
| | | | # | | Clinical Score | | |
| Group | Treatment | Route | Animals | Mortality, % | Median | Min. | Max. |
| T1 | Control | SQ/SQ | 9 | 78 | 24 | 2 | 35 |
| T2 | FELOCELL 4 | SQ/SQ | 9 | 44 | 12 | 3 | 38 |

TABLE 2-8-continued

| | Vaccination | | Challenge | | Clinical Score | | |
|---|---|---|---|---|---|---|---|
| Group | Treatment | Route | # Animals | Mortality, % | Median | Min. | Max. |
| T3 | FELOCELL 4 | SQ/Oral | 10 | 10 | 5.5 | 0 | 30 |
| T4 | FELOCELL 4 + FCV-21 | SQ/SQ | 10 | 0 | 1.5 | 0 | 13 |
| T5 | FELOCELL 4 + FCV-21 | SQ/Oral | 10 | 0 | 3.5 | 0 | 13 |
| T6 | FELOCELL 4A | SQ/SQ | 10 | 0 | 2.5 | 0 | 11 |
| T7 | FELOCELL 4A | SQ/Oral | 10 | 10 | 5 | 1 | 22 |
| T8 | FELOCELL 4A | Oral/Oral | 10 | 0 | 3 | 0 | 10 |
| T9 | FELOCELL 3 + FCV-21 | SQ/SQ | 10 | 0 | 2 | 0 | 8 |
| T10 | FELOCELL 3 + FCV-21 | SQ/Oral | 10 | 0 | 4 | 0 | 10 |
| T11 | FELOCELL 3A | Oral/Oral | 10 | 0 | 5 | 1 | 18 |

FELOCELL 4A: FELOCELL 4 without FCV-F9, but with FCV-21
FELOCELL 3A: FELOCELL 3 without FCV-F9, but with FCV-21

Example 2-8

Mortality and Clinical Scores for Cats Vaccinated with Three Doses of FELOCELL® 4 Components and Modified-Live FCV-21

Domestic shorthair cats, about 8 weeks of age, were administered vaccines containing modified-live feline rhinotracheitis virus (FHV), panleukopenia virus (FP), *Chlamydia psittaci*, and (1) FCV-F9 (FELOCELL® 4), (2) FCV-F9 and FCV-21 (FELOCELL® 4A), or (3) FCV-21 (FELOCELL® 4B). In each case, the cats were administered an initial subcutaneous vaccination followed by successive oral administrations on day 21 and day 42 (SQ/Oral/Oral). Each cat within the different dosing regimens (groups T1 to T4, 10 cats per group) received 1 mL of vaccine. Oral vaccination was achieved by administration of the vaccine into the mouth. On day 63, all cats were challenged with approximately 1 mL of virulent systemic FCV-33585 (3 log of $TCID_{50}$/mL). For 14 days post-challenge, all of the cats were monitored for clinical signs of disease as in EXAMPLE 2-7. Cats exhibiting severe clinical signs post-challenge that were consistent with calicivirus pathogenesis were euthanized. As shown in TABLE 2-9, the efficacy of the triple dose regimen, as measured by post-challenge mortality and clinical scores, is comparable to the efficacy of the double dose regimen described in EXAMPLE 2-7.

Table 2-9

Mortality of Cats Challenged with Virulent FCV-33585 Following 3-Dose Vaccination with FCV-F9 and/or FCV-F21 (Example 2-8)

TABLE 2-9

| | Vaccination | | Challenge | | Clinical Score | | |
|---|---|---|---|---|---|---|---|
| Group | Treatment | Route | # Animals | Mortality | Median | Min. | Max. |
| T1 | Control | SQ/Oral/Oral | 10 | 100% | 25 | 21 | 31 |
| T2 | FELOCELL 4 + FCV-21 | SQ/Oral/Oral | 10 | 0% | 5.5 | 0 | 17 |
| T3 | FELOCELL 4A | SQ/Oral/Oral | 9 | 0% | 4 | 0 | 10 |
| T4 | Felocell ® 4 | SQ/Oral/Oral | 10 | 30% | 10.5 | 1 | 30 |

FELOCELL 4A: FELOCELL 4 without FCV-F9, but with FCV-21

Example 2-9

Cross Neutralization Analysis of Sera from Cats Vaccinated with FELOCELL 4 Components with and without FCV-21

Serum samples from each cat in the study described in EXAMPLE 2-7 were collected following the second vaccination, but prior to challenge. The samples were heat treated at 56° C. for 30 minutes, and evaluated in the serum neutralization assay against each of 26 FCV strains as previously described in EXAMPLE 1-10 (TABLE 1-6).

Serum neutralization data were analyzed with cut-off titers of >23 and >15, and an average of the two cut-off titers was calculated (Ave). The results are shown in TABLE 2-10. The data indicate that the cross neutralization profile of FELOCELL 4 (containing FCV-F9) remains constant whether the route of administration is SQ/SQ or SQ/Oral. With the addition of FCV-21, however, the cross neutralization profile is greatly enhanced when the vaccine is administered SQ/SQ or SQ/Oral. Moreover, for FELOCELL 4A (containing FCV-21, but no FCV-F9), the cross neutralization profile is enhanced for SQ/SQ, SQ/Oral and even Oral/Oral vaccination routes.

TABLE 2-10

| Treatment | Vaccination | | | | Serum Collection | | Cross Neutralization | | |
|---|---|---|---|---|---|---|---|---|---|
| | # Animals | Days | Dose | Route | Days | # Animals | % (>23) | % (>15) | % (Ave) |
| Neg. control | 10 | 0 | 1 ml | SQ | 42 | 9 | 10.8 | 13.9 | 12.4 |
| | | 21 | 1 ml | SQ | | | | | |
| FELOCELL 4 | 10 | 0 | 1 ml | SQ | 42 | 9 | 38.5 | 42.3 | 40.4 |
| | | 21 | 1 ml | SQ | | | | | |
| FELOCELL 4 | 10 | 0 | 1 ml | SQ | 42 | 10 | 39.2 | 42.7 | 41.0 |
| | | 21 | 1 ml | Oral | | | | | |
| FELOCELL 4 + FCV-21 | 10 | 0 | 1 ml | SQ | 42 | 10 | 56.5 | 62.3 | 59.4 |
| | | 21 | 1 ml | SQ | | | | | |
| FELOCELL 4 + FCV-21 | 10 | 0 | 1 ml | SQ | 42 | 10 | 56.2 | 60 | 58.1 |
| | | 21 | 1 ml | Oral | | | | | |
| FELOCELL 4A* | 10 | 0 | 1 ml | SQ | 42 | 10 | 58.9 | 64.6 | 61.8 |
| | | 21 | 1 ml | SQ | | | | | |
| FELOCELL 4A* | 10 | 0 | 1 ml | SQ | 42 | 10 | 49.6 | 59.2 | 54.4 |
| | | 21 | 1 ml | Oral | | | | | |
| FELOCELL 4A* | 10 | 0 | 1 ml | Oral | 42 | 10 | 51.2 | 54.6 | 52.9 |
| | | 21 | 1 ml | Oral | | | | | |
| FELOCELL 3 + FCV-21 | 10 | 0 | 1 ml | SQ | 42 | 10 | 53.9 | 62.7 | 58.3 |
| | | 21 | 1 ml | SQ | | | | | |
| FELOCELL 3 + FCV-21 | 10 | 0 | 1 ml | SQ | 42 | 10 | 55.8 | 63.9 | 59.9 |
| | | 21 | 1 ml | Oral | | | | | |
| FELOCELL 3A** | 10 | 0 | 1 ml | Oral | 42 | 10 | 60.8 | 68.1 | 64.5 |
| | | 21 | 1 ml | Oral | | | | | |

*FELOCELL 4A: FELOCELL 4 without FCV-F9, but with FCV-21
**FELOCELL 3A: FELOCELL 3 without FCV-F9, but with FCV-21

In TABLE 2-11, the vaccination regimens evaluated included an initial subcutaneous vaccination followed by two oral booster immunizations on day 21 and day 42 (SQ/Oral/Oral). The results indicate that the addition of FCV-21, with or without FCV-F9 in FELOCELL 4, resulted in significantly broader cross neutralization profiles (approximate 40% increase).

TABLE 2-11

| Treatment | Vaccination | | | | | Serum Collection | | Cross Neutralization | | |
|---|---|---|---|---|---|---|---|---|---|---|
| | # animals | Days | Date | Dose | Route | Days | # Animals | % (>23) | % (>15) | % (Ave) |
| Neg. control | 10 | 0 | Feb. 15, 2005 | 1 ml | SQ | 63 | 10 | 5.8 | 10.4 | 8.1 |
| | | 21 | Mar. 8, 2005 | 1 ml | Oral | | | | | |
| | | 42 | Mar. 29, 2005 | 1 ml | Oral | | | | | |
| FELOCELL 4 + FCV-21 | 10 | 0 | Feb. 15, 2005 | 1 ml | SQ | 63 | 10 | 72.5 | 77.1 | 74.8 |
| | | 21 | Mar. 8, 2005 | 1 ml | Oral | | | | | |
| | | 42 | Mar. 29, 2005 | 1 ml | Oral | | | | | |
| FELOCELL 4A* | 10 | 0 | Feb. 15, 2005 | 1 ml | SQ | 63 | 9 | 72.5 | 76.7 | 74.6 |
| | | 21 | Mar. 8, 2005 | 1 ml | Oral | | | | | |
| | | 42 | Mar. 29, 2005 | 1 ml | Oral | | | | | |
| FELOCELL 4 | 10 | 0 | Feb. 15, 2005 | 1 ml | SQ | 63 | 10 | 49.6 | 57.9 | 53.8 |
| | | 21 | Mar. 8, 2005 | 1 ml | Oral | | | | | |
| | | 42 | Mar. 29, 2005 | 1 ml | Oral | | | | | |

*FELOCELL 4A: FELOCELL 4 without FCV-F9, but with FCV-21

We also disclose our finding that with the vaccines described herein as peptides, proteins, and DNA related to FCV strains FCV-21, FCV-49 and FCV 26391-4, oral or oronasal (ON) administration may be carried out in the first instance followed by a second oral or oronasal administration without the previously disclosed side effects mentioned above in EXAMPLE 2-4 and TABLE 2-5.

It should be noted that, as used in this specification and the appended claims, singular articles such as "a," "an," and "the," may refer to one object or to a plurality of objects unless the context clearly indicates otherwise. Thus, for example, reference to a composition containing "a compound" may include a single compound or two or more compounds.

It is to be understood that the above examples and descriptions is intended to be illustrative and not restrictive. Many embodiments will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

In TABLES 2-1 through 2-9, Felocell® 4, Felocell 4, or FELOCELL 4 or these words followed by the number "3" are vaccines where any variation of the name Felocell is owned by Pfizer. Reference to Felocell 4 A is Felocell 4 without FCV-F9, reference to Felocell 3 A is Felocell 3 without FCV-F9. Note, actual antigens used in these studies were not from the commercial product rather the antigens were prepared in small batches for research purposes only, but in the same manner as the commercial product.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Numbered description of the invention. Additional descriptions and examples. 1. A method of immunizing cats against feline calicivirus (FCV), the method comprising administering to a cat therapeutically effective amounts of first and second vaccines, wherein the first and second vaccines are adapted to induce an immune response in the cat against FCV, the first vaccine is administered parenterally and the second vaccine is administered orally or oronasally, and the second vaccine is administered N days following administration of the first vaccine, wherein N is an integer from 3 to 120 days, inclusive, also described is N of about 3 weeks and about 2-4 weeks. 2. The method of claim 1, wherein the vaccines independently comprise a live virus vaccine, a modified-live virus vaccine, an inactivated virus vaccine, a recombinant vaccine, a DNA vaccine, or a subunit antigen vaccine, either alone or in combination. 3. The method of claim 1, wherein at least one of the vaccines includes one or more strains of FCV. 4. The method of claim 3, wherein the one or more strains of FCV comprises F9 or FCV-21 or F9 and FCV-21. 5. The method of claim 1, wherein the vaccines are the same. 6. The method of claim 1, wherein at least one of the vaccines is also adapted to induce an immune response against one or more pathogens selected from feline herpesvirus, feline leukemia virus, feline immunodeficiency virus, feline panleukopenia virus, and feline *Chlamydia*. 7. The method of claim 1, wherein the first vaccine is administered subcutaneously. 8. The method of claim 1, wherein the second vaccine is administered perorally or oronasally. 9. The method of claim 1, wherein the second vaccine or a subsequent vaccine is administered after the cat has developed an FCV serum neutralization titer of about 1:6 or greater. 10. A method as in any of claims 1 to 9, further comprising administering to the cat a therapeutically effective amount of a third vaccine, wherein the third vaccine is adapted to induce an immune response in the cat against FCV and is administered parenterally, orally, or oronasally M days following administration of the first or the second vaccine, wherein M is an integer from 1 to 120, inclusive. 11. The method of claim 10, wherein the third vaccine is administered subcutaneously. 12. A method of immunizing cats against feline calicivirus (FCV), the method comprising administering to a cat therapeutically effective amounts of first and second vaccines, wherein the first and second vaccines are adapted to induce an immune response in the cat against FCV, wherein the first vaccine is administered orally or oronasally and the second vaccine is administered orally or oronasally, and the second vaccine is administered N days following administration of the first vaccine, wherein N is an integer from 3 to 120, inclusive, also specified is N about 3 weeks and about 2-4 weeks. 13. The method of claim 12 wherein the FCV strain is selected from the group consisting of FCV-21, FCV-49, FCV 26391-4. 14. A method of immunizing animals comprising administering to an animal a therapeutically effective amounts of first and second vaccines, with an optional third vaccine, wherein the first and second and optional third vaccines are adapted to induce an immune response and the first vaccine is administered parenterally or orally, the second vaccine is administered orally or oronasally, and the second and optional third vaccine is administered N days following administration of the first vaccine, wherein N is an integer from 3 to 120, inclusive, also specified is N about 3 weeks and about 2-4 weeks, and the method may include optional annual booster administrations of the vaccine, including an M period of about a year.

Part 3

This Part Provides Methods and Compositions for Immunizing Animals Against Feline Parvovirus (FPV) and Feline Herpes Virus (FHV)

Described herein are methods and materials for treating and immunizing animals with vaccine, and in particular cats against feline respiratory disease caused by feline calicivirus (FCV), feline panleukopenia caused by Feline Parvovirus (FPV), feline vial rhinotracheitis caused by feline hepesvirus (FHV), which has also been called Feline Rhinotracheitis Virus. Described below are novel combinations of vaccines, that when presented to a feline in the manner described allow for effective single oral and oral/oral and subq/oral deliveries of both FPV and or FHV vaccines.

Single oral means a single oral delivery that confers effective protection to a vaccinated animal. By oral/oral is meant an oral delivery given twice, similar to the description above in Part 2, i.e. either oral followed by some period of time and then another dose is given via the oral route, and subq/oral is a first dose given subq followed by some period of time and then another dose is given via oral route.

What is described here is the delivery of the combination of modified live FPV and/or modified live FHV in combination with modified live *Chlamydia* vaccine, or any components of modified live *Chlamydia* vaccine, e.g. growth medium, cell lysate or whole cells, any components of *Chlamydia* itself. *Chlamydia* is also referred to as Feline *Chlamydia*, or Feline *Chlamydia psittaci* or FCp.

When modified live FPV is given by itself or in combination with modified live FCV, or modified live FHV vaccines, the FPV is not effective when delivered in an oral/oral manner, and shows a decreased SN titer with SQ/oral route of administration. Similarly, when modified live FHV is given by itself or in combination with modified live FCV, or with modified live FPV vaccine, FHV is not effective when delivered in an oral/oral manner, and with shows a decreased efficacy with SQ/oral route of administration. Only when either FPV and/or FHV is given in combination with a modified live *Chlamydia* vaccine, an adequate protection against FPV and/or FHV is provided, when the delivery of the combination vaccines is either through a subq/oral or oral/oral route.

According to the above the following Examples are provided. The following examples are intended to be illustrative and non-limiting, and represent a few specific embodiments of the present invention.

Example 3-1 (Notional)

SUBQ/ORAL VACCINATION REGIMEN WITH FPV AND *CHLAMYDIA*. FPV and *Chlamydia* (or any components of modified live *Chlamyida* vaccine) is provided in a combination vaccine with or without other components. The modified live vaccines may be delivered subq/oral.

Example 3-2 (Notional)

ORAL/ORAL VACCINATION REGIMEN WITH FPV AND *CHLAMYDIA*. FPV and *Chlamydia* (or any components of modified live *Chlamyida* vaccine) is provided in a combination vaccine with or without other components. The modified live vaccines may be delivered oral/oral.

Example 3-3 (Notional)

SUBQ/ORAL VACCINATION REGIMEN WITH FPV, FHV AND *CHLAMYDIA*. FPV, FHV and *Chlamydia* (or any components of modified live *Chlamyida* vaccine) is provided in a combination vaccine with or without other components. The modified live vaccines may be delivered subq/oral.

Example 3-4 (Notional)

ORAL/ORAL VACCINATION REGIMEN WITH FPV, FHV AND *CHLAMYDIA*. FPV, FHV and *Chlamydia* (or any components of modified live *Chlamyida* vaccine) is provided in a combination vaccine with or without other components. The modified live vaccines may be delivered oral/oral.

Example 3-5 (Actual)

SUBQ/ORAL VACCINATION REGIMEN WITH FPV, FHV, FCV AND *CHLAMYDIA*. FPV, FHV, FCV and *Chlamydia* (or any components of modified live *Chlamyida* vaccine) is provided in a combination vaccine with or without other components. The modified live vaccines may be delivered oral/oral (Table 3-1).

Example 3-6 (Actual)

ORAL/ORAL VACCINATION REGIMEN WITH FPV, FHV, FCV AND *CHLAMYDIA*. FPV, FHV, FCV and *Chlamydia* (or any components of modified live *Chlamyida* vaccine) is provided in a combination vaccine with or without other components. The modified live vaccines may be delivered oral/oral. See Table 3-1.

Domestic shorthair cats, about 8 weeks of age, were vaccinated with FELOCELL 4A and 3A components which contain modified-live feline rhiotracheitis virus [FHV], calicivirus [FCV-21], panleukopenia virus [FPV] and *Chlamydia psittaci* [FCp]. The vaccination regimens evaluated included: an initial subcutaneous vaccination followed by subcutaneous boosts on days 21 (SQ/SQ); an initial subcutaneous vaccination followed by one oral booster immunization on day 21 (SQ/Oral); or an initial oral vaccination followed by a second oral vaccination on day 21. Oral vaccination was achieved by administration of the vaccine into the mouth. Serum samples from each cat were collected post second vaccination, and heat treated at 56° C. for 30 minutes. The samples were evaluated in the serum neutralization assay against FPV.

TABLE 3-1

| Vaccine | Route | FPV SN Titer |
| --- | --- | --- |
| FELOCELL 4A | SQ/SQ | 4096 |
| FELOCELL 4A | SQ/Oral | 7276 |
| FELOCELL 4A | Oral/Oral | 5793 |
| FELOCELL 3A | Oral/Oral | 7 |

FELOCELL 4A: FPV/FHV/FCV-21/FCp
FELOCELL 3A: FPV/FHV/FCV-21

The results from TABLE 3-1 suggest that cats responded minimally to the FPV antigen, as reported previously in the literature. (Absence of an immune response after oral administration of attenuated feline panleukopenia virus. Schults R D, Scott F W, Infect Immun. 1973, Apr. 7 (4): 547-9). With the presence of *Chlamydia*, however, or any components associated with a *Chlamydia* vaccine, the FPV SN titers were much higher, suggesting in vivo efficacy against FPV challenge. Moreover, we have observed the enhanced FPV immunigenicity not only with SQ/SQ, SQ/Oral, but also with Oral/Oral group.

Example 3-7 (Actual)

ORAL/ORAL VACCINATION REGIMEN WITH FPV, FHV, FCV FPV, FHV and FCV are provided in a combination vaccine with or without other components. The modified live vaccines may be delivered oral/oral. See Table 3-2.

Domestic shorthair cats, about 8 weeks of age, were vaccinated with FELOCELL 3A, which contains modified-live feline rhiotracheitis virus [FHV], calicivirus [FCV-21] and panleukopenia virus [FPV]. The vaccination regimens evaluated included: an initial subcutaneous vaccination followed by subcutaneous boosts on days 21 (SQ/SQ); an initial subcutaneous vaccination followed by one oral booster immunization on day 21 (SQ/Oral); or an initial oral vaccination followed by a second oral vaccination on day 21. Oral vaccination was achieved by administration of the vaccine into the mouth. Serum samples from each cat were collected post first and second vaccination and heat treated at 56° C. for 30 minutes. The samples were analyzed in the serum neutralization assay against FPV.

TABLE 3-2

| | | | FPV-FPN SN Titer | |
| --- | --- | --- | --- | --- |
| Group | Treatment | Route | Post 1st vax | Post 2nd vax |
| T01 | unvaccinated | N/A | 1 | 1 |
| T02 | FELOCELL 3A | SQ/SQ | 16618 | 54319 |
| T03 | FELOCELL 3A | SQ/Oral | 20346 | 28771 |
| T04 | FELOCELL 3A | Oral/Oral | 1 | 4 |

The results from TABLE 3-2 suggest that the FPV antigen present in the FELOCELL 3A vaccine induced minimal immune response when given Oral/Oral (consistent with results from TABLE 3-1). When the vaccines were given SQ/SQ or SQ/Oral, however, high FPV SN titers were observed, an indication of in vivo efficacy.

Numbered description of the invention. Additional descriptions and examples. Note below, FCV is Feline Calicivirus, FPV is Feline Parvovirus, which has also been called Panleukopenia, or FPL and finally, FHV is Feline Herpes Virus 1. An immunogenic composition, comprising both modified live FPV and modified live *Chlamydia* administered in a single administrative dosage. 2. A vaccine, comprising modified live FPV and modified live *Chlamydia* delivered to a feline in two separate single administrative dosages, the single administrative dosages both delivered by oral or oralnasal routes and separated in time by 3 to 120 days, or about 3 weeks or about 2 weeks. 3. A method of immunizing cats against FPV, the method comprising administering to a cat therapeutically effective amounts of first and second vaccines, wherein the first and second vaccines are adapted to induce an immune response in the cat against FPV, the first vaccine is administered orally or oronasally and the second vaccine is administered orally or oronasally, the second vaccine is administered N days following administration of the first vaccine, wherein N is an integer from 3 to 120, inclusive, or where N is about 3 weeks or where N is about 2 weeks, wherein said first and second vaccine are comprised of both a modified live FPV and modified live *Chlamydia*. 4. An immunogenic composition, comprising both modified live FHV and modified live *Chlamydia* administered in a single administrative dosage. 5. A vaccine, comprising modified live FHV and modified live *Chlamydia* delivered to a feline in two separate single administrative dosages, the single administrative dosages both delivered by oral or oralnasal routes and separated in time by 3 to 120 days, or about 3 weeks or about 2 weeks. 6. A method of immunizing cats FHV the method comprising administering to a cat therapeutically effective amounts of first and second vaccines, wherein the first and second vaccines are adapted to induce an immune response in the cat against FHV, the first vaccine is administered orally or oronasally and the second vaccine is administered orally or oronasally, the second vaccine is administered N days following administration of the first vaccine, wherein N is an integer from 3 to 120, inclusive, or where N is about 3 weeks or where N is about 2 weeks, wherein said first and second vaccine are comprised of both a modified live FHV and modified live *Chlamydia*. 7. An immunogenic composition, comprising both modified live FCV and modified live *Chlamydia* administered in a single administrative dosage. 8. A vaccine, comprising modified live FCV and modified live *Chlamydia* delivered to a feline in two separate single administrative dosages, the single administrative dosages both delivered by oral or oralnasal routes and separated in time by 3 to 120 days, or about 3 weeks or about 2 weeks. 9. A method of immunizing cats against FCV the method comprising administering to a cat therapeutically effective amounts of first and second vaccines, wherein the first and second vaccines are adapted to induce an immune response in the cat against FCV, the first vaccine is administered orally or oronasally and the second vaccine is administered orally or oronasally, the second vaccine is administered N days following administration of the first vaccine, wherein N is an integer from 3 to 120, inclusive, or where N is about 3 weeks or where N is about 2 weeks, wherein said first and second vaccine are comprised of both a modified live FCV and modified live *Chlamydia*. 10. An immunogenic composition, comprising modified live FPV, modified live FHV and modified live *Chlamydia* administered in a single administrative dosage. 11. A vaccine, comprising modified live FPV, modified live FHV and modified live *Chlamydia* delivered to a feline in two separate single administrative dosages, the single administrative dosages both delivered by oral or oralnasal routes and separated in time by 3 to 120 days, or about 3 weeks or about 2 weeks. 12. A method of concurrently immunizing cats against FPV and FHV, the method comprising administering to a cat therapeutically effective amounts of first and second vaccines, wherein the first and second vaccines are adapted to induce an immune response in the cat against FPV and FHV, the first vaccine is administered orally or oronasally and the second vaccine is administered orally or oronasally, the second vaccine is administered N days following administration of the first vaccine, wherein N is an integer from 3 to 120, inclusive, or where N is about 3 weeks or where N is about 2 weeks, wherein said first and second vaccine comprising modified live FPV, modified live FHV and modified live *Chlamydia*. 13. An immunogenic composition, comprising modified live FPV, modified live FCV and modified live *Chlamydia* administered in a single administrative dosage. 14. A vaccine, comprising modified live FPV, modified live FCV and modified live *Chlamydia* delivered to a feline in two separate single administrative dosages, the single administrative dosages both delivered by oral or oralnasal routes and separated in time by 3 to 120 days, or about 3 weeks or about 2 weeks. 15. A method of concurrently immunizing cats against FPV and FCV, the method comprising administering to a cat therapeutically effective amounts of first and second vaccines, wherein the first and second vaccines are adapted to induce an immune response in the cat against FPV and FHV, the first vaccine is administered orally or oronasally and the second vaccine is administered orally or oronasally, the second vaccine is administered N days following administration of the first vaccine, wherein N is an integer from 3 to 120, inclusive, or where N is about 3 weeks or where N is about 2 weeks, wherein said first and second vaccine comprising modified live FPV, modified live FHV and modified live *Chlamydia*. 16. An immunogenic composition, comprising modified live FHV, modified live FCV and modified live *Chlamydia* administered in a single administrative dosage. 17. A vaccine, comprising modified live FHV, modified live FCV and modified live *Chlamydia* delivered to a feline in two separate single administrative dosages, the single administrative dosages both delivered by oral or oralnasal routes and separated in time by 3 to 120 days, or about 3 weeks or about 2 weeks. 18. A method of concurrently immunizing cats against FHV and FCV, the method comprising administering to a cat therapeutically effective amounts of first and second vaccines, wherein the first and second vaccines are adapted to induce an immune response in the cat against FHV and FCV, the first vaccine is administered orally or oronasally and the second vaccine is administered orally or oronasally, the second vaccine is administered N days following administration of the first vaccine, wherein N is an integer from 3 to 120, inclusive, or where N is about 3 weeks or where N is about 2 weeks, wherein said first and second vaccine comprising modified live FHV, modified live FCV and modified live *Chlamydia*. 19. An immunogenic composition, comprising modified live FPV, modified live FHV, modified live FCV and modified live *Chlamydia* administered in a single administrative dosage. 20. A vaccine, comprising modified live FPV, modified live FHV, modified live FCV and modified live *Chlamydia* delivered to a feline in two separate single administrative dosages, the single administrative dosages both delivered by oral or oralnasal routes and separated in time by 3 to 120 days, or about 3 weeks or about 2 weeks. 21. A method of concurrently immunizing cats against FPV, FHV and FCV, the method comprising administering to a cat therapeutically effective amounts of first and second vaccines, wherein the first and second vaccines are adapted to induce an immune response in the cat against FPV, the first vaccine is administered orally or oronasally and the second vaccine is administered orally or oronasally, the second vaccine is administered N days following administration of the first vaccine, wherein N is an integer from 1 to 120, inclusive, or where N is about 3 weeks or where N is about 2 weeks, wherein said first and second vaccine comprising modified live FPV, modified live FHV, modified live FCV and modified live *Chlamydia*.

Deposit of Biological Material

The following materials have been deposited with the American Type Culture Collection (the "ATCC"), 10801 University Blvd., Manassas, Va., 20110, USA on Feb. 1, 2006.

Feline calicivirus UC 25504, strain FCV-21, ATCC designation PTA-7346;

Feline calicivirus UC 25505, strain FCV-49, ATCC designation PTA-7347; and

Feline calicivirus UC 25506, strain FCV-26391-4, ATCC designation PTA-7348.

These deposits were made under the provisions of the Budapest Treaty on the International Recognition of the Deposit of Microorganisms for the Purpose of Patent Procedure (copy of depository receipt of record in the file herein). This assures maintenance of a viable culture of the deposits for 30 years from the date of deposit, and assures permanent and unrestricted availability of the culture to the public upon issuance of the pertinent U.S. Patent, and pursuant to 35 USC section 122 and the Commissioner's rules pursuant thereto, assures availability to anyone entitled thereto, as determined by the U.S. Commissioner of Patents. The assignee of the present application has also agreed that if the materials on deposit should become unviable, the materials will be promptly replaced, although such availability is not to be construed as a license to practice the invention claimed herein in contravention of the patent laws of the United States.

The invention claimed is:

1. A vaccine for immunizing cats against feline calicivirus that comprises FCV-21 capsid protein and a pharmaceutically acceptable carrier, wherein said FCV-21 capsid protein is selected from the group consisting of:
   (a) SEQ ID NO:13; and
   (b) a polypeptide having at least 95% sequence identity to SEQ ID NO:13.

2. The vaccine of claim 1, further comprising an adjuvant.

3. The vaccine of claim 1, wherein said FCV-21 capsid protein is provided in said vaccine as a live, live attenuated, or inactivated FCV-21 virus.

4. The vaccine of claim 1, further comprising an additional live, attenuated, or inactivated FCV strain, or a component thereof.

5. The vaccine of claim 1, wherein said FCV-21 capsid protein has at least 99% sequence identify to SEQ ID NO:13.

6. The vaccine of claim 4, wherein said additional live, attenuated, or inactivated FCV strain, or component thereof, is selected from the group consisting of FCV-F9, FCV-LLK, FCV-M8, FCV-255, and FCV-2280.

* * * * *

SEQUENCE LISTING

```
<160> NUMBER OF SEQ ID NOS: 17

<210> SEQ ID NO 1
<211> LENGTH: 29
<212> TYPE: DNA
<213> ORGANISM: Feline calicivirus

<400> SEQUENCE: 1
ggctaggatc catgtgctca acctgcgct                                        29

<210> SEQ ID NO 2
<211> LENGTH: 32
<212> TYPE: DNA
<213> ORGANISM: feline calicivirus

<400> SEQUENCE: 2
gccattctag attttttttt tttccctggg gt                                    32

<210> SEQ ID NO 3
<211> LENGTH: 24
<212> TYPE: DNA
<213> ORGANISM: feline calicivirus

<400> SEQUENCE: 3
gtggaggcgc ggtctgacca gatc                                             24

<210> SEQ ID NO 4
<211> LENGTH: 23
<212> TYPE: DNA
<213> ORGANISM: feline calicivirus

<400> SEQUENCE: 4
atcacagcac ccgagcaagg aac                                              23

<210> SEQ ID NO 5
<211> LENGTH: 25
<212> TYPE: DNA
<213> ORGANISM: feline calicivirus

<400> SEQUENCE: 5
tgtttgatgc tcgtcaggtg gaacc                                            25

<210> SEQ ID NO 6
<211> LENGTH: 24
<212> TYPE: DNA
```

-continued

<213> ORGANISM: feline calicivirus

<400> SEQUENCE: 6
gtaccacctt atgtctgaca ctga                                          24

<210> SEQ ID NO 7
<211> LENGTH: 23
<212> TYPE: DNA
<213> ORGANISM: feline calicivirus

<400> SEQUENCE: 7
attcggccgt tgtcttcca agc                                            23

<210> SEQ ID NO 8
<211> LENGTH: 23
<212> TYPE: DNA
<213> ORGANISM: feline calicivirus

<400> SEQUENCE: 8
ctttctgcct cctacatggg aat                                           23

<210> SEQ ID NO 9
<211> LENGTH: 22
<212> TYPE: DNA
<213> ORGANISM: feline calicivirus

<400> SEQUENCE: 9
gtgtatgagt aagggtcaac cc                                            22

<210> SEQ ID NO 10
<211> LENGTH: 23
<212> TYPE: DNA
<213> ORGANISM: feline calicivirus

<400> SEQUENCE: 10
gcttggaaga caaacggccg aat                                           23

<210> SEQ ID NO 11
<211> LENGTH: 29
<212> TYPE: DNA
<213> ORGANISM: feline calicivirus

<400> SEQUENCE: 11
tgtacccttt gctcaagaat tttgttaaa                                     29

<210> SEQ ID NO 12
<211> LENGTH: 2007
<212> TYPE: DNA
<213> ORGANISM: feline calicivirus

<400> SEQUENCE: 12
atgtgctcaa cctgcgctaa cgtgcttaaa tactatgatt gggatcctca ctttagattg       60
attatcaacc ccaacaagtt tctctctgtt ggcttctgtg ataatccact tatgtgttgc      120
taccctgaac tacttcctga atttggaact gtgtgggact gtgaccagtc accacttcaa      180
atctacttag agtctattct cggggatgat gagtgggctt gcactcatga agcagtagac      240
ccagtggtgc cgccaatgca ttgggatagt gctggcaaga tcttccagcc acatcctggc      300
gtattgatgc accatctgat tggtgaagtt gccaaggcct gggatccaaa cttgccactc      360
tttcgtctgg aagcagatga tggatccatt acaacgcctg aacaaggaac actagttggc      420
ggggttattg ctgaacccag tgctcaaatg tcatcagctg ctgacatggc cacagggaaa      480

-continued

```
acagttgatt ctgagtggga ggctttcttc tcctttcaca ctagtgtcaa ctggagtaca    540
tctgaaactc aagggaagat tcttttcaag cagactttgg gacccctact taacccttac    600
ctaacccatc tcgctaagct ttatgttgct tggtctggct ctgttgaagt taggttttct    660
atttctgggt ccggcgtatt tggagggaag ctggcggcaa ttgttgtacc cccaggggtt    720
gaccccattc agagtacctc aatgctacag taccctcatg ttctgttcga cgctcgccaa    780
gtggagcctg taatcttttc tatccctgat ttgagaagta cactgtatca ccttatgtct    840
gacaccgata ctacatctct tgtaatcatg gtgtacaatg atctcattaa tccctatgcc    900
aatgattcaa attcttctgg gtgtattgtt accgttgaaa ctaaaccagg acctgacttc    960
aagtttcatt tactgaaacc ccctggatct atgttaactc acggatcagt cccttctgat   1020
ctaatcccta agtcttcctc cctttggatt ggtaatcggt attggtctga tataacggat   1080
tttgtgattc ggcctttcgt atttcaggca aacaggcact ttgacttcaa tcaggagact   1140
gcaggatgga gcaccccaag gtttcgacct atcacagtca cactcagtgt gaaggatgcc   1200
gcaaagttgg gcactgcaat cgctactgac tacattgtcc caggcatacc agatggctgg   1260
cctgacacaa caattgctga gcagctcaca cctgctggtg attacgctat caccaatgat   1320
tctggtaatg atattacaac tgctgccgga tatgactctg ctactgtgat caaaaatgac   1380
acaaacttta ggggcatgta catttgtggt tctctccaaa gggcctgggg tgataagaaa   1440
atttcgaata ctgctttcat caccactgca acggttgatg gcaacaggct gaaaccatgc   1500
aataccatcg accagagcaa aattgctata ttccaagaca cccatgccaa tgaaggagtc   1560
caaacctctg atgatacact ggccttgctt ggctatactg gaattggtga agaagcaatt   1620
ggctccgatc gggacagggt ggtacgaatt agcgtgctcc cagaagctgg tgcccgaggt   1680
ggtaatcacc cgatcttcta caaaaattca atcaaacttg gatatgtaat taggtccatt   1740
gatgtgttca attcccaaat tctacataca tcaagacagt tgtccctcaa ccattacctg   1800
ttatcaccag actcttttgc tgtttacagg attacagatt ctaatggttc ttggtttgac   1860
ataggcattg atagtgaagg tttttctttt gttggtgttt caagcattgg gaaactggag   1920
tttcctctca ccgcctccta catgggaatt caactggcga agattcgact cgcctcaaat   1980
attaggagtg tgaagaccag aatatga                                       2007
```

<210> SEQ ID NO 13
<211> LENGTH: 668
<212> TYPE: PRT
<213> ORGANISM: feline calicivirus

<400> SEQUENCE: 13

```
Met Cys Ser Thr Cys Ala Asn Val Leu Lys Tyr Tyr Asp Trp Asp Pro
1               5                   10                  15

His Phe Arg Leu Ile Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Ala Cys Thr His Glu Ala Val Asp
65                  70                  75                  80

Pro Val Val Pro Pro Met His Trp Asp Ser Ala Gly Lys Ile Phe Gln
                85                  90                  95
```

-continued

```
Pro His Pro Gly Val Leu Met His His Leu Ile Gly Glu Val Ala Lys
            100                 105                 110
Ala Trp Asp Pro Asn Leu Pro Leu Phe Arg Leu Glu Ala Asp Asp Gly
        115                 120                 125
Ser Ile Thr Thr Pro Glu Gln Gly Thr Leu Val Gly Gly Val Ile Ala
    130                 135                 140
Glu Pro Ser Ala Gln Met Ser Ser Ala Ala Asp Met Ala Thr Gly Lys
145                 150                 155                 160
Thr Val Asp Ser Glu Trp Glu Ala Phe Phe Ser Phe His Thr Ser Val
                165                 170                 175
Asn Trp Ser Thr Ser Glu Thr Gln Gly Lys Ile Leu Phe Lys Gln Thr
            180                 185                 190
Leu Gly Pro Leu Leu Asn Pro Tyr Leu Thr His Leu Ala Lys Leu Tyr
        195                 200                 205
Val Ala Trp Ser Gly Ser Val Glu Val Arg Phe Ser Ile Ser Gly Ser
    210                 215                 220
Gly Val Phe Gly Gly Lys Leu Ala Ala Ile Val Pro Pro Gly Val
225                 230                 235                 240
Asp Pro Ile Gln Ser Thr Ser Met Leu Gln Tyr Pro His Val Leu Phe
                245                 250                 255
Asp Ala Arg Gln Val Glu Pro Val Ile Phe Ser Ile Pro Asp Leu Arg
            260                 265                 270
Ser Thr Leu Tyr His Leu Met Ser Asp Thr Asp Thr Ser Leu Val
        275                 280                 285
Ile Met Val Tyr Asn Asp Leu Ile Asn Pro Tyr Ala Asn Asp Ser Asn
    290                 295                 300
Ser Ser Gly Cys Ile Val Thr Val Glu Thr Lys Pro Gly Pro Asp Phe
305                 310                 315                 320
Lys Phe His Leu Leu Lys Pro Pro Gly Ser Met Leu Thr His Gly Ser
                325                 330                 335
Val Pro Ser Asp Leu Ile Pro Lys Ser Ser Leu Trp Ile Gly Asn
            340                 345                 350
Arg Tyr Trp Ser Asp Ile Thr Asp Phe Val Ile Arg Pro Phe Val Phe
        355                 360                 365
Gln Ala Asn Arg His Phe Asp Phe Asn Gln Glu Thr Ala Gly Trp Ser
    370                 375                 380
Thr Pro Arg Phe Arg Pro Ile Thr Val Thr Leu Ser Val Lys Asp Ala
385                 390                 395                 400
Ala Lys Leu Gly Thr Ala Ile Ala Thr Asp Tyr Ile Val Pro Gly Ile
                405                 410                 415
Pro Asp Gly Trp Pro Asp Thr Thr Ile Ala Glu Gln Leu Thr Pro Ala
            420                 425                 430
Gly Asp Tyr Ala Ile Thr Asn Asp Ser Gly Asn Asp Ile Thr Thr Ala
        435                 440                 445
Ala Gly Tyr Asp Ser Ala Thr Val Ile Lys Asn Asp Thr Asn Phe Arg
    450                 455                 460
Gly Met Tyr Ile Cys Gly Ser Leu Gln Arg Ala Trp Gly Asp Lys Lys
465                 470                 475                 480
Ile Ser Asn Thr Ala Phe Ile Thr Thr Ala Thr Val Asp Gly Asn Arg
                485                 490                 495
Leu Lys Pro Cys Asn Thr Ile Asp Gln Ser Lys Ile Ala Ile Phe Gln
            500                 505                 510
Asp Thr His Ala Asn Glu Gly Val Gln Thr Ser Asp Asp Thr Leu Ala
```

-continued

```
            515                 520                 525
Leu Leu Gly Tyr Thr Gly Ile Gly Glu Glu Ala Ile Gly Ser Asp Arg
        530                 535                 540

Asp Arg Val Val Arg Ile Ser Val Leu Pro Glu Ala Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Ser Pro Asp Ser Phe Ala Val
        595                 600                 605

Tyr Arg Ile Thr Asp Ser Asn Gly Ser Trp Phe Asp Ile Gly Ile Asp
610                 615                 620

Ser Glu Gly Phe Ser Phe Val Gly Val Ser Ser Ile Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Val Lys Thr Arg Ile
            660                 665
```

<210> SEQ ID NO 14
<211> LENGTH: 2007
<212> TYPE: DNA
<213> ORGANISM: feline calicivirus

<400> SEQUENCE: 14

```
atgtgctcaa cctgcgctaa cgtgcttaaa tattatgatt gggaccccca cttcaagttg      60
attatcaacc ccaacaaatt tctctctgtt ggcttttgtg ataatcccct tatgtgttgt     120
taccctgagt tgcttccaga atttggaact gtgtgggatt gtgaccagtc accactgcaa     180
atttacttgg agtctatcct ggagatgat gaatggagct ccacttatga agcaatagac      240
ccagtagcgc caccaatgca ttgggatagt gctggcaaga tctttcagcc catcccggt      300
gtgttgatgc actacttgat tggtgaggtt gctagggcct gggatccaag tttgccaacc     360
tttcgtctgg aagcagatga tggatctatc acaacgcctg agcaaggaac actagtcggt     420
ggggtcattg ctgaacccag tgcccaaatg tcaactgctg ctgatatggc cacagggaaa     480
accgttgact ctgagtggga ggctttcttt tccttccaca ccagcgtcaa ctggagcaca     540
tctgaaactc aagggaagat tcttttcaaa caatcattgg acctctact aaatccctac     600
ttaacccatc ttgcaaagct ctacgttgct tggtctggtt ctgttgaggt taggttttct     660
atttctggat ctggtgtatt cggggggcaag cttgcagcaa tgttgtgcc accagggggtt    720
gatcctgttc agagcacttc aatgctacag taccccccatg ttctgtttga tgcccgccaa    780
gtagagcctg tcattttcac tattcctgac ttgagaagca ccctgtatca tcttatgtct    840
gatactgaca ctacctctct tgtaatcatg gtgtataacg atcttatcaa cccttatgct     900
aatgattcaa attcatctgg ctgtattgtc actgttgaaa caaaacccgg ccctgatttc    960
aaatttcatc tgctgaagcc cccaggatct atgctaacac atggttcagt gccatcagat   1020
ctgatcccaa atcttcttc gctttggatt ggtaatcggt attggtctga taactgac      1080
ttcgttattc gccccttcgt gtttcaagca aatagacact tgatttcaa tcaggaaact    1140
gccggttgga gcaccccacg gtttcggccc attacagtta cacttagtgt gaaggaatcc   1200
gcaaaattgg gtactgcaat tgccaccgat tacatcgtcc caggcatacc agatggctgg   1260
```

-continued

```
cctgacacga cagttgctga ggagctcaca cccgctggtg attacgccat cactaatgag      1320
actggcaacg acattacaac cgctgctagt tatgattctg ccagtgcaat caagaataca      1380
accaacttta gaggcatgta tatttgtggt tcccttcaaa gagcctgggg tgacaagaag      1440
atttcaaaca ctgcttttat caccactgga acggttagcg acaacaaatt aaaaccatcc      1500
aacatcattg accaaagtaa gatagctgta tttcaggaca cgcatgccaa taaggaagtt      1560
caaacatctg atgatacatt agccttactt ggctatactg gaattggcga agaagcaatt      1620
ggggctgatc gggacagagt agtgcgaatc agtgtgctcc agaagctggt gcccgtggt      1680 ggtaaccacc caatttctct caagaattcc attaaacttg gatacgtaat tagatctatt      1740
gatgtattca attcccagat tttgcacaca tcaagacaac tttcccttaa tcattatttg      1800
ttatcaccag actcttttgc tgtttacaga atcacagact ccaatggatc atggtttgac      1860
ataggtattg atagtgaagg ttttttcttt gttggtgttt caaatattgg aaaattagag      1920
tttccccttg ctgcctccta catgggaatt cagctggcga aaattcggct cgcctcaaat      1980
attaggagta gtatgaccaa aatatga                                          2007
```

<210> SEQ ID NO 15
<211> LENGTH: 668
<212> TYPE: PRT
<213> ORGANISM: feline calicivirus

<400> SEQUENCE: 15

```
Met Cys Ser Thr Cys Ala Asn Val Leu Lys Tyr Tyr Asp Trp Asp Pro
1               5                   10                  15

His Phe Lys Leu Ile Ile Asn Pro Asn Lys Phe Leu Ser Val Gly Phe
                20                  25                  30

Cys Asp Asn Pro Leu Met Cys Cys Tyr Pro Glu Leu Leu Pro Glu Phe
            35                  40                  45

Gly Thr Val Trp Asp Cys Asp Gln Ser Pro Leu Gln Ile Tyr Leu Glu
        50                  55                  60

Ser Ile Leu Gly Asp Asp Glu Trp Ser Ser Thr Tyr Glu Ala Ile Asp
65                  70                  75                  80

Pro Val Ala Pro Pro Met His Trp Asp Ser Ala Gly Lys Ile Phe Gln
                85                  90                  95

Pro His Pro Gly Val Leu Met His Tyr Leu Ile Gly Glu Val Ala Arg
            100                 105                 110

Ala Trp Asp Pro Ser Leu Pro Thr Phe Arg Leu Glu Ala Asp Asp Gly
        115                 120                 125

Ser Ile Thr Thr Pro Glu Gln Gly Thr Leu Val Gly Gly Val Ile Ala
    130                 135                 140

Glu Pro Ser Ala Gln Met Ser Thr Ala Ala Asp Met Ala Thr Gly Lys
145                 150                 155                 160

Thr Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Thr His Leu Ala Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240
```

-continued

```
Asp Pro Val Gln Ser Thr Ser Met Leu Gln Tyr Pro His Val Leu Phe
                245                 250                 255
Asp Ala Arg Gln Val Glu Pro Val Ile Phe Thr Ile Pro Asp Leu Arg
            260                 265                 270
Ser Thr Leu Tyr His Leu Met Ser Asp Thr Asp Thr Ser Leu Val
        275                 280                 285
Ile Met Val Tyr Asn Asp Leu Ile Asn Pro Tyr Ala Asn Asp Ser Asn
    290                 295                 300
Ser Ser Gly Cys Ile Val Thr Val Glu Thr Lys Pro Gly Pro Asp Phe
305                 310                 315                 320
Lys Phe His Leu Leu Lys Pro Pro Gly Ser Met Leu Thr His Gly Ser
                325                 330                 335
Val Pro Ser Asp Leu Ile Pro Lys Ser Ser Leu Trp Ile Gly Asn
            340                 345                 350
Arg Tyr Trp Ser Asp Ile Thr Asp Phe Val Ile Arg Pro Phe Val Phe
        355                 360                 365
Gln Ala Asn Arg His Phe Asp Phe Asn Gln Glu Thr Ala Gly Trp Ser
    370                 375                 380
Thr Pro Arg Phe Arg Pro Ile Thr Val Thr Leu Ser Val Lys Glu Ser
385                 390                 395                 400
Ala Lys Leu Gly Thr Ala Ile Ala Thr Asp Tyr Ile Val Pro Gly Ile
                405                 410                 415
Pro Asp Gly Trp Pro Asp Thr Thr Val Ala Glu Glu Leu Thr Pro Ala
            420                 425                 430
Gly Asp Tyr Ala Ile Thr Asn Glu Thr Gly Asn Asp Ile Thr Thr Ala
        435                 440                 445
Ala Ser Tyr Asp Ser Ala Ser Ala Ile Lys Asn Thr Thr Asn Phe Arg
    450                 455                 460
Gly Met Tyr Ile Cys Gly Ser Leu Gln Arg Ala Trp Gly Asp Lys Lys
465                 470                 475                 480
Ile Ser Asn Thr Ala Phe Ile Thr Thr Gly Thr Val Ser Asp Asn Lys
                485                 490                 495
Leu Lys Pro Ser Asn Ile Ile Asp Gln Ser Lys Ile Ala Val Phe Gln
            500                 505                 510
Asp Thr His Ala Asn Lys Glu Val Gln Thr Ser Asp Asp Thr Leu Ala
        515                 520                 525
Leu Leu Gly Tyr Thr Gly Ile Gly Glu Glu Ala Ile Gly Ala Asp Arg
    530                 535                 540
Asp Arg Val Val Arg Ile Ser Val Leu Pro Glu Ala Gly Ala Arg Gly
545                 550                 555                 560
Gly Asn His Pro Ile Phe Tyr Lys Asn Ser Ile Lys Leu Gly Tyr Val
                565                 570                 575
Ile Arg Ser Ile Asp Val Phe Asn Ser Gln Ile Leu His Thr Ser Arg
            580                 585                 590
Gln Leu Ser Leu Asn His Tyr Leu Leu Ser Pro Asp Ser Phe Ala Val
        595                 600                 605
Tyr Arg Ile Thr Asp Ser Asn Gly Ser Trp Phe Asp Ile Gly Ile Asp
    610                 615                 620
Ser Glu Gly Phe Ser Phe Val Gly Val Ser Asn Ile Gly Lys Leu Glu
625                 630                 635                 640
Phe Pro Leu Thr Ala Ser Tyr Met Gly Ile Gln Leu Ala Lys Ile Arg
                645                 650                 655
Leu Ala Ser Asn Ile Arg Ser Ser Met Thr Lys Ile
```

<210> SEQ ID NO 16
<211> LENGTH: 2007
<212> TYPE: DNA
<213> ORGANISM: feline calicivirus

<400> SEQUENCE: 16

```
atgtgctcaa cctgcgctaa cgtgcttaaa tactatgatt gggatcccca ctttagattg     60
gttatcaacc ccaacaaatt tctgtctgtt ggcttttgcg ataaccctct tatgtgttgt    120
taccctgaat tacttcctga atttggaact gtgtgggact gtgatcagtc tccactgcaa    180
atttacttag agtctatcct tggtgatgat gagtgggctt gcacctatga agcagttgat    240
ccgtgcgtac caccgatgca ctgggatgag gctgggaaga tttttcagcc acaccctggt    300
gttcttatgc accatcttat tggtcaagtt gccaaggcgt gggatccaga tctaccactt    360
ttccgcatgg aagcagatga tggatccatt acagcgcccg agcaaggtac agtagttggc    420
ggtgtcattg ctgagcctag tgctcaaatg tccgcggctg ctgacatggc cactgggaag    480
agcgtggact cggagtggga agctttcttt tccttccaca ccagtgtaaa ttggagtaca    540
tcagaaaccc aaggaaagat tctcttcaaa caaaccttag gtccccttct caacccctat    600
ctctcgcatc ttgcaaagct ttatgtcgct tggtccgggt ctgttgatgt taggttttct    660
atttctgggt ctggggtctt tgggggaaaa ctggctgcca ttgttgtacc accaggaatt    720
gatcctgtcc aaagcacgtc aatgttacag taccccccacg ttctttttga cgctcgccaa    780
gtggaacctg ttatcttctc aattcctgat ttaagaagca cactctacca tcttatgtca    840
gacacagaca ctacatcact tgtgattatg gtgtacaatg atctcatcaa cccatatgct    900
aatgacacca actcatctgg gtgtattgtc actgtggaaa caaagcctgg tcctgatttc    960
aagttccatc ttttgaagcc ccctggttcc atgctgaccc acgggtctgt tccttcagat   1020
ttgataccaa aaacttcatc actatggatt ggcaatcggt attggtctga cataactgac   1080
tttgttattc gaccctttgt gttccaagcc aacaggcact ttgatttcaa tcaagaaact   1140
gctgggtgga gcactccaag gtttcgacca attaccatca acataagtgt taaaaacgca   1200
gcaaaacttg gcactggaat tgctactgat ttcattgttc caggcatccc cgatggttgg   1260
cctgacacaa ccatccctgg aagactgaca cctgctggtg attatgcaat aactaatgag   1320
aaaaataatg atatcacaac tgccagtggg tatgactcag cactttccat caccaacaat   1380
accaacttca aggggatgta catctgtggt tcgctgcaaa gggcttgggg agataaaaag   1440
atctccaaca ctgcattcat cacaactgga acggttaatg gcaacatgct ggagcccagc   1500
aatgtcattg atccaacaaa gattgcagta ttccaggaca cccatgctaa ccaagatgtc   1560
caaacatctg atgacactct ggctttgctt ggatatacag ggattggcga ggaagctatt   1620
ggagctgatc gtgacagagt agtgcgcatt agtgtgctac ctgaaaccgg ggctcgtggt   1680
ggaaatcatc caatctttta caaaaactca attaagctag gatatgtgat caggtctatt   1740
gatgtgttca actctcaaat ccttcacacc tctaggcaac tctctctcaa tcactatcta   1800
ctatcacctg actcttttgc tgtttatagg ataatagact ctaatggttc atggtttgat   1860
attggcattg atagtgatgg cttctctttt gtcggtgtct ctaatattgg taaattggaa   1920
tttcctttaa cagcctccta catgggaatt caattggcaa agattcgtct tgcctctaac   1980
attaggagca ccatgattaa attatga                                        2007
```

<210> SEQ ID NO 17
<211> LENGTH: 668
<212> TYPE: PRT
<213> ORGANISM: feline calicivirus

<400> SEQUENCE: 17

```
Met Cys Ser Thr Cys Ala Asn Val Leu Lys Tyr Tyr Asp Trp Asp Pro
1               5                   10                  15

His Phe Arg Leu Val Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Ala Cys Thr Tyr Glu Ala Val Asp
65                  70                  75                  80

Pro Cys Val Pro Pro Met His Trp Asp Glu Ala Gly Lys Ile Phe Gln
                85                  90                  95

Pro His Pro Gly Val Leu Met His His Leu Ile Gly Gln Val Ala Lys
            100                 105                 110

Ala Trp Asp Pro Asp Leu Pro Leu Phe Arg Met Glu Ala Asp Asp Gly
        115                 120                 125

Ser Ile Thr Ala Pro Glu Gln Gly Thr Val Val Gly Val Ile Ala
    130                 135                 140

Glu Pro Ser Ala Gln Met Ser Ala Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Thr
            180                 185                 190

Leu Gly Pro Leu Leu Asn Pro Tyr Leu Ser His Leu Ala Lys Leu Tyr
        195                 200                 205

Val Ala Trp Ser Gly Ser Val Asp Val Arg Phe Ser Ile Ser Gly Ser
    210                 215                 220

Gly Val Phe Gly Gly Lys Leu Ala Ala Ile Val Val Pro Pro Gly Ile
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Thr Leu Tyr His Leu Met Ser Asp Thr Asp Thr Thr Ser Leu Val
        275                 280                 285

Ile Met Val Tyr Asn Asp Leu Ile Asn Pro Tyr Ala Asn Asp Thr Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Thr Ser Ser Leu Trp Ile Gly Asn
            340                 345                 350

Arg Tyr Trp Ser Asp Ile Thr Asp Phe Val Ile Arg Pro Phe Val Phe
        355                 360                 365

Gln Ala Asn Arg His Phe Asp Phe Asn Gln Glu Thr Ala Gly Trp Ser
    370                 375                 380
```

-continued

```
Thr Pro Arg Phe Arg Pro Ile Thr Ile Asn Ile Ser Val Lys Asn Ala
385                 390                 395                 400

Ala Lys Leu Gly Thr Gly Ile Ala Thr Asp Phe Ile Val Pro Gly Ile
                405                 410                 415

Pro Asp Gly Trp Pro Asp Thr Thr Ile Pro Gly Arg Leu Thr Pro Ala
            420                 425                 430

Gly Asp Tyr Ala Ile Thr Asn Glu Lys Asn Asn Asp Ile Thr Thr Ala
            435                 440                 445

Ser Gly Tyr Asp Ser Ala Leu Ser Ile Thr Asn Asn Thr Asn Phe Lys
        450                 455                 460

Gly Met Tyr Ile Cys Gly Ser Leu Gln Arg Ala Trp Gly Asp Lys Lys
465                 470                 475                 480

Ile Ser Asn Thr Ala Phe Ile Thr Thr Gly Thr Val Asn Gly Asn Met
                485                 490                 495

Leu Glu Pro Ser Asn Val Ile Asp Pro Thr Lys Ile Ala Val Phe Gln
            500                 505                 510

Asp Thr His Ala Asn Gln Asp Val Gln Thr Ser Asp Thr Leu Ala
            515                 520                 525

Leu Leu Gly Tyr Thr Gly Ile Gly Glu Glu Ala Ile Gly Ala Asp Arg
530                 535                 540

Asp Arg Val Val Arg Ile Ser Val Leu Pro Glu Thr Gly Ala Arg Gly
545                 550                 555                 560

Gly Asn His Pro Ile Phe Tyr Lys Asn Ser Ile Lys Leu Gly Tyr Val
                565                 570                 575

Ile Arg Ser Ile Asp Val Phe Asn Ser Gln Ile Leu His Thr Ser Arg
            580                 585                 590

Gln Leu Ser Leu Asn His Tyr Leu Leu Ser Pro Asp Ser Phe Ala Val
        595                 600                 605

Tyr Arg Ile Ile Asp Ser Asn Gly Ser Trp Phe Asp Ile Gly Ile Asp
610                 615                 620

Ser Asp Gly Phe Ser Phe Val Gly Val Ser Asn Ile Gly Lys Leu Glu
625                 630                 635                 640

Phe Pro Leu Thr Ala Ser Tyr Met Gly Ile Gln Leu Ala Lys Ile Arg
                645                 650                 655

Leu Ala Ser Asn Ile Arg Ser Thr Met Ile Lys Leu
                660                 665
```